United States Patent
Jiang et al.

(10) Patent No.: US 11,512,160 B2
(45) Date of Patent: Nov. 29, 2022

(54) FREE-STANDING NON-FOULING POLYMERS, THEIR COMPOSITIONS, AND RELATED MONOMERS

(71) Applicant: University of Washington, Seattle, WA (US)

(72) Inventors: Shaoyi Jiang, Redmond, WA (US); Tao Bai, Seattle, WA (US); Jean-René Ella-Menye, Seattle, WA (US); Hsiang-Chieh Hung, Seattle, WA (US); Priyesh Jain, Seattle, WA (US); Andrew Sinclair, Seattle, WA (US); Harihara Subramanian Sundaram, Seattle, WA (US); Yang Li, Seattle, WA (US); Peng Zhang, Seattle, WA (US)

(73) Assignee: University of Washington, Seattle, WA (US)

( * ) Notice: Subject to any disclaimer, the term of this patent is extended or adjusted under 35 U.S.C. 154(b) by 342 days.

(21) Appl. No.: 15/578,633

(22) PCT Filed: Jun. 2, 2016

(86) PCT No.: PCT/US2016/035585
§ 371 (c)(1),
(2) Date: Nov. 30, 2017

(87) PCT Pub. No.: WO2017/003639
PCT Pub. Date: Jan. 5, 2017

(65) Prior Publication Data
US 2019/0002625 A1    Jan. 3, 2019

Related U.S. Application Data

(60) Provisional application No. 62/169,822, filed on Jun. 2, 2015.

(51) Int. Cl.
*C08F 220/34* (2006.01)
*C08F 220/36* (2006.01)
(Continued)

(52) U.S. Cl.
CPC ............ *C08F 220/34* (2013.01); *A61K 47/58* (2017.08); *A61K 47/59* (2017.08); *A61K 47/593* (2017.08);
(Continued)

(58) Field of Classification Search
None
See application file for complete search history.

(56) References Cited

U.S. PATENT DOCUMENTS

| 3,641,199 A | 2/1972 | Niederhauser et al. |
| 6,641,618 B1 | 11/2003 | Legrand et al. |

(Continued)

FOREIGN PATENT DOCUMENTS

| CN | 101918462 A | 12/2010 |
| CN | 102770407 A | 11/2012 |

(Continued)

OTHER PUBLICATIONS

Masterton and Hurley, Chemistry, Principles and Reactions, pp. 180-182, 5th Ed, 2004. (Year: 2004).*

(Continued)

*Primary Examiner* — Satya B Sastri
(74) *Attorney, Agent, or Firm* — Christensen O'Connor Johnson Kindness PLLC

(57) ABSTRACT

Free-standing non-fouling polymers and polymeric compositions, monomers and macromonomers for making the polymers and polymeric compositions, objects made from
(Continued)

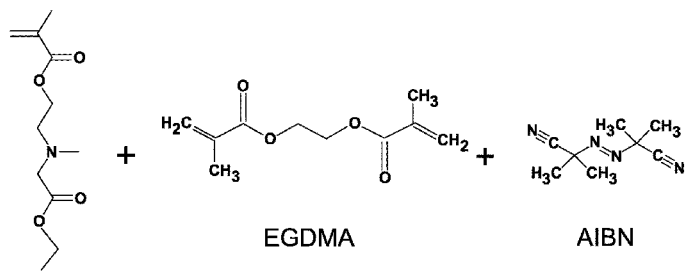

Compression test before hydrolysis

| Crosslinker% | Stress (Mpa) | Strain % | Modulus (Mpa) |
|---|---|---|---|
| 0 | --- | --- | --- |
| 0.5 | 5.7 | 90 | 0.09 |
| 1.0 | 5.2 | 82 | 0.32 |
| 2.0 | 3.2 | 64 | 0.74 | the polymers and polymeric compositions, and methods for making and using the polymers and polymeric compositions.

19 Claims, 8 Drawing Sheets

(51) Int. Cl.
| | | |
|---|---|---|
| C08F 220/48 | (2006.01) | |
| C08F 220/44 | (2006.01) | |
| C08F 220/50 | (2006.01) | |
| C08F 220/42 | (2006.01) | |
| C08F 220/60 | (2006.01) | |
| A61K 47/58 | (2017.01) | |
| A61K 47/59 | (2017.01) | |
| C07F 9/09 | (2006.01) | |
| C07C 229/16 | (2006.01) | |
| C07C 265/04 | (2006.01) | |
| C07C 229/12 | (2006.01) | |
| C07C 255/23 | (2006.01) | |
| C07C 237/22 | (2006.01) | |
| C07C 253/30 | (2006.01) | |
| C07C 255/26 | (2006.01) | |
| C09D 5/16 | (2006.01) | |
| C09D 7/65 | (2018.01) | |
| C08G 18/38 | (2006.01) | |
| C08G 18/78 | (2006.01) | |
| C08G 61/08 | (2006.01) | |
| C08G 61/12 | (2006.01) | |
| C08G 63/685 | (2006.01) | |
| C08G 69/26 | (2006.01) | |
| C08G 69/42 | (2006.01) | |
| C08G 73/02 | (2006.01) | |
| C08G 73/06 | (2006.01) | |
| C08L 35/02 | (2006.01) | |
| C08L 65/00 | (2006.01) | |
| C08L 67/02 | (2006.01) | |
| C08L 75/04 | (2006.01) | |
| C08L 77/06 | (2006.01) | |
| C08L 79/02 | (2006.01) | |
| C08L 79/04 | (2006.01) | |
| C09D 135/02 | (2006.01) | |
| C09D 165/00 | (2006.01) | |
| C09D 167/02 | (2006.01) | |
| C09D 175/04 | (2006.01) | |
| C09D 177/06 | (2006.01) | |
| C09D 179/02 | (2006.01) | |
| C09D 179/04 | (2006.01) | |
| C08G 61/06 | (2006.01) | |
| C08G 63/00 | (2006.01) | |
| C08F 222/32 | (2006.01) | |

(52) U.S. Cl.
CPC .......... *A61K 47/595* (2017.08); *C07C 229/12* (2013.01); *C07C 229/16* (2013.01); *C07C 237/22* (2013.01); *C07C 253/30* (2013.01); *C07C 255/23* (2013.01); *C07C 255/26* (2013.01); *C07C 265/04* (2013.01); *C07F 9/091* (2013.01); *C08F 220/36* (2013.01); *C08F 220/42* (2013.01); *C08F 220/44* (2013.01); *C08F 220/48* (2013.01); *C08F 220/50* (2013.01); *C08F 220/603* (2020.02); *C08G 18/3821* (2013.01); *C08G 18/78* (2013.01); *C08G 61/08* (2013.01); *C08G 61/12* (2013.01); *C08G 63/6856* (2013.01); *C08G 69/26* (2013.01); *C08G 69/42* (2013.01); *C08G 73/0206* (2013.01); *C08G 73/0226* (2013.01); *C08G 73/0233* (2013.01); *C08G 73/0611* (2013.01); *C08L 35/02* (2013.01); *C08L 65/00* (2013.01); *C08L 67/02* (2013.01); *C08L 75/04* (2013.01); *C08L 77/06* (2013.01); *C08L 79/02* (2013.01); *C08L 79/04* (2013.01); *C09D 5/1637* (2013.01); *C09D 5/1662* (2013.01); *C09D 7/65* (2018.01); *C09D 135/02* (2013.01); *C09D 165/00* (2013.01); *C09D 167/02* (2013.01); *C09D 175/04* (2013.01); *C09D 177/06* (2013.01); *C09D 179/02* (2013.01); *C09D 179/04* (2013.01); *C08F 222/328* (2020.02); *C08G 61/06* (2013.01); *C08G 63/00* (2013.01); *C08G 2261/11* (2013.01); *C08G 2261/143* (2013.01); *C08G 2261/1426* (2013.01); *C08G 2261/1432* (2013.01); *C08G 2261/228* (2013.01); *C08G 2261/334* (2013.01); *C08G 2261/3321* (2013.01); *C08G 2261/3324* (2013.01); *C08G 2261/3342* (2013.01); *C08G 2261/418* (2013.01); *C08G 2261/62* (2013.01); *C08G 2261/72* (2013.01); *C09D 5/165* (2013.01)

(56) References Cited

U.S. PATENT DOCUMENTS

| | | | |
|---|---|---|---|
| 6,852,816 B2 * | 2/2005 | Lewis | C08F 4/40 524/710 |
| 8,617,592 B2 * | 12/2013 | Jiang | A61K 9/5153 424/450 |
| 8,835,671 B2 * | 9/2014 | Jiang | A61L 31/10 560/222 |
| 2010/0249267 A1 | 9/2010 | Jiang et al. | |
| 2011/0218290 A1 | 9/2011 | Webster et al. | |
| 2012/0259021 A1 | 10/2012 | Jiang et al. | |
| 2013/0158517 A1 * | 6/2013 | Bouchard | A61L 29/14 604/529 |
| 2013/0178125 A1 * | 7/2013 | Jiang | B63B 59/04 428/524 |
| 2016/0296322 A1 * | 10/2016 | Edelman | A61F 2/2412 |

FOREIGN PATENT DOCUMENTS

| | | |
|---|---|---|
| CN | 102906127 A | 1/2013 |
| JP | 2011-503332 A | 1/2011 |
| JP | 2011-504526 A | 2/2011 |
| WO | 2008/019381 A1 | 2/2008 |
| WO | 2009/067562 A1 | 5/2009 |
| WO | 2009/067565 A2 | 5/2009 |
| WO | 2011/057219 A2 | 5/2011 |
| WO | 2011/057225 A2 | 5/2011 |
| WO | 2016/012472 A1 | 1/2016 |

OTHER PUBLICATIONS

International Preliminary Report on Patentability dated Dec. 5, 2017, issued in corresponding International Application No. PCT/US16/35585, filed Jun. 2, 2016, 7 pages.
International Search Report and Written Opinion dated Mar. 13, 2017, issued in corresponding International Application No. PCT/US16/35585, filed Jun. 2, 2016, 10 pages.
Yang, W.J., et al., "Polymer Brush Coatings for Combating Marine Biofouling," Progress in Polymer Science 39(5):11017-1042, May 2014.
Notification of the First Office Action dated Nov. 5, 2019, issued in corresponding Chinese Application No. 201680040723.1, filed Jun. 2, 2016, 32 pages.

(56) References Cited

OTHER PUBLICATIONS

Extended European Search Report dated Nov. 30, 2018, issued in corresponding European Application No. 16818431.5, filed Jun. 2, 2016, 12 pages.
European Office Action dated Mar. 31, 2020, issued in corresponding European Application No. 16818431.5, filed Jun. 2, 2016, 4 pages.
Japanese Notice of Reasons for Rejection dated Jul. 14, 2020, in corresponding Application No. 2018-515187, filed Jun. 2, 2016, 10 pages.
European Examination Communication dated Nov. 26, 2020, issued in corresponding European Application No. 16 818 431.5, filed Jun. 22, 2016, 4 pages.
Second Chinese Office Action dated Jan. 8, 2021, issued in corresponding Application No. 201680040723.1, filed Jun. 2, 2016, 35 pages.
Office Action dated Sep. 3, 2021, issued in corresponding Chinese Application No. 201680040723.1, filed Jun. 2, 2016, 27 pages.
Decision of Refusal dated Mar. 12, 2021, issued in corresponding Japanese Application No. 2018-515187, 6 pages.
Office Action dated Aug. 9, 2022 in corresponding Japanese Application No. 2021-117109, filed Jul. 15, 2021, 6 pages.

* cited by examiner

| Hydrolysis time (hour) | Stress (MpA) | Strain % | Modulus (MpA) | % of TCPS fouling |
|---|---|---|---|---|
| 1.0 | 5.0 | 80 | 0.32 | 42.3 |
| 2.0 | 4.9 | 75 | 0.25 | 9.5 |

*FIG. 3*

|  | Fracture tensile stress (MPa) | Fracture tensile strain (%) | Young's modulus (MPa) |
|---|---|---|---|
| Before hydrolysis | 1.165 ± 0.168 | 142.23 ± 30.17 | 1.286 ± 0.378 |
| After hydrolysis | 0.939 ± 0.086 | 103.62 ± 8.41 | 1.091 ± 0.110 |

FIG. 8

FREE-STANDING NON-FOULING POLYMERS, THEIR COMPOSITIONS, AND RELATED MONOMERS

CROSS-REFERENCE TO RELATED APPLICATION

This application claims the benefit of U.S. Application No. 62/169,822, filed Jun. 2, 2015, expressly incorporated herein by reference in its entirety.

STATEMENT OF GOVERNMENT LICENSE RIGHTS

This invention was made with Government support under N00014-15-1-2277 and N00014-14-1-0090 awarded by the Office of Naval Research and DMR 1307375 awarded by the National Science Foundation. The Government has certain rights in the invention.

BACKGROUND OF THE INVENTION

Polymeric materials with excellent non-fouling properties are known. Polymeric materials with strong mechanical properties are also known. However, polymeric materials having both excellent non-fouling properties and strong mechanical properties are not known. Polymeric materials having excellent non-fouling properties generally have weak mechanical properties, and high-strength polymeric materials generally suffer from high protein adsorption.

Despite the development of polymeric materials having excellent non-fouling properties and the development of polymeric materials high-strength mechanical properties, a need exists for polymeric materials having both excellent non-fouling properties and high mechanical strength. The present invention seeks to fulfill this need and provides further related advantages.

SUMMARY OF THE INVENTION

The present invention provides polymeric materials having both excellent non-fouling properties and high mechanical strength. The polymeric materials are polymers and bulk materials prepared from monomers and macromonomers that impart advantageous non-fouling and high strength properties to the polymer and bulk materials.

In one aspect, the invention provides monomers useful for making polymers and bulk materials of the invention.

In one embodiment, the invention provides a monomer having a formula selected from the group consisting of:

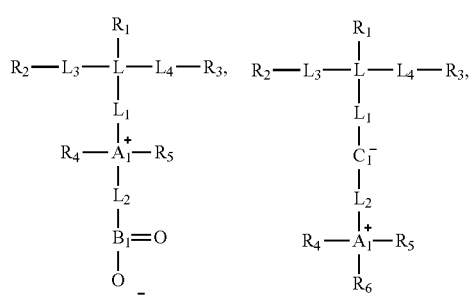

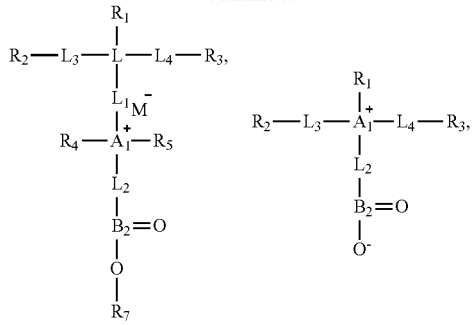

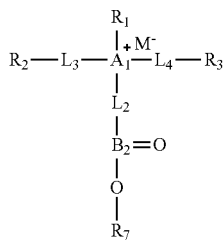

and
wherein
$R_1$ is selected from the group consisting of hydrogen, fluorine, trifluoromethyl, $C_1$-$C_{20}$ alkyl, and $C_6$-$C_{12}$ aryl groups, or CN;

$R_4$, $R_5$, $R_6$, and $R_7$ are independently selected from the group consisting of hydrogen, $C_1$-$C_{20}$ alkyl, and $C_6$-$C_{12}$ aryl, cyclic alkyl, fluoroalkyl, and void;

$R_2$ and $R_3$ are independently selected from a functional group suitable for polymerization by addition, condensation, or ring opening;

L is C or Si or void;

$L_1$, $L_3$, and $L_4$ are independently selected from —(CH$_2$)$_x$—, —(CH(CN))$_x$—, —C(=O)NH(CH$_2$)$_x$—, —C(=O)O(CH$_2$)$_x$—, —C(=O)OC(=O)O(CH$_2$)$_x$—, —(CH$_2$)$_x$—O—(CH$_2$)$_x$—, and (CH$_2$)$_x$—S—S—(CH$_2$)$_x$—, where x at each occurrence is an integer independently selected from 0 to 20, combinations thereof, or void;

$L_2$ is independently selected from —(CH$_2$)$_x$—, or —(CH(CN))$_x$—, where x is an integer from 1 to 20;

$A_1$ is N;

$B_1$ is C, S, SO, PO, or PO$_2$—;

$B_2$ is C or SO;

$C_1$ is PO$_4$; and

M is selected from Cl, Br, I, SO$_4$, NO$_3$ClO$_4$, BF$_4$, PF$_6$, N(SO$_2$CF$_3$)$_2$, SO$_3$CF$_3$, RCOO (R is $C_1$-$C_{20}$ alkyl), lactate, benzoate, and salicylate, or void.

In another embodiment, the invention provides a monomer having a formula selected from the group consisting of:

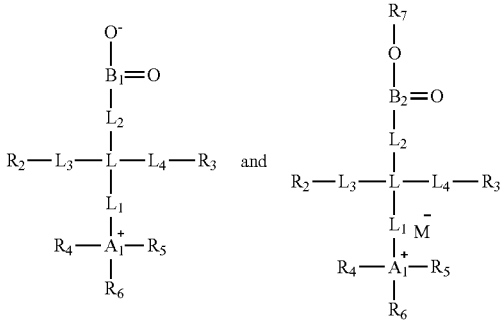

wherein $R_2$ and $R_3$ are independently selected from a functional group suitable for polymerization by addition, condensation, or ring opening;

L is C or Si or void;

$L_1$, $L_2$, $L_3$, and $L_4$ are independently selected from —$(CH_2)_x$—, —$(CH(CN))_x$—, —$C(=O)NH(CH_2)_x$—, —$C(=O)O(CH_2)_x$—, —$C(=O)OC(=O)O(CH_2)_x$—, —$(CH_2)_x$—O—$(CH_2)_x$—, and —$(CH_2)_x$—S—S—$(CH_2)_x$—, where x at each occurrence is an integer independently selected from 0 to 20, combinations thereof, or void;

$A_1$ is N;

$B_1$ is C, S, SO, PO, or $PO_2$—;

$B_2$ is C or SO;

$C_1$ is $PO_4$; and

M is selected from Cl, Br, I, $SO_4$, $NO_3ClO_4$, $BF_4$, $PF_6$, $N(SO_2CF_3)_2$, $SO_3CF_3$, RCOO (R is $C_1$-$C_{20}$ alkyl), lactate, benzoate, and salicylate, or void.

In a further embodiment, the invention provides a monomer having a formula selected from the group consisting of:

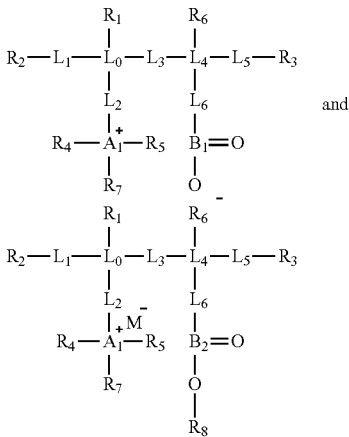

wherein $R_1$ and $R_6$ is selected from the group consisting of hydrogen, fluorine, trifluoromethyl, C1-C20 alkyl, C6-C12 aryl, CN, cyclic alkyl, fluoro alkyl, and void;

$R_4$, $R_5$, $R_7$, and $R_8$ are independently selected from the group consisting of hydrogen, C1-C20 alkyl, C6-C12 aryl, cyclic alkyl group, fluoro alkyl, and void;

$R_2$ and $R_3$ are independently selected from a functional group suitable for polymerization by addition, condensation, or ring opening;

$L_0$ and $L_4$ are C or Si or void;

$L_1$, $L_2$, $L_3$, $L_5$, and $L_6$ are independently selected from —$(CH_2)_x$—, —$(CH(CN))_x$—, —$C(=O)NH(CH_2)_x$—, —$C(=O)O(CH_2)_x$—, —$C(=O)OC(=O)O(CH_2)_x$—, —$(CH_2)_x$—O—$(CH_2)_x$—, and —$(CH_2)_x$—S—S—$(CH_2)_x$—, where x at each occurrence is an integer independently selected from 0 to 20, combinations thereof, or void;

$A_1$ is N;

$B_1$ is C, S, SO, PO, or $PO_2$—;

$B_2$ is C or SO;

$C_1$ is $PO_4$; and

M is selected from Cl, Br, I, $SO_4$, $NO_3ClO_4$, $BF_4$, $PF_6$, $N(SO_2CF_3)_2$, $SO_3CF_3$, RCOO (R is C1-C20 alkyl), lactate, benzoate, salicylate, or void.

For each of the above embodiments, $R_2$ and $R_3$ may further be selected from a functional group suitable for free radical polymerization. Such functional groups are known to those in the art and include, for example, ethylenic moieties, such as vinyl moieties including vinyl esters and vinyl amides, among others.

In certain embodiments, the invention provides macromonomers useful for making the polymers and bulk materials of the invention.

In one embodiment, the invention provides a macromonomer having a formula selected from the group consisting of:

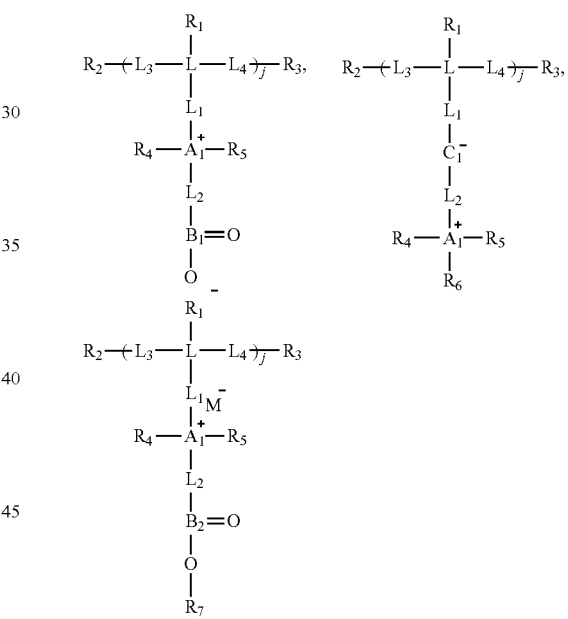

wherein $R_1$ is selected from the group consisting of hydrogen, fluorine, trifluoromethyl, $C_1$-$C_{20}$ alkyl, $C_6$-$C_{12}$ aryl, CN;

$R_4$, $R_5$, $R_6$, and $R_7$, are independently selected from the group consisting of hydrogen, $C_1$-$C_{20}$ alkyl, $C_6$-$C_{12}$ aryl, cyclic alkyl, fluoro alkyl, and void;

$R_2$ and $R_3$ are independently selected from a functional group suitable for polymerization by addition, condensation, or ring opening, or free radical polymerization; L is C or Si or void;

$L_1$, $L_3$, and $L_4$ are independently selected from —$(CH_2)_x$—, —$(CH(CN))_x$—, —$C(=O)NH(CH_2)_x$—, —$C(=O)O(CH_2)_x$—, —$C(=O)OC(=O)O(CH_2)_x$—, —$(CH_2)_x$—O—$(CH_2)_x$—, and —$(CH_2)_x$—S—S—$(CH_2)_x$—, where x at each occurrence is an integer independently selected from 0 to 20, combinations thereof, or void;

$L_2$ is independently selected from —$(CH_2)_x$—, or —$(CH(CN))_x$—, where x is an integer from 1 to 20;

$A_1$ is N;

$B_1$ is C, S, SO, PO, or $PO_2$;

$B_2$ is C or SO;

$C_1$ is $PO_4$;

M is selected from Cl, Br, I, $SO_4$, $NO_3ClO_4$, $BF_4$, $PF_6$, $N(SO_2CF_3)_2$, $SO_3CF_3$, RCOO (R is $C_1$-$C_{20}$ alkyl), lactate, benzoate, salicylate, or void; and j is an integer from 1 to about 1000.

In another embodiment, the invention provides a macromonomer having a formula selected from the group consisting of:

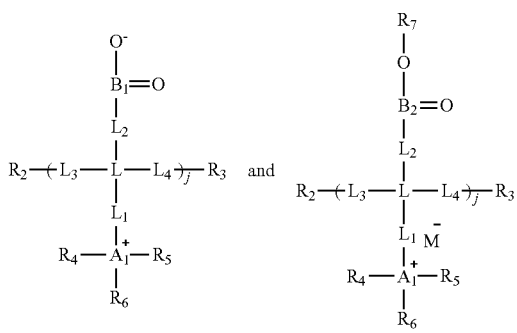

wherein $R_4$, $R_5$, $R_6$, and $R_7$ are independently selected from the group consisting of hydrogen, $C_1$-$C_{20}$ alkyl, $C_6$-$C_{12}$ aryl, cyclic alkyl, fluoro alkyl, and void;

$R_2$ and $R_3$ are independently selected from a functional group suitable for polymerization by addition, condensation, or ring opening, or free radical polymerization;

L is C or Si or void;

$L_1$, $L_3$, and $L_4$ are independently selected from —$(CH_2)_x$—, —$(CH(CN))_x$—, —$C(=O)NH(CH_2)_x$—, —$C(=O)O(CH_2)_x$—, —$C(=O)OC(=O)O(CH_2)_x$—, —$(CH_2)_x$—O—$(CH_2)_x$—, and $(CH_2)_x$—S—S—$(CH_2)_x$—, where x at each occurrence is an integer independently selected from 0 to 20, combinations thereof, or void;

$L_2$ is independently selected from —$(CH_2)_x$—, or —$(CH(CN))_x$—, where x is an integer from 1 to 20;

$A_1$ is N;

$B_1$ is C, S, SO, PO, or $PO_2$—;

$B_2$ is C or SO;

M is selected from Cl, Br, I, $SO_4$, $NO_3ClO_4$, $BF_4$, $PF_6$, $N(SO_2CF_3)_2$, $SO_3CF_3$, RCOO (R is $C_1$-$C_{20}$ alkyl), lactate, benzoate, salicylate, or void; and j is an integer from 1 to about 1000.

In a further embodiment, the invention provides a macromonomer having a formula selected from the group consisting of:

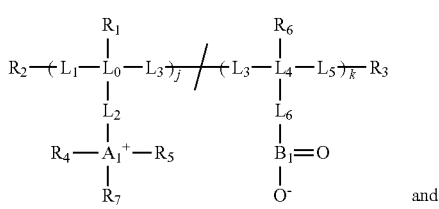

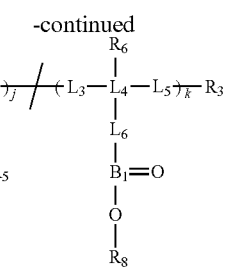

wherein $R_1$ and $R_6$ are selected from the group consisting of hydrogen, fluorine, trifluoromethyl, C1-C20 alkyl, C6-C12 aryl, CN, cyclic alkyl, fluoroalkyl, and void;

$R_4$, $R_5$, $R_7$, and $R_8$ are independently selected from the group consisting of hydrogen, C1-C20 alkyl, C6-C12 aryl, cyclic alkyl, fluoroalkyl, and void;

$R_2$ and $R_3$ are independently selected from a functional group suitable for polymerization by addition, condensation, or ring opening, or free radical polymerization;

$L_0$ and $L_4$ are C or Si or void;

$L_1$, $L_2$, $L_3$, $L_5$, and $L_6$ are independently selected from —$(CH_2)_x$—, —$(CH(CN))_x$—, —$C(=O)NH(CH_2)_x$—, —$C(=O)O(CH_2)_x$—, —$C(=O)OC(=O)O(CH_2)_x$—, —$(CH_2)_x$—O—$(CH_2)_x$—, and —$(CH_2)_x$—S—S—$(CH_2)_x$—, where x at each occurrence is an integer independently selected from 0 to 20, combinations thereof, or void;

$A_1$ is N;

$B_1$ is C, S, SO, PO, or $PO_2$—;

$B_2$ is C or SO;

$C_1$ is $PO_4$;

M is selected from Cl, Br, I, $SO_4$, $NO_3ClO_4$, $BF_4$, $PF_6$, $N(SO_2CF_3)_2$, $SO_3CF_3$, RCOO (R is C1-C20 alkyl), lactate, benzoate, and salicylate or void;

j and k are integers independently selected from 1 to about 1000.

In other embodiments, the invention provides monomers useful for making the polymers and bulk materials of the invention.

In one embodiment, the invention provides a monomer having the formula:

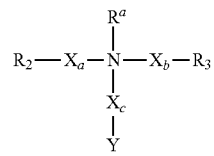

or a salt thereof, wherein $R_2$ and $R_3$ are independently selected from a functional group suitable for polymerization by addition, condensation, or ring opening, or free radical polymerization;

$X_a$ is selected from —$(CH_2)_n$—, where n is 0 to 6;

$X_b$ is —$(CH_2)_p$—, where p is 1 to 6;

$R^a$ is selected from hydrogen and C1-C6 alkyl;

$X_c$ is —$(CH_2)_q$—, where q is 1 to 6; and

Y is selected from $CO_2^-$, $SO_3^-$, or $PO_4^{2-}$.

In another embodiment, the invention provides a monomer having the formula:

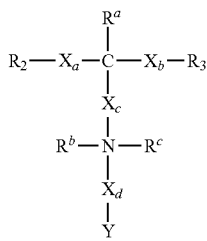

or a salt thereof,
wherein $R_2$ and $R_3$ are independently selected from a functional group suitable for polymerization by addition, condensation, or ring opening, or free radical polymerization;

$X_a$ is selected from —$(CH_2)_n$—, where n is 0 to 6;

$X_b$ is —$(CH_2)_p$—, where p is 1 to 6;

$R^a$, $R^b$, and $R^c$ are independently selected from hydrogen and C1-C6 alkyl;

$X_c$ is —$(CH_2)_q$—, where q is 1 to 6;

$X_d$ is —$(CH_2)_r$—, where r is 1 to 6; and

Y is selected from $CO_2^-$, $SO_3^-$, or $PO_4^{2-}$.

In a further embodiment, the invention provides a monomer having the formula:

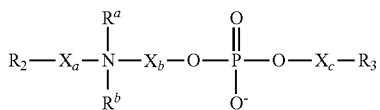

or a salt thereof,
wherein $R_2$ and $R_3$ are independently selected from a functional group suitable for polymerization by addition, condensation, or ring opening, or free radical polymerization;

$X_a$ is selected from —$(CH_2)_n$—, where n is 0 to 6;

$X_b$ is —$(CH_2)_p$—, where p is 1 to 6;

$R^a$ and $R^b$ are independently selected from hydrogen and C1-C6 alkyl; and $X_c$ is —$(CH_2)_q$—, where q is 1 to 6.

In certain embodiment of the monomers and macromonomers of the invention, $R_2$ and $R_3$ are independently selected from the group consisting of F, Cl, Br, I, SH, protected thiols, $NH_2$, —NH— (secondary amine), N=C=O, protected NCO, N=C=S, COOH, COSH, C(=S)SH, OCOOH, OCOSH, OC(=S)OH, SC(=O)SH, SC(=S)SH, N(C=O)$NH_2$, N(C=NH)$NH_2$, N(C=S)$NH_2$, δ-valerolactone moiety, ε-caprolactone moiety, $CH_2$=CH—C(=O)—O—, $CH_2$=CH—C(=O)—NH—, $CH_2$=CH—C(=O)—S—, CN, $CH_2$=CH($CH_3$)—C(=O)—O—, $CH_2$=CH($CH_3$)—C(=O)—O—, OH, azides, alkynes, or void.

In certain embodiments, $R_2$ and $R_3$ are selected from the group consisting of —N=C=O and —N=C=S. In other embodiments, $R_2$ and $R_3$ are Michael acceptors, such as $CH_2$=CH—C(=O)—O—, $CH_2$=CH—C(=O)—NH—, $CH_2$=CH—C(=O)—S—, $CH_2$=CH($CH_3$)—C(=O)—O—, and $CH_2$=CH($CH_3$)—C(=O)—O—. In further embodiments, $R_2$ and $R_3$ are ring opening polymerization moieties or ring opening metathesis polymerization moieties, such as

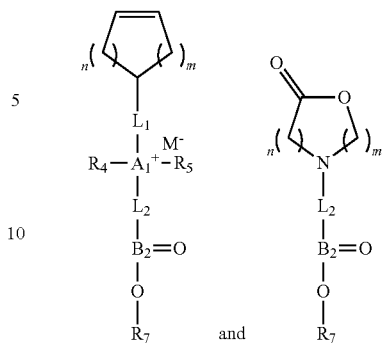

wherein m and n are independently selected from 1 to 3.

$R_4$ and $R_5$ are independently selected from the group consisting of hydrogen, $C_1$-$C_{20}$ alkyl, and $C_6$-$C_{12}$ aryl, cyclic alkyl, fluoroalkyl, and void;

$L_1$ is independently selected from —$(CH_2)_x$—, —C(=O)NH$(CH_2)_x$—, —C(=O)O$(CH_2)_x$—, —C(=O)OC(=O)O$(CH_2)_x$—, —$(CH_2)_x$—O—$(CH_2)_x$—, and —$(CH_2)_x$—S—S—$(CH_2)_x$—, where x at each occurrence is an integer independently selected from 0 to 20, combinations thereof, or void;

$L_2$ is —$(CH_2)_x$ where x is an integer from 1 to 20;

$A_1$ is N;

$B_2$ is C or SO; and

M is selected from Cl, Br, I, $SO_4$, $NO_3ClO_4$, $BF_4$, $PF_6$, N(SO$_2$CF$_3$)$_2$, SO$_3$CF$_3$, RCOO (R is $C_1$-$C_{20}$ alkyl), lactate, benzoate, and salicylate, or void.

In certain embodiments, the monomer is a stabilizing monomer that imparts advantageous strength properties to the polymers and bulk materials of the invention.

In certain of these embodiments, the monomer is a CN-substituted monomer that imparts a CN group to the polymer backbone. In this embodiment, the monomer has the formula:

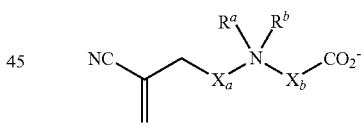

or a salt thereof,
wherein $X_a$ is selected from —O(C=O)(CH$_2$)$_n$— where n is 1 to 6, —O(CH$_2$)$_m$— where m is 1 to 6, or is absent;

$R^a$ and $R^b$ are independently selected from hydrogen and C1-C6 alkyl; and $X_b$ is —(CH$_2$)$_n$— where n is 1 to 6.

In certain of these embodiments, the monomer is a CN-substituted monomer that imparts a CN group to the polymer side chains. In this embodiment, the monomer has the formula:

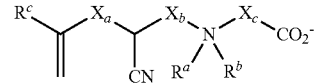

or a salt thereof, wherein $X_a$ is selected from —O(C=O)(CH$_2$)$_n$—, where n is 1 to 6, or —NH(C=O)(CH$_2$)$_m$—, where m is 1 to 6;

$R^a$ and $R^b$ are independently selected from hydrogen and C1-C6 alkyl; and $X_b$ is —(CH$_2$)$_p$—, where p is 1 to 6; and $X_c$ is —(CH$_2$)$_q$—, where q is 1 to 6.

In certain embodiments, the monomer is a stabilizing monomer that imparts advantageous strength properties to the polymers and bulk materials of the invention.

In certain of these embodiments, the stabilizing monomer is an amide- or diamide-containing monomer that imparts an amide or a diamide group to the polymer side chain. In one embodiment, the diamide-containing monomer has the formula:

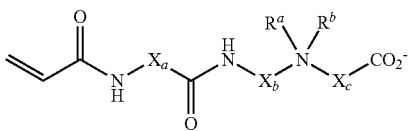

or a salt thereof,
wherein $X_a$ is selected from —(CH$_2$)$_n$—, where n is 0 to 6;

$X_b$ is —(CH$_2$)$_p$—, where p is 1 to 6;

$R^a$ and $R^b$ are independently selected from hydrogen and C1-C6 alkyl; and $X_c$ is —(CH$_2$)$_q$—, where q is 1 to 6.

In certain of these embodiments, the stabilizing monomer is a urea-containing monomer that imparts a urea group to the polymer side chain. In one embodiment, the urea-containing monomer has the formula:

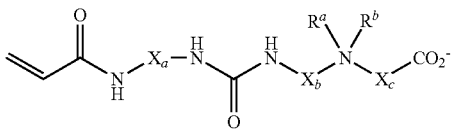

or a salt thereof,
wherein $X_a$ is selected from —(CH$_2$)$_n$—, where n is 0 to 6;

$X_b$ is —(CH$_2$)$_p$—, where p is 1 to 6;

$R^a$ and $R^b$ are independently selected from hydrogen and C1-C6 alkyl; and $X_c$ is —(CH$_2$)$_q$—, where q is 1 to 6.

In another aspect of the invention, polymers and bulk materials comprising the polymers are provided.

In certain embodiments, the polymer or bulk material is prepared by polymerizing a monomer or macromonomer of the invention, as described herein.

In other embodiments, the polymer or bulk material is prepared by polymerizing a monomer or macromonomer of the invention, as described herein, with a second monomer (e.g., a monomer that does not include either a zwitterionic or zwitterionic precursor group).

In certain embodiments, the polymer has the formula:

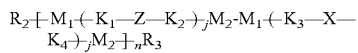

wherein $K_1$, $K_2$, $K_3$, and $K_4$ are independently selected from —(CH$_2$)$_x$—, —(CH(CN))$_x$—, —C(=O)NH(CH$_2$)$_x$—, —C(=O)O(CH$_2$)$_x$—, —C(=O)OC(=O)O(CH$_2$)$_x$—, —(CH$_2$)$_x$—O—(CH$_2$)$_x$—, and —(CH$_2$)$_x$—S—S—(CH$_2$)$_x$—, where x at each occurrence is an integer independently selected from 0 to 20, combinations thereof, or void;

$R_2$ and $R_3$ are independently selected from H, F, Cl, Br, I, OH, SH, protected thiols, NH$_2$, —NH— (secondary amine), N=C=O, N=C=S, COOH, COSH, C(=S)SH, OCOOH, OCOSH, OC(=S)OH, SC(=O)SH, SC(=S)SH, N(C=O)NH$_2$, N(C=NH)NH$_2$, N(C=S)NH$_2$, δ-valerolactone moiety, ε-caprolactone moiety, CH$_2$=CH—C(=O)—O—, CH$_2$=CH—C(=O)—NH—, CH$_2$=CH—C(=O)—S—, CN, CH$_2$=CH(CH$_3$)—C(=O)—O—, CH$_2$=CH(CH$_3$)—C(=O)—NH—, or void;

n is an integer from 5 to about 10,000;

j is an integer from 1 to about 1000;

$M_1$ and $M_2$ are independently selected from —(CH$_2$)$_x$—, —(CH(CN))$_x$—, —C(=O)NH(CH$_2$)$_x$—, —C(=O)O(CH$_2$)$_x$—, —C(=O)OC(=O)O(CH$_2$)$_x$—, —(CH$_2$)$_x$—O—(CH$_2$)$_x$—, and —(CH$_2$)$_x$—S—S—(CH$_2$)$_x$—, where x at each occurrence is an integer independently selected from 0 to 20, combinations thereof, or void; and Z and X are independently selected from zwitterionic groups.

In certain embodiments of these embodiments, Z and X are independently selected from the group consisting of

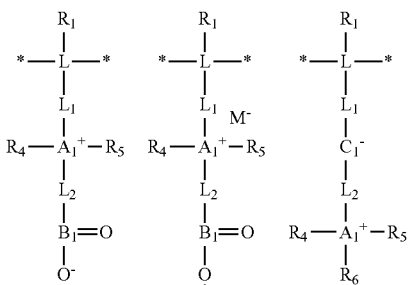

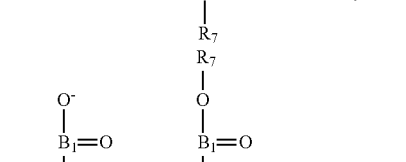

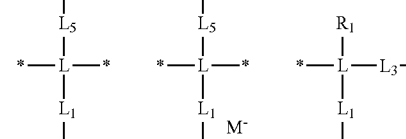

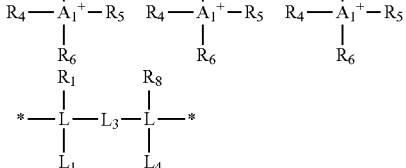

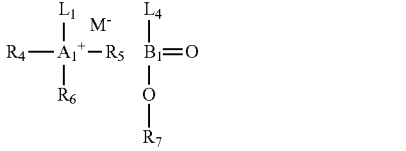 and

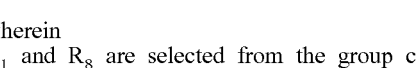

wherein $R_1$ and $R_8$ are selected from the group consisting of hydrogen, fluorine, trifluoromethyl, C1-C20 alkyl, and C6-C12 aryl groups, CN;

$R_4$, $R_5$, $R_6$, and $R_7$ are independently selected from the group consisting of hydrogen, C1-C20 alkyl, C6-C12 aryl, cyclic alkyl, fluoroalkyl, or void;

L is C or Si or void;

$L_1$, $L_3$, $L_4$, and $L_5$ are independently selected from $-(CH_2)_x-$, $-(CH(CN))_x-$, $-C(=O)NH(CH_2)_x-$, $-C(=O)O(CH_2)_x-$, $-C(=O)OC(=O)O(CH_2)_x-$, $-(CH_2)_x-O-(CH_2)_x-$, and $-(CH_2)_x-S-S-(CH_2)_x-$, where x at each occurrence is an integer independently selected from 0 to 20, combinations thereof, or void;

$L_2$ is independently selected from $-(CH_2)_x-$, or $-(CH(CN))_x-$, where x is an integer from 1 to 20;

$A_1$ is N;

$B_1$ is C, S, SO, PO, or $PO_2-$;

$B_2$ is C or SO;

$C_1$ is $PO_4$; and

M is selected from Cl, Br, I, $SO_4$, $NO_3$, $ClO_4$, $BF_4$, $PF_6$, $N(SO_2CF_3)_2$, $SO_3CF_3$, RCOO (R is C1-C20 alkyl), lactate, benzoate, salicylate, or void.

In certain embodiments, the polymer has a formula selected from the group consisting of:

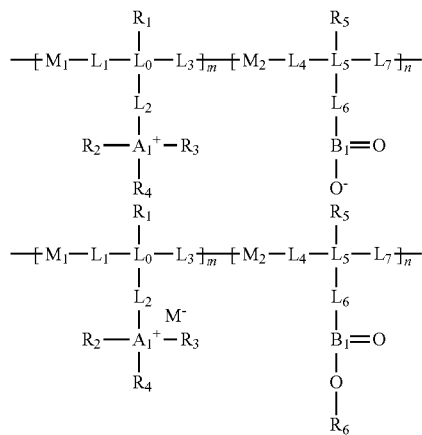

wherein $R_1$ and $R_5$ is selected from the group consisting of hydrogen, fluorine, trifluoromethyl, $C_1$-$C_{20}$ alkyl, and $C_6$-$C_{12}$ aryl groups, CN;

$R_2$, $R_3$, $R_4$, and $R_6$ are independently selected from the group consisting of hydrogen, $C_1$-$C_{20}$ alkyl, $C_6$-$C_{12}$ aryl, cyclic alkyl, fluoroalkyl, or void;

$L_0$ and $L_5$ are independently C or Si or void;

$L_1$, $L_2$, $L_3$, $L_4$, $L_6$, and $L_7$ are independently selected from $-(CH_2)_x-$, $-(CH(CN))_x-C(=O)NH(CH_2)_x-$, $-C(=O)O(CH_2)_x-$, $-C(=O)OC(=O)O(CH_2)_x-$, $-(CH_2)_x-O-(CH_2)_x-$, and $-(CH_2)_x-S-S-(CH_2)_x-$, where x at each occurrence is an integer independently selected from 0 to 20, combinations thereof, or void;

$M_1$ and $M_2$ are independently selected from the group consisting of $-O-(CH_2)_n-$, $-S-(CH_2)_n-$, $-C(=O)-(CH_2)_n-$, $-C(=S)-(CH_2)_n-$, $-C(=NH)-(CH_2)_n-$ and $-NH-(CH_2)_n-$, wherein n is an integer from 1 to 20; $-(CH_2)_x-$, $-(CH(CN))_x-$, $-C(=O)NH(CH_2)_x-$, $-C(=O)O(CH_2)_x-$, $-C(=O)OC(=O)O(CH_2)_x-$, $-(CH_2)_x-O-(CH_2)_x-$, and $-(CH_2)_x-S-S-(CH_2)_x-$, where x at each occurrence is an integer independently selected from 0 to 20, combinations thereof, or void;

$B_1$ is C, S, SO, P, or PO;

$B_2$ is C or SO;

$A_1$ is N, S, or P;

M is selected from Cl, Br, I, $SO_4$, $NO_3ClO_4$, $BF_4$, $PF_6$, $N(SO_2CF_3)_2$, $SO_3CF_3$, RCOO (R is $C_1$-$C_{20}$ alkyl), lactate, benzoate, salicylate, or void;

wherein the ratio between m and n is selected from 0.8 to 1.2; and wherein m and n are independently integers from 1 to about 10,000.

In certain embodiments, the polymers and bulk materials of the invention have a fibrinogen binding level of less than 30 ng/cm² in a fibrinogen binding assay (polymer surface is incubated at 37° C. for 90 minutes with a 1.0 mg/mL fibrinogen solution in 0.15 M phosphate buffered saline at pH 7.4).

In certain embodiments, the polymers and bulk materials of the invention have a tensile or compressive strength greater than 0.5 MPa.

In certain embodiments, the polymers and bulk materials of the invention have a fibrinogen binding level of less than 30 ng/cm² in a fibrinogen binding assay (polymer surface is incubated at 37° C. for 90 minutes with a 1.0 mg/mL fibrinogen solution in 0.15 M phosphate buffered saline at pH 7.4) and a tensile or compressive strengths greater than 0.5 MPa.

In certain embodiments, the polymers and bulk materials of the invention are crosslinked.

In a further aspect, the invention provides composite that include the polymers and bulk materials of the invention.

In one embodiment, the composite comprises a polymer of the invention and a second polymer. Suitable second polymers include polyesters, polycarbonates, polyurethanes, polyureas, polysulfides, polysulfones, polyimides, polyepoxies, aromatic polyesters, cellulosics, fluoropolymers, polyacrylics, polyamides, polyanhydrides, polyethers, vinyl polymers, phenolics, elastomers, and other addition polymers.

In certain embodiments, the composite further includes a strength additive. Representative strength additives include fibers, clays, nanotubes, and other inorganic objects.

In certain embodiments, the polymers or bulk materials of the invention are formed into an object by a method selected from the group consisting of injection molding, blow molding, extrusion molding, calendaring molding, flow casting, compression molding, prevarication molding, and 3D printing.

In another aspect, the invention provides a surface coating for a substrate that includes a polymer or bulk material of the invention. In certain embodiments, the substrate is a consumer product. In other embodiments, the substrate is a marine product.

Representative marine products include marine vessel hulls, marine structures, bridges, propellers, heat exchangers, periscopes, sensors, fish nets, cables, tubes/pipes, containers, membranes, and oil booms. In further embodiments, the substrate is a biomedical product. Representative biomedical products include catheters, ear drainage tubes, feeding tubes, glaucoma drainage tubes, hydrocephalous shunts, keratoprosthesis, nerve guidance tubes, tissue adhesives, x-ray guides, artificial joints, artificial heart valves, artificial blood vessels, pacemakers, left ventricular assist devices (LVAD), artery grafts, vascular grafts, stents, intravascular stents, cardiac valves, joint replacements, blood vessel prostheses, skin repair devices, cochlear replacements, contact lenses, artificial ligaments and tendons, dental implants, and tissue scaffolds for regenerative tissue engineering. In certain other embodiments, the substrate is a delivery vehicle selected from the group consisting of a drug delivery vehicle, a gene delivery vehicle, an RNA delivery vehicle, a protein delivery vehicle.

In a further aspect, the invention provides conjugate polymers and bulk materials where the polymer or bulk material is coupled (e.g., covalently) to a biomolecule. Representative biomolecules include therapeutic agents, nucleic acids (e.g., gene or DNA or RNA), proteins (e.g., antibody or functional fragment thereof), lipids, peptides, or small molecules having a molecular weight less than about 800.

In certain embodiments, the polymer or bulk material is coupled (e.g., covalently) to a cell or microorganism.

In other embodiments, the polymer or bulk material is coupled (e.g., covalently) to a nanoparticle. Representative nanoparticles include liposomes and micelles, quantum dots, and iron oxide, silica, or gold nanoparticles.

DESCRIPTION OF THE DRAWINGS

The foregoing aspects and many of the attendant advantages of this invention will become more readily appreciated as the same become better understood by reference to the following detailed description, when taken in conjunction with the accompanying drawings.

FIG. 3 illustrates compressive test data for a free-standing, non-fouling polymer of the present technology (PTCBEE-1.0) after hydrolysis.

FIG. 8 illustrates tensile test data for PTCBIBE-2.0 after hydrolysis.

DETAILED DESCRIPTION OF THE INVENTION

Figure 1:
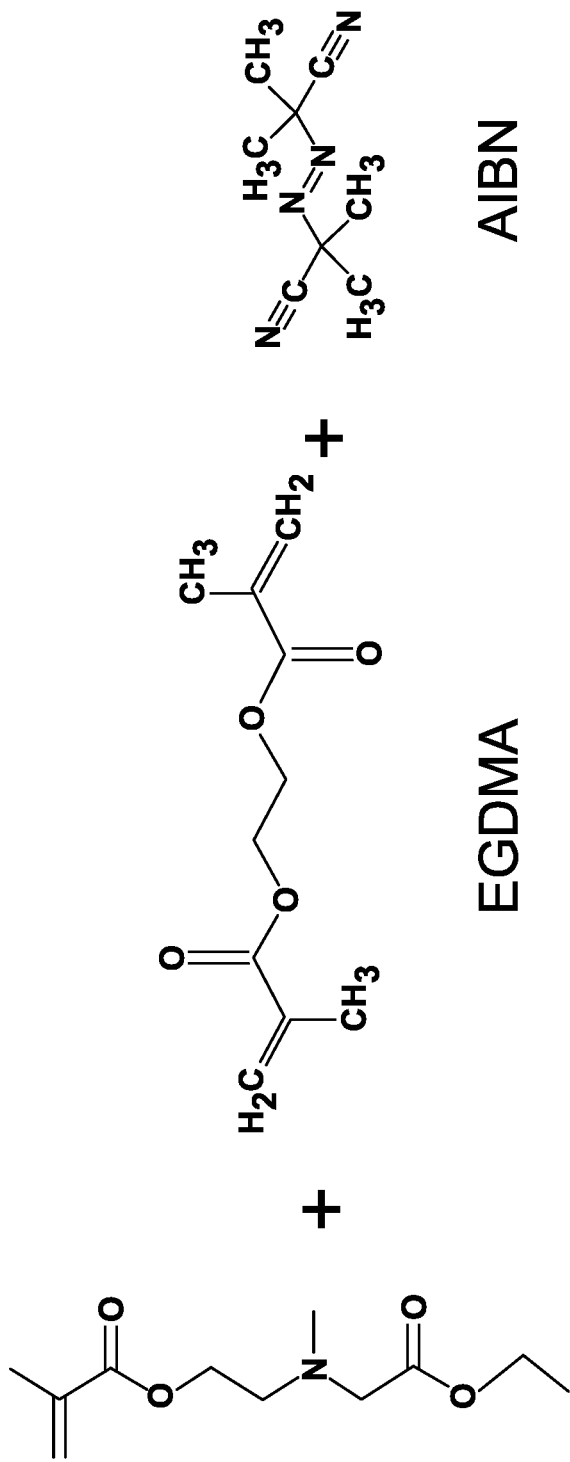
FIG. 1 illustrates the chemical structures of components of an exemplary embodiment of in-situ crosslinked polymer of the invention (PTCBEE) and compression test data before hydrolysis.

The present invention provides polymeric materials having both excellent non-fouling properties and high mechanical strength. In certain aspects, the invention provides free-standing non-fouling zwitterionic and mixed charge bulk polymeric materials having a zwitterionic and/or zwitterionic precursor content greater than or equal to about 50 weight % and having fibrinogen binding level less than about 30 ng/cm$^2$ and tensile/compressive strengths greater than about 0.5 MPa.

The polymers of the invention are prepared by polymerization of monomers. In certain embodiments, each of the monomers (or comonomers) used in the polymerization or copolymerization includes a zwitterionic group (or a latent zwitterionic group, also referred to herein as a zwitterionic precursor). In these embodiments, the product polymer has a zwitterionic and/or zwitterionic precursor content of 100 weight %. It will be appreciated that in certain instances the polymerization process includes an initiator and that the final polymer product will include components in addition to repeating units derived from the monomers. In these instances, the product polymer will have a zwitterionic and/or zwitterionic precursor content of less than 100 weight %, even though only zwitterionic and/or zwitterionic precursor monomers are used. Thus, in certain embodiments, weight % refers to weight % of the repeating units derived from the monomers used in the polymerization. In other embodiments, only a portion of the monomers used in the polymerization or copolymerization includes a zwitterionic group (or latent zwitterionic group). In these embodiments, the product polymer has a zwitterionic and/or zwitterionic precursor content less than 100 weight %. When 50 weight % of the monomers (or comonomers) used in the polymerization or copolymerization includes a zwitterionic group (or latent zwitterionic group), the product polymer has a zwitterionic and/or zwitterionic precursor content of 50 weight %. The polymers of the invention are substantially non-fouling (e.g., fibrinogen binding level less than about 30 ng/cm$^2$) due to their zwitterionic or zwitterionic precursor content at least about 50 weight %.

In certain embodiments, the polymers and materials of the invention have a zwitterionic and/or zwitterionic precursor content greater than or equal to about 50 weight %, greater than or equal to about 60 weight %, greater than or equal to about 70 weight %, greater than or equal to about 80 weight %, or greater than or equal to about 90 weight %, and in some embodiments about 100 weight %.

As used herein, the term "mixed charge" refers to monomer pairs, polymers, and materials of the invention that bear substantially equal numbers of positive and negatively charged groups (and/or latent positively or latent negatively charged groups) derived from more than a single monomer (e.g., a first monomer having a positive charge and a second monomer having a negative charge). Mixed charge monomers, precursors, polymers, and materials are considered to be zwitterionic groups. Due to their substantially equal number of positively charged groups and negatively charged groups, mixed charge polymers and materials of the invention are substantially electronically neutral and as non-fouling as their zwitterionic counterparts.

In one aspect, the present disclosure provides non-fouling zwitterionic/mixed charge bulk materials having a fibrinogen adsorption of less than about 30 ng/cm$^2$ in a fibrinogen binding assay when the material is incubated at 37 degrees C. for 90 minutes with a 1.0 mg/ml fibrinogen solution (0.15 M phosphate buffered saline at pH 7.4), and having tensile/compressive strength greater than about 0.5 MPa.

In certain embodiments, the polymers and materials of the present disclosure have fibrinogen adsorption less than about 20 ng/cm$^2$, less than about 10 ng/cm$^2$, less than about 5 ng/cm$^2$, or less than about 0.3 ng/cm$^2$, and where the tensile/compressive strength is greater than about 0.75 MPa, greater than about 1 MPa, greater than about 2 MPa, or greater than about 5 MPa. In certain of these embodiments, the polymers and materials of the invention have a zwitterionic or zwitterionic precursor content greater than or equal to about 50 weight %, greater than or equal to about 60 weight %, greater than or equal to about 70 weight %, greater than or equal to about 80 weight %, or greater than or equal to 90 weight %, and in some embodiments about 100 weight %.

In certain aspects, the non-fouling zwitterionic/mixed charge bulk materials of the invention are free-standing, non-fouling polymers.

As used herein, the terms "free-standing" and "stand-alone", which may be used interchangeably, refer to an object (i.e., polymeric composition) that is able to hold its shape without the need for a substrate or surface. In certain embodiments, the free-standing polymer of the present invention is connected, attached, or otherwise coupled to a surface or other object. However, the presence of the surface or other object is not required for the free-standing polymer to maintain the polymer's structural integrity.

In certain embodiments, the polymers according to the present technology include copolymers, including block copolymers, random copolymers, and the like (e.g., alternating polymers, homopolymers, star polymers, branched and hyperbranched polymers).

In certain embodiments, the copolymers of the present disclosure include polyesters, polycarbonates, polyurethanes, polyureas, polysulfides, polysulfones, polyimides, polyepoxies, aromatic polyesters, cellulosics, fluoropolymers, polyacrylics, polyamides, polyanhydrides, polyethers, vinyl polymers, phenolics, elastomers and other addition polymers in addition to the non-fouling polymers of the present technology.

As used herein, the term "copolymer" refers to a polymer that is the result of polymerization of two or more different monomers. The number and the nature of each constitutional unit can be separately controlled in a copolymer. The constitutional units can be disposed in a purely random, an alternating random, a regular alternating, a regular block, or a random block configuration unless expressly stated to be otherwise. A purely random configuration can, for example, be: x-x-y-z-x-y-y-z-y-z-z-z . . . or y-z-x-y-z-y-z-x-x . . . . An alternating random configuration can be: x-y-x-z-y-x-y-z-y-x-z . . . , and a regular alternating configuration can be: x-y-z-x-y-z-x-y-z . . . . A regular block configuration has the following general configuration: . . . x-x-x-y-y-y-z-z-z-x-x-x . . . , while a random block configuration has the general configuration: . . . x-x-x-z-z-x-x-y-y-y-y-z-z-z-x-x-z-z-z- . . . .

As used herein, the term "block copolymers" refers to a polymer formed of two or more covalently joined segments of polymers.

In certain embodiments, the free-standing, non-fouling polymer is a crosslinked polymer. As used herein, the term "crosslink" refers to a constitutional unit connecting two parts of a macromolecule. In certain preferred embodiments, the crosslink comprises or consists of or is derived from ethylene glycol dimethacrylate crosslinker (EGDMA).

In certain embodiments, such free-standing, non-fouling polymers and monomers comprise zwitterionic and/or mixed charge repeating units, as described further herein. As used herein, "mixed charge" refers to polymers comprising both positive or latent positive and negative or latent negative charges in substantially equal proportions. Such polymers are described in, for example, PCT application no. PCT/US2007/075409, which is incorporated herein by reference in its entirety.

In certain embodiments, the zwitterionic repeating units are selected from carboxybetaines (CB), sulfobetaines (SB), phosphobetaines (PHB) and other zwitterionic compounds such as phosphorylcholine (PC) as well as their protected (latent) versions.

Generally, the zwitterionic repeating units comprise a cationic center and an anionic center. In addition to zwitterionic moieties, non-fouling moieties can be acrylamide, oxazoline, vinylpyrrolidone, PEG or polysaccharide. In certain embodiments, the cationic centers within the zwitterionic moieties are selected from quaternary, tertiary and secondary ammonium, imidazolium, triazolium, pyridinium, morpholinium and other cationic monomers or combinations thereof. The anionic moieties can be selected from hydrophilic and/or hydrophobic anions, their mixtures, or modified hydrophilic and/or hydrophobic anions thereof.

In certain embodiments, the free-standing, non-fouling polymers of the present disclosure comprise crosslinks that increase the compressive and/or tensile strength of the polymers. Such crosslinks can be hydrophilic or hydrophobic.

In certain further embodiments, the free-standing, non-fouling polymers of the present disclosure are reinforced with material to increase their compressive and/or tensile strengths. Such material can include, for example, fibers, silk, nylon, polymer meshes, springs, clays, and nanotubes.

The free-standing, non-fouling polymers of the present disclosure can be made by free radical, living radical or condensation/addition polymerization reactions.

Because the free-standing, non-fouling polymers of the present disclosure do not require a surface for support they can be easily and effectively cast, extruded, molded, blow-molded, calendar molded, flow cast, compression molded, prevarication molded, 3d-printed or otherwise formed according to industry standard methods for forming polymer objects and devices.

Such objects, devices, and components can include without limitation implantable biosensors; wound care devices, including glues and sealants; cardiovascular devices such as catheters, stents, artificial blood vessels, artificial valves, LVADs, or implanted cardiac rhythm management devices; gastroenterology devices such as feeding tubes, alimentary canal clips, gastro-intestinal sleeves, or gastric balloons; OB/Gyn devices such as implantable birth control devices or vaginal slings; nephrology devices such as anastomotic connectors or subdermal ports; neurosurgery devices such as nerve guidance tubes, cerebrospinal fluid drains or shunts, dermatology devices such as skin repair devices; opthalmic devices such as contact lenses, artificial lenses, keratoprostheses, or intraocular shunts; orthopedic devices such as artificial joints, tendons, or ligaments, oral and maxillofacial surgical devices such as artificial cartilage for implanted use; dental implants; surgical fillers; otorhinolaryngology devices such as stents, cochlear implants, tubes, shunts or spreaders; hepatology devices such as stents or shunts; plastic/reconstructive/aesthetic devices such as breast implants, injectable fillers, tissue scaffolds or other structural implants; pulmonic devices such as valves for management of COPD or artificial lungs; radiology devices such as radio-opaque or sono-opaque markers; or urology devices such as catheters or artificial urethrae. The materials may also be used as injectable or implantable medical devices for the delivery of drugs or biomaterial such as cellular components such as genes, proteins, or other biological molecules, or cells such as stem cells, T-cells, B-cells, or islet cells.

The present disclosure also provides therapeutic and diagnostic devices comprising the free-standing, non-fouling polymers of the present technology. These include without limitation particles comprising the standing, non-fouling polymers of the present technology useful for, but are not limited to, particles for the delivery of drugs, genes, RNAs and proteins and diagnostics.

The present disclosure also provides marine devices comprising the free-standing, non-fouling polymers of the present technology. Such marine devices include, for example, marine vessel hull, marine structures, bridge, propeller, periscope, sensor, oil boom, fish net, cables, tubes/pipes, containers, or plates.

The present disclosure also provides membranes comprising the free-standing, non-fouling polymers of the present technology, useful in separation, purification, filtration or desalination.

Representative Free-Standing Zwitterionic Polymers and Copolymers

In one embodiment, the invention provides a free-standing, zwitterionic copolymer prepared from a zwitterionic monomer and a stabilizing monomer that includes a moiety capable of generating dipole-dipole interactions or hydrogen bonding. Free-standing zwitterionic copolymers include zwitterionic and a stabilizing repeating units. In this embodiment, the stabilizing group can be a part of the polymer backbone.

In another embodiment, the invention provides a free-standing, zwitterionic polymer prepared from a zwitterionic monomer that includes a stabilizing moiety capable of generating dipole-dipole interactions or hydrogen bonding. Free-standing zwitterionic polymers include repeating units that include zwitterionic and stabilizing groups. In this embodiment, the stabilizing group can be a part of the pendant group coupled to the polymer backbone.

Representative copolymers and polymers according to these embodiments include copolymers/homopolymers according to the following formulae:

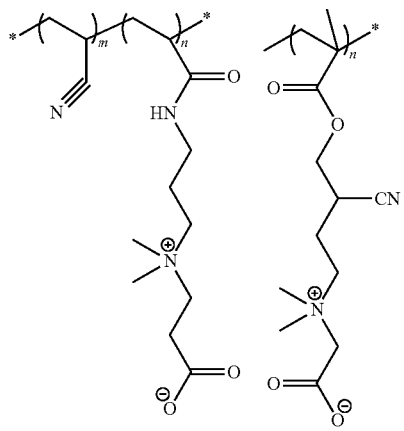

wherein m and are independently integers from 1 to about 10,000. In these polymers, the cyano moiety is the stabilizing moiety.

Zwitterionic Monomers for Condensation/Addition Polymerization

In another aspect, the present disclosure provides monomers useful in the synthesis of free-standing, non-fouling zwitterionic and mixed charge polymers via condensation/addition polymerization. The polymers based on such monomers can be linear or crosslinked polymers. Materials containing these polymers (homopolymers, copolymers, or composites) can be prepared as free-standing devices, objects, or particles with both non-fouling and high strength. Such polymers can be free-standing and do not require that they be grafted to or from a surface. Further such polymers are useful in a broad range of biomedical/biotechnological, consumer product, engineering/marine and therapeutics/diagnostics applications. In certain embodiments, the polymers of the present technology can also be used as surface coatings.

The present disclosure provides polymerizable zwitterionic monomers useful in, for example, the synthesis of macrodiols and macrodiamines. Such monomers are, in turn, useful in the synthesis of non-fouling zwitterionic polymers via condensation/addition polymerization.

In certain embodiments, the zwitterionic monomers comprise zwitterionic moieties selected from carboxybetaines (CB), sulfobetaines (SB), phosphobetaines (PHB), and phosphorylcholine (PC).

In certain embodiments, the monomers of the present disclosure are useful in making polymers selected from polyesters, polycarbonates, polyurethanes, polyureas, polysulfides, polysulfones, polyimides, polyepoxides, polyamides, polyanhydrides, polyethers through condensation/addition reactions.

In certain embodiments, the zwitterionic monomers of the present technology comprise a cationic center selected from the group comprising a quaternary, tertiary and secondary ammonium, imidazolium, triazolium, pyridinium, and morpholinium.

In certain embodiments, the monomer of the invention is a bifunctional monomer having a first and a second functional group that allow for the monomer to be incorporated into a polymer by reaction through the first and second groups by, for example, condensation and addition polymerization methods with suitable condensation and addition comonomers, respectively. In these methods, the first and second functional groups may be the same or different, and serve as the point at which the monomer is incorporated into the condensation or addition polymer. For condensation polymerization, the first and second functional groups form covalent bonds with suitable condensation comonomers. For addition polymerization, the first and second functional groups form covalent bonds with suitable addition comonomers. The nature of the first and second functional groups of the monomers of the invention is not critical. Suitable first and second functional groups include those known in the art (e.g., Michael addition groups, click chemistry groups, lactones for ring opening polymerization). Representative monomers having first and second functional groups are described below. For the monomers of the invention having first and second functional groups, the first and second functional groups are defined as $R_2$ and $R_3$ in the chemical structures of these monomers.

In the following description of the monomers, macromonomers, and polymers, the term "void" refers to embodiments where the specified substituent or specified group is absent from that embodiment (i.e., void (when substituent or group is absent)).

Therefore, as used herein, the term "void" in the context of a specified substituent or specified group means that in the "void" embodiment, the specified substituent or specified group is absent.

In certain embodiments, the polymerizable zwitterionic monomers according to the present technology have one of the following the formulae:

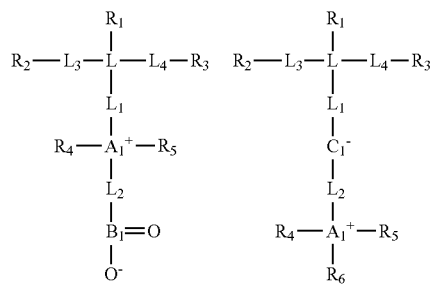

-continued

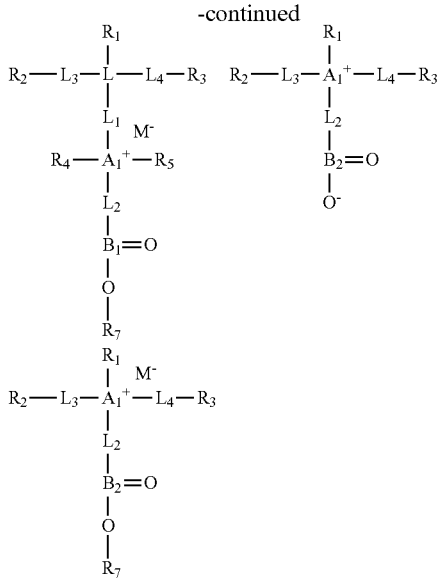

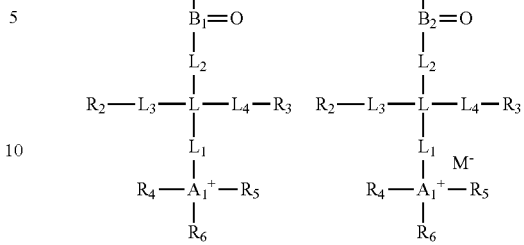

wherein $R_1$ is selected from the group consisting of hydrogen fluorine, trifluoromethyl, $C_1$-$C_{20}$ alkyl, and $C_6$-$C_{12}$ aryl groups, CN;

$R_4$, $R_5$, $R_6$, and $R_7$ are independently selected from the group consisting of hydrogen, $C_1$-$C_{20}$ alkyl, and $C_1$-$C_{12}$ aryl, cyclic alkyl (e.g., isobornyl, cyclohexyl, cyclopentyl), fluoroalkyl (e.g., perfluorobutyl, perfluoroethyl), or void;

$R_2$ and $R_3$ are independently selected from F, C, Br, I, SH, protected thiols, $NH_2$, —NH— (secondary amine), N=C=O, protected NCO, N=C=S, COOH, COSH, C(=S)SH, OCOOH, OCOSH, OC(=S)OH, SC(=O)SH, SC(=S)SH, N(C=O)$NH_2$, N(C=NH)$NH_3$—, N(C=S)$NH_2$, δ-valerolactone moiety, ε-caprolactone moiety, $CH_2$=CH—C(=O)—O—, $CH_2$=CH—C(=O)—NH, $CH_2$CH—C(=O)—S—, CN, $CH_2$=CH($CH_3$)—C(=O)—O—, $CH_2$=CH($CH_3$)—C(=O)—O—, OH, azides, alkynes, or void;

L is C or Si or void;

$L_1$, $L_3$, and $L_4$ are independently selected from —($CH_2$)$_x$—, —(CH(CN))$_x$—, —C(=O)NH($CH_2$)$_x$—, —C(=O)O($CH_2$)$_x$—, —C(=O)OC(=O)O($CH_2$)$_x$—, —($CH_2$)$_x$—O—($CH_2$)$_x$— and —($CH_2$)$_x$—S—S—($CH_2$)$_x$—, where x at each occurrence is an integer independently selected from 0 to 20, combinations thereof, or void;

$L_2$ is independently selected from —($CH_2$)$_x$—, or —($CH_2$)$_x$—, or —(CH(CN))$_x$—, where x is an integer from 1 to 20;

$A_1$ is N;

$B_1$ is C, S, SO, PO, or $PO_2$—;

$B_2$ is C or SO;

$C_1$ is $PO_4$; and

M is selected from Cl, Br, I, $SO_4$, $NO_3ClO_4$, $BF_4$, $PF_6$, N($SO_2CF_3$)$_2$, $SO_3CF_3$, RCOO (R is $C_1$-$C_{20}$ alkyl), lactate, benzoate, and salicylate or void.

In further embodiments, the zwitterionic monomers according to the present technology have one of the following the formulae:

wherein $R_2$ and $R_3$ are independently selected from F, Cl, Br, I, SH, protected thiols, $NH_2$, —NH— (secondary amine), N=C=O, N=C=S, COOH, COSH, C(=S)SH, OCOOH, OCOSH, OC(=S)OH, SC(=O)SH, SC(=S)SH, N(C=O)$NH_2$, N(C=NH)$NH_2$, N(C=S)$NH_2$, δ-valerolactone moiety, ε-caprolactone moiety, $CH_2$=CH—C(=O)—O—, $CH_2$=CH—C(=O)—NH—, $CH_2$=CH—C(=O)S—, CN, $CH_2$=CH($CH_3$)—C(=O)—O—, $CH_2$=CH($CH_3$)—C(=O)—O—, OH, azides, alkynes, or void;

$R_4$, $R_5$, $R_6$, and $R_7$ are independently selected from the group consisting of hydrogen, $C_1$-$C_{20}$ alkyl, $C_6$-$C_{12}$ aryl, cyclic alkyl groups (e.g., isobornyl, cyclohexyl, cyclopentyl), fluoroalkyl (e.g., perfluorobutyl, perfluoroethyl), or void;

L is C or Si or void;

$L_1$, $L_2$, $L_3$, and $L_4$ are independently selected from —($CH_2$)$_x$—, —(CH(CN))$_x$—, —C(=O)NH($CH_2$)$_x$—, —C(=O)O($CH_2$)$_x$—, —C(=O)OC(=O)O($CH_2$)$_x$—, —($CH_2$)$_x$—O—($CH_2$)$_x$—, and —($CH_2$)$_x$—S—S—($CH_2$)$_x$—, where x at each occurrence is an integer independently selected from 0 to 20, combinations thereof, or void;

$A_1$ is N;

$B_1$ is C, S, SO, PO, or $PO_2$;

$B_2$ is C or SO;

$C_1$ is $PO_4$; and

M is selected from Cl, Br, I, $SO_4$, $NO_3ClO_4$, $BF_4$, $PF_6$, N($SO_2CF_3$)$_2$, $SO_3CF_3$, RCOO (R is $C_1$-$C_{20}$ alkyl), lactate, benzoate, and salicylate or void.

In further embodiments, the zwitterionic monomers according to the present technology have one of the following the formulas:

wherein $R_1$ and $R_6$ is selected from the group consisting of hydrogen, fluorine, trifluoromethyl, $C_1$-$C_{20}$ alkyl, $C_6$-$C_{12}$ aryl, CN, cyclic alkyl (e.g., isobornyl, cyclohexyl, cyclopentyl), fluoroalkyl (e.g., perfluorobutyl, perfluoroethyl), or void;

$R_4$, $R_5$, $R_7$, and $R_8$ are independently selected from the group consisting of hydrogen, $C_1$-$C_{20}$ alkyl, $C_6$-$C_{12}$ aryl, cyclic alkyl group (e.g., isobornyl, cyclohexyl, cyclopentyl), fluoroalkyl (e.g., perfluorobutyl, perfluoroethyl), or void;

$R_2$ and $R_3$ are independently selected from F, Cl, Br, I, SH, protected thiols, $NH_2$, —NH— (secondary amine), N=C=O, N=C=S, COOH, COSH, C(=S)SH, OCOOH, OCOSH, OC(=S)OH, SC(=O)SH, SC(=S)SH, N(C=O)$NH_2$, N(C=NH)$NH_2$, N(C=S)$NH_2$, δ-valerolactone moiety, ε-caprolactone moiety, $CH_2$=CH—C(=O)—O—, $CH_2$=CH—C(=O)—NH—, $CH_2$=CH—C(=O)—S—, CN, $CH_2$=CH($CH_3$)—C(=O)—O—, $CH_2$=CH($CH_3$)—C(=O)—O—, OH, azides, alkynes, or void;

$L_0$ and $L_4$ are C or Si or void;

$L_1$, $L_2$, $L_3$, $L_5$, and $L_6$ are independently selected from —$(CH_2)_x$—, —$(CH(CN))_x$—, —C(=O)NH$(CH_2)_x$—, —C(=O)O$(CH_2)_x$—, —C(=O)OC(=O)O$(CH_2)_x$—, —$(CH_2)_x$—O—$(CH_2)_x$—, and —$(CH_2)_x$—S—S—$(CH_2)_x$—, where x at each occurrence is an integer independently selected from 0 to 20, combinations thereof, or void;

$A_1$ is N;

$B_1$ is C, S, SO, PO, or $PO_2$;

$B_2$ is C or SO;

$C_1$ is $PO_4$; and

M is selected from Cl, Br, I, $SO_4$, $NO_3ClO_4$, $BF_4$, $PF_6$, $N(SO_2CF_3)_2$, $SO_3CF_3$, RCOO (R is $C_1$-$C_{20}$ alkyl), lactate, benzoate, and salicylate, or void.

Macromonomers

The present disclosure further provides macromonomers having one of the following formulae:

wherein $R_1$ is selected from the group consisting of hydrogen, fluorine, trifluoromethyl, $C_1$-$C_{20}$ alkyl, $C_6$-$C_{12}$ aryl, CN;

$R_4$, $R_5$, $R_6$, and $R_7$ are independently selected from the group consisting of hydrogen, $C_1$-$C_{20}$ alkyl, $C_6$-$C_{12}$ aryl, cyclic alkyl (e.g., isobornyl, cyclohexyl, cyclopentyl), fluoroalkyl (e.g., perfluorobutyl, perfluoroethyl), or void;

$R_2$ and $R_3$ are independently selected from F, Cl, Br, I, SH, protected thiols, $NH_2$, —NH— (secondary amine), N=C=O, N=C=S, COOH, COSH, C(=S)SH, OCOOH, OCOSH, OC(=S)OH, SC(=O)SH, SC(=S)SH, N(C=O)$NH_2$, N(C=NH)$NH_2$, N(C=S)$NH_2$, δ-valerolactone moiety, ε-caprolactone moiety, $CH_2$=CH—C(=O)—O—, $CH_2$=CH—C(=O)—NH—, $CH_2$=CH—C(=O)S—, CN, $CH_2$=CH($CH_3$)—C(=O)—O—, $CH_2$=CH($CH_3$)—C(=O)—O—, OH, azides, alkynes, or void;

L is C or Si or void;

$L_1$, $L_3$, and $L_4$ are independently selected from —$(CH_2)_x$—, —$(CH(CN))_x$—, —C(=O)NH$(CH_2)_x$—, —C(=O)O$(CH_2)_x$—, —C(=O)OC(=O)O$(CH_2)_x$—, —$(CH_2)_x$—O—$(CH_2)_x$—, and —$(CH_2)_x$—S—S—$(CH_2)_x$—, where x at each occurrence is an integer independently selected from 0 to 20, combinations thereof, or void;

$L_2$ is independently selected from —$(CH_2)_x$—, or —$(CH(CN))_x$—, where x is an integer from 1 to 20;

$A_1$ is N;

$B_1$ is C, S, SO, PO, or $PO_2$;

$B_2$ is C or SO;

$C_1$ is $PO_4$;

M is selected from Cl, Br, I, $SO_4$, $NO_3ClO_4$, $BF_4$, $PF_6$, $N(SO_2CF_3)_2$, $SO_3CF_3$, RCOO (R is $C_1$-$C_{20}$ alkyl), lactate, benzoate, and salicylate or void; and j is an integer from 1 to about 1000.

In further embodiments, the zwitterionic monomers according to the present technology have one of the following formulae:

wherein $R_4$, $R_5$, $R_6$, and $R_7$ are independently selected from the group consisting of hydrogen, $C_1$-$C_{20}$ alkyl, $C_6$-$C_{12}$ aryl, cyclic alkyl (e.g., isobornyl, cyclohexyl, cyclopentyl), fluoroalkyl (e.g., perfluorobutyl, perfluoroethyl), or void;

$R_2$ and $R_3$ are independently selected from F, Cl, Br, I, SH, protected thiols, $NH_2$, —NH— (secondary amine), N=C=O, N=C=S, COOH, COSH, C(=S)SH, OCOOH, OCOSH, OC(=S)OH, SC(=O)SH, SC(=S)SH, N(C=O)$NH_2$, N(C=NH)$NH_2$, N(C=S)$NH_2$, δ-valerolactone moiety, ε-caprolactone moiety, $CH_2$=CH—C(=O)—O—, $CH_2$=CH—C(=O)—NH—, $CH_2$=CH—C(=O)S—, CN, $CH_2$=CH($CH_3$)—C(=O)—O—, $CH_2$=CH($CH_3$)—C(=O)—O—, OH, azides, alkynes, or void;

L is C or Si or void;

$L_1$, $L_3$, and $L_4$ are independently selected from —$(CH_2)_x$—, —$(CH(CN))_x$—, —C(=O)NH$(CH_2)_x$—, —C(=O)O(CH$_2$)$_x$—, —C(=O)OC(=O)O(CH$_2$)$_x$—, —(CH$_2$)$_x$—O—(CH$_2$)$_x$—, and —(CH$_2$)$_x$—S—S—(CH$_2$)$_x$—, where x at each occurrence is an integer independently selected from 0 to 20, combinations thereof, or void;

L$_2$ is independently selected from —(CH$_2$)$_x$—, or —(CH(CN))$_x$—, where x is an integer from 1 to 20;

A$_1$ is N;

B$_1$ is C, S, SO, PO, or PO$_2$;

B$_2$ is C or SO;

M is selected from Cl, Br, I, SO$_4$, NO$_3$ClO$_4$, BF$_4$, PF$_6$, N(SO$_2$CF$_3$)$_2$, SO$_3$CF$_3$, RCOO (R is C$_1$-C$_{20}$ alkyl), lactate, benzoate, and salicylate or void; and j is an integer from 1 to about 1000.

In another embodiment, the polymerizable zwitterionic monomers of the present disclosure have one of the following the formulas:

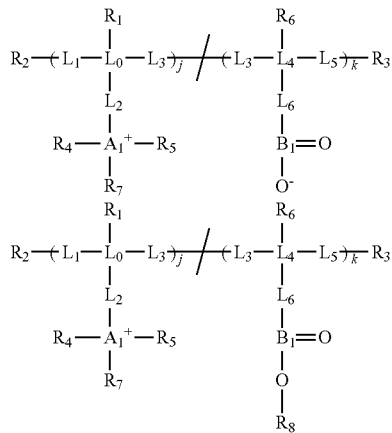

wherein

R$_1$ and R$_6$ are selected from the group consisting of hydrogen, fluorine, trifluoromethyl, C$_1$-C$_{20}$ alkyl, C$_6$-C$_{12}$ aryl, CN, cyclic alkyl (e.g., isobornyl, cyclohexyl, cyclopentyl), fluoroalkyl (e.g., perfluorobutyl, perfluoroethyl), or void;

R$_4$, R$_5$, R$_7$, and R$_8$ are independently selected from the group consisting of hydrogen, C$_1$-C$_{20}$ alkyl, C$_6$-C$_{12}$ aryl, cyclic alkyl (e.g., isobornyl, cyclohexyl, cyclopentyl), fluoroalkyl (e.g., perfluorobutyl, perfluoroethyl), or void;

R$_2$ and R$_3$ are independently selected from F, Cl, Br, I, SH, protected thiols, NH$_2$, —NH— (secondary amine), N=C=O, N=C=S, COOH, COSH, C(=S)SH, OCOOH, OCOSH, OC(=S)OH, SC(=O)SH, SC(=S)SH, N(C=O)NH$_2$, N(C=NH)NH$_2$, N(C=S)NH$_2$, δ-valerolactone, ε-caprolactone, CH$_2$=CH—C(=O)—O—, CH$_2$=CH—C(=O)—NH—, CH$_2$=CH—C(=O)—S—, CN, CH$_2$=CH(CH$_3$)—C(=O)—O—, CH$_2$=CH(CH$_3$)—C(=O)—O—, OH, azides, alkynes, or void;

L$_0$ and L$_4$ are C or Si or void;

L$_1$, L$_2$, L$_3$, L$_5$, and L$_6$ are independently selected from —(CH$_2$)$_x$—, —(CH(CN))$_x$—, —C(=O)NH(CH$_2$)$_x$—, —C(=O)O(CH$_2$)$_x$—, —C(=O)OC(=O)O(CH$_2$)$_x$—, —(CH$_2$)$_x$—O—(CH$_2$)$_x$—, and —(CH$_2$)$_x$—S—S—(CH$_2$)$_x$—, where x at each occurrence is an integer independently selected from 0 to 20, combinations thereof, or void;

A$_1$ is N;

B$_1$ is C, S, SO, PO, or PO$_2$—;

B$_2$ is C or SO;

C1 is PO$_4$;

M is selected from Cl, Br, I, SO$_4$, NO$_3$ClO$_4$, BF$_4$, PF$_6$, N(SO$_2$CF$_3$)$_2$, SO$_3$CF$_3$, RCOO (R is C$_1$-C$_{20}$ alkyl), lactate, benzoate, and salicylate or void; and j and k are integers independently selected from 1 to about 1000.

Stabilizing Monomers

As noted above, the stabilizing monomer includes moieties that are capable of generating hydrogen bonding interactions and/or moieties capable of generating dipole-dipole interactions.

In certain embodiments, the stabilizing monomer comprises moieties capable of generating hydrogen bonding interactions. In certain embodiments, the moieties capable of generating hydrogen bonding interactions are selected from the group consisting of amide group (—(NH)—(C=O)—), multiple amide groups ((—(NH)—(C=O)—)$_n$ (n=1-5)), urethane group (—(NH)—(C=O)—O—), multiple urethane groups ((—(NH)—(C=O)—O—)$_n$ (n=1-5)), urea group (—(NH)—(C=O)—(NH)—), multiple urea groups ((—(NH)—(C=O)—(NH)—)$_n$ (n=1-5)).

In other embodiments, the stabilizing monomer comprises moieties capable of generating dipole-dipole interactions. In certain embodiments, the moiety capable of generating dipole-dipole interactions is a cyano group (CN).

The moieties capable of generating dipole-dipole and hydrogen bonding interactions can be located on the backbone of the free-standing polymer itself or pendant from polymer the backbone.

Representative monomers include the following monomers:

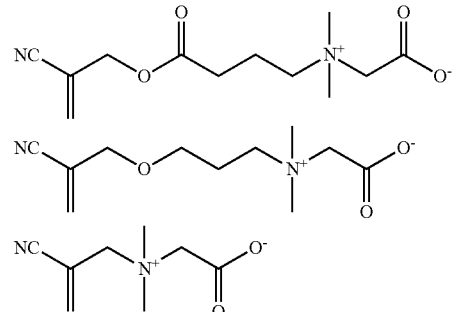

Cyano group on backbone

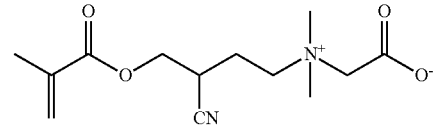

Cyano group on side chain

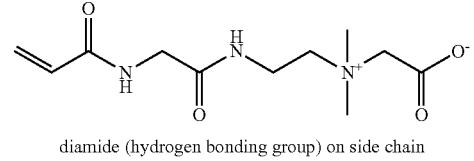

diamide (hydrogen bonding group) on side chain

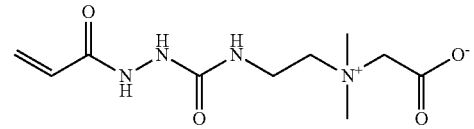

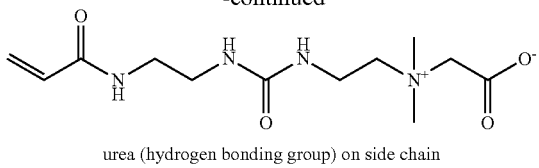

urea (hydrogen bonding group) on side chain

Free-Standing Non-Fouling Polymers

In a further aspect, the present disclosure provides free-standing non-fouling polymers. In certain embodiments, these polymers have fibrinogen binding of less than 30 ng/cm$^2$ in a fibrinogen binding assay when the surface is incubated at 37° C. for 90 minutes with a 1.0 mg/mL fibrinogen solution (0.15 M phosphate buffered saline at pH 7.4), and tensile or compressive strengths greater than 0.5 MPa.

In certain embodiments, the polymer has the formula:

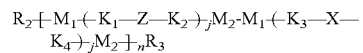

with n repeating units -$M_1$-($K_1$—Z—$K_2$)$_j$-$M_2$-$M_1$-($K_3$—X—$K_4$)$_j$-$M_2$-, which includes j repeating units —$K_1$—Z—$K_2$— and j repeating units —$K_3$—X—$K_4$—. K1, K2, K3, and K4 are linkers as defined above for L in the case of monomers, and also are the product functional groups formed by polymerization reaction between monomers.

In the above formula, $K_1$, $K_2$, $K_3$, and $K_4$ are independently selected from —$(CH_2)_x$—, —$(CH(CN))_x$—, —C(=O)NH$(CH_2)_x$—, —C(=O)O$(CH_2)_x$—, —C(=O)OC(=O)O$(CH_2)_x$—, —$(CH_2)_x$—O—$(CH_2)_x$—, and —$(CH_2)_x$—S—S—$(CH_2)_x$—, where x at each occurrence is an integer independently selected from 0 to 20, combinations thereof, or void;

$R_2$ and $R_3$ are independently selected from H, F, Cl, Br, I, OH, SH, protected thiols, NH$_2$, —NH— (secondary amine), N=C=O, N=C=S, COOH, COSH, C(=S)SH, OCOOH, OCOSH, OC(=S)OH, SC(=O)SH, SC(=S)SH, N(C=O)NH$_2$, N(C=NH)NH$_2$, N(C=S)NH$_2$, δ-valerolactone moiety, ε-caprolactone moiety, CH$_2$=CH—C(=O)—O—, CH$_2$=CH—C(=O)—NH—, CH$_2$=CH—C(=O)—S—, CN, CH$_2$=CH(CH$_3$)—C(=O)—O—, CH$_2$=CH(CH$_3$)—C(=O)—NH—, or void;

n is an integer from 5 to about 10,000;

j is an integer from 1 to about 1000;

$M_1$ and $M_2$ are independently selected from the group consisting of —O—$(CH_2)_n$—, —S—$(CH_2)_n$—, —C(=O)—$(CH_2)_n$—, —C(=S)—$(CH_2)_n$—, —C(=NH)—$(CH_2)_n$— and —NH—$(CH_2)_n$—, wherein n is an integer from 1 to 20; —$(CH_2)_x$—, —$(CH(CN))_x$—, —C(=O)NH$(CH_2)_x$—, —C(=O)O$(CH_2)_x$—, —C(=O)OC(=O)O$(CH_2)_x$—, —$(CH_2)_x$—O—$(CH_2)_x$—, and —$(CH_2)_x$—S—S—$(CH_2)_x$—, where x at each occurrence is an integer independently selected from 0 to 20, combinations thereof, or void; and Z and X are independently selected from zwitterionic groups.

In certain embodiments, the zwitterionic groups are independently selected from the group consisting of the following formulae:

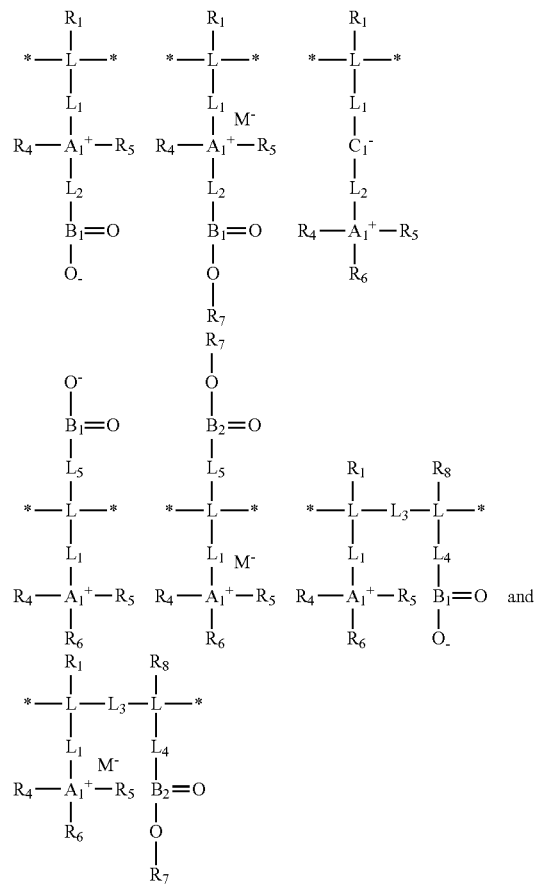

wherein $R_1$ and $R_8$ are selected from the group consisting of hydrogen, fluorine, trifluoromethyl, $C_1$-$C_{20}$ alkyl, and $C_6$-$C_{12}$ aryl groups, CN;

$R_4$, $R_5$, $R_6$, and $R_7$ are independently selected from the group consisting of hydrogen, $C_1$-$C_{20}$ alkyl, $C_6$-$C_{12}$ aryl, cyclic alkyl (e.g., isobornyl, cyclohexyl, cyclopentyl), fluoroalkyl (e.g., perfluorobutyl, perfluoroethyl), or void;

L is C or Si or void;

$L_1$, $L_3$, $L_4$, and $L_5$ are independently selected from —$(CH_2)_x$—, —$(CH(CN))_x$—, —C(=O)NH$(CH_2)_x$—, —C(=O)O$(CH_2)_x$—, —C(=O)OC(=O)O$(CH_2)_x$—, —$(CH_2)_x$—O—$(CH_2)_x$—, and —$(CH_2)_x$—S—S—$(CH_2)_x$—, where x at each occurrence is an integer independently selected from 0 to 20, combinations thereof, or void;

$L_2$ is independently selected from —$(CH_2)_x$—, or —$(CH(CN))_x$—, where x is an integer from 1 to 20;

$A_1$ is N;

$B_1$ is C, S, SO, PO, or PO$_2$—;

$B_2$ is C or SO;

$C_1$ is PO$_4$; and

M is selected from Cl, Br, I, SO$_4$, NO$_3$ClO$_4$, BF$_4$, PF$_6$, N(SO$_2$CF$_3$)$_2$, SO$_3$CF$_3$, RCOO(R is $C_1$-$C_{20}$ alkyl), lactate, benzoate, and salicylate or void.

In certain further embodiments, the polymers of the present disclosure have the formulae:

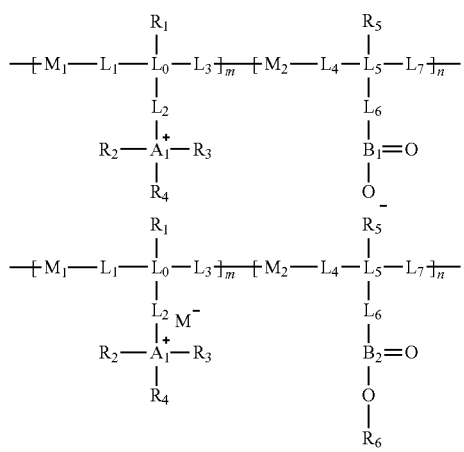

wherein $R_1$ and $R_5$ is selected from the group consisting of hydrogen, fluorine, trifluoromethyl, $C_1$-$C_{20}$ alkyl, and $C_6$-$C_{12}$ aryl groups, CN;

$R_2$, $R_3$, $R_4$, and $R_6$ are independently selected from the group consisting of hydrogen, $C_1$-$C_{20}$ alkyl, $C_6$-$C_{12}$ aryl, cyclic alkyl (e.g., isobornyl, cyclohexyl, cyclopentyl), fluoro alkyl (e.g., perfluorobutyl, perfluoroethyl), or void;

$L_0$ and $L_5$ are C or Si or void;

$L_1$, $L_2$, $L_3$, $L_4$, $L_6$, and $L_7$ are independently selected from —(CH$_2$)$_x$—, —(CH(CN))$_x$—C(=O)NH(CH$_2$)$_x$—, —C(=O)O(CH$_2$)$_x$—, —C(=O)OC(=O)O(CH$_2$)$_x$—, —(CH$_2$)$_x$—O—(CH$_2$)$_x$—, and —(CH$_2$)$_x$—S—S—(CH$_2$)$_x$—, where x at each occurrence is an integer independently selected from 0 to 20, combinations thereof, or void;

$M_1$ and $M_2$ are independently selected from the group consisting of —O—(CH$_2$)$_n$—, —S—(CH$_2$)$_n$—, —C(=O)—(CH$_2$)—, —C(=S)—(CH$_2$)—, —C(=NH)—(CH$_2$)$_n$ and —NH—(CH$_2$)$_n$—, wherein n is an integer from 1 to 20; —(CH$_2$)$_x$—, —(CH(CN))$_x$—, —C(=O)NH(CH$_2$)$_x$—, —C(=O)O(CH$_2$)$_x$—, —C(=O)OC(=O)O(CH$_2$)$_x$—, —(CH$_2$)$_x$—O—(CH$_2$)$_x$—, and —(CH$_2$)$_x$—S—S—(CH$_2$)$_x$—, where x at each occurrence is an integer independently selected from 0 to 20, combinations thereof, or void;

$B_1$ is C, S, SO, P, or PO;

$B_2$ is C or SO;

$A_1$ is N, S, P;

M is selected from Cl, Br, I, SO$_4$, NO$_3$ClO$_4$, BF$_4$, PF$_6$, N(SO$_2$CF$_3$)$_2$, SO$_3$CF$_3$, RCOO (R is $C_1$-$C_{20}$ alkyl), lactate, benzoate, and salicylate, or void;

wherein the ratio between m and n is selected from 0.8 to 1.2; and wherein m and n are independently integers from 1 to about 10,000.

Representative Free-Standing Zwitterionic Polymers and Copolymers

In one embodiment, the invention provides a free-standing, zwitterionic copolymer prepared from a zwitterionic monomer and a stabilizing monomer that includes a moiety capable of generating dipole-dipole interactions or hydrogen bonding. Free-standing zwitterionic copolymers include zwitterionic and a stabilizing repeating units. In this embodiment, the stabilizing group can be a part of the polymer backbone.

In another embodiment, the invention provides a free-standing, zwitterionic polymer prepared from a zwitterionic monomer that includes a stabilizing moiety capable of generating dipole-dipole interactions or hydrogen bonding. Free-standing zwitterionic polymers include repeating units that include zwitterionic and stabilizing groups. In this embodiment, the stabilizing group can be a part of the pendant group coupled to the polymer backbone.

Representative copolymers and polymers according to these embodiments include copolymers/homopolymers according to the following formulae:

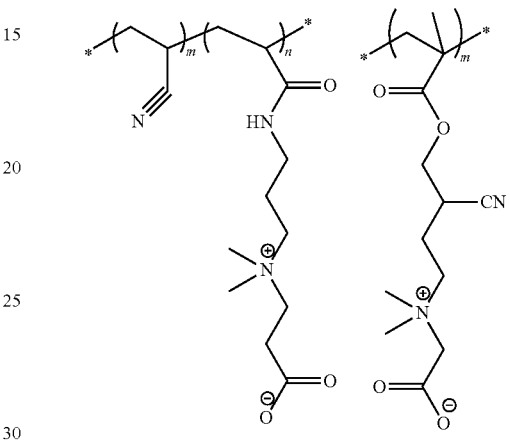

wherein m and are independently integers from 1 to about 10,000. In these polymers, the cyano moiety is the stabilizing moiety.

Representative In-Situ Hydrolyzed Robust Zwitterionic Materials

In another aspect, the present disclosure provides a crosslinked zwitterionic precursor material (after treatment of surface hydrolysis) having fibrinogen binding of less than 30 ng/cm$^2$ in a fibrinogen binding assay when the surface is incubated at 37° C. for 90 minutes with a 1.0 mg/mL fibrinogen solution (0.15 M phosphate buffered saline at pH 7.4) and tensile or compressive strengths greater than 0.5 MPa. In certain embodiments the crosslinked zwitterionic precursor material comprises zwitterionic betaine precursor.

In certain embodiments, such zwitterionic precursors or zwitterionic betaine precursors comprise (a) polymer backbone; (b) a plurality of cationic centers, each cationic center covalently coupled to the polymer backbone by a first linker; (c) a counter ion associated with each cationic center; and (d) a hydrolyzable group covalently coupled to each cationic center through a second linker, wherein the hydrolyzable group is hydrolyzable to an anionic center to provide a zwitterionic polymer having the anionic center covalently coupled to the cationic center through the second linker.

In certain further embodiments, the zwitterionic betaine precursor has the formula:

P-(L$_1$-N(R$_a$)(R$_b$)-L$_2$-A(=O)—OR$_c$)$_n$(X)$_n$, wherein P is the polymer backbone having n pendant groups L$_1$-N$^+$(R$_a$) (R$_b$)-L$_2$-A(=O)—OR$_c$); N$^+$ is the cationic center; R$_a$ and R$_b$ are independently selected from hydrogen, alkyl, and aryl; A(=O)—OR$_c$ is the hydrolyzable group, wherein A is selected from the group consisting of C, S, SO, P, or PO, and R$_c$ is a halo, alkyl, cyclic, aryl, acyl, or silyl group that may be further substituted with one or more substituents; L$_1$ is a linker that covalently couples the cationic center to the polymer backbone; L$_2$ is a linker that covalently couples the cationic center to the hydrolyzable group; X is the counter ion associated with the cationic center; and n is an integer from about 10 to about 10,000.

In certain embodiments, the polymer backbone is selected from the group consisting of acrylate, acrylamide, methacrylamide and methacrylate and silicone.

In certain embodiments, the cationic center is selected from the group consisting of tertiary ammonium, tertiary imidazolium, triazolium, pyridinium, morpholinium or to secondary ammonium, imidazolium, triazolium, pyridinium, morpholinium and other cationic monomers or combinations thereof.

In certain embodiments, the crosslinkers are hydrophilic crosslinkers. In certain other embodiments, the crosslinkers are hydrophobic crosslinkers. In certain embodiments the crosslinker is zwitterionic.

The amount of crosslinker can be adjusted from 0.01 to 100 weight % related to total monomer weight.

In certain embodiments, the crosslinker is ethylene glycol dimethacrylate crosslinker (EGDMA).

Polycarboxybetaine (PCB) analog ester polymer (with tertiary amine instead of quaternary amine, named PTCBE) were made by carboxybetaine (CB) analog ester (TCBE) monomer with different ester groups such as ethyl and isobornyl (referred to herein as "PTCBEE" and "PTCBIBE," respectively). To prepare PTCBE, 0.5-2 wt % (related to TCBE monomer) of ethylene glycol dimethacrylate crosslinker (EGDMA) and 0.1-2 wt % (related to TCBE monomer) of azobisisobutyronitrile (AIBN) are mixed with TCBE monomer.

The crosslinked zwitterionic precursor material can be used to make any number of articles and devices. For example, the crosslinked zwitterionic precursor material can be cast into discs, tubular molds, or any other customized molds. The thermo-polymerization is carried out at a time range from 2 hours to 5 days in a convection oven at a temperature range from 50° C. to 150° C.

The crosslinked zwitterionic precursor material can be further converted into super hydrophilic zwitterionic moieties in the outer layer via hydrolysis, light, or heat treatment.

The shape of robust free-standing crosslinked zwitterionic precursor material can be constructed via injection molding, blow molding, extrusion molding, calendaring molding, flow casting, compression molding, prevarication molding and 3D printing.

Figure 2:
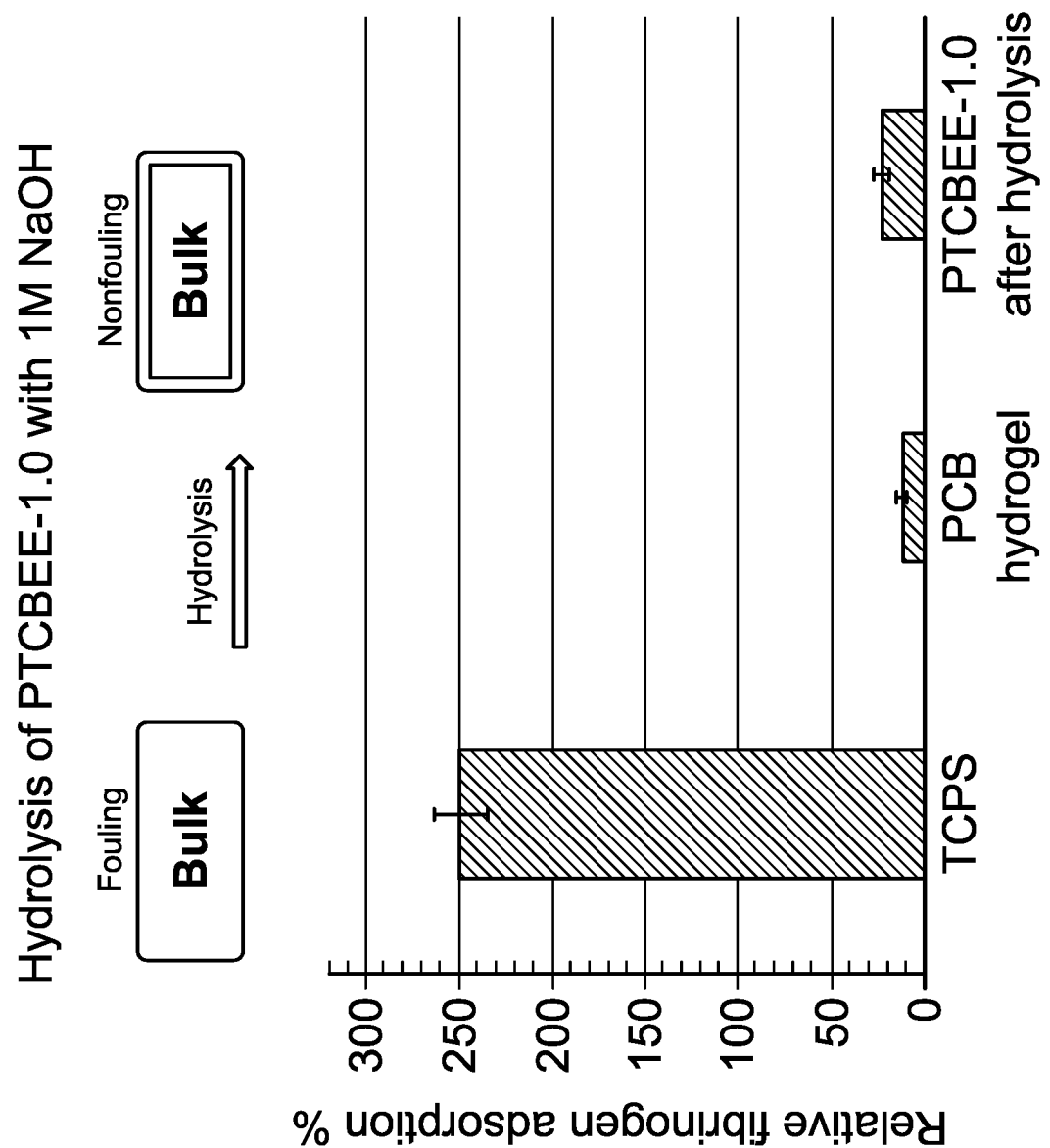
FIG. 2 compares ELISA test data for a free-standing, non-fouling polymer of the present technology (PTCBEE-1.0) after hydrolysis with tissue culture polystyrene (TCPS) and polycarboxybetaine (PCB) hydrogel.

Performance characteristics of representative in-situ hydrolyzed robust zwitterionic polymeric materials are shown and described in FIG. 1-3.

Figure 4:
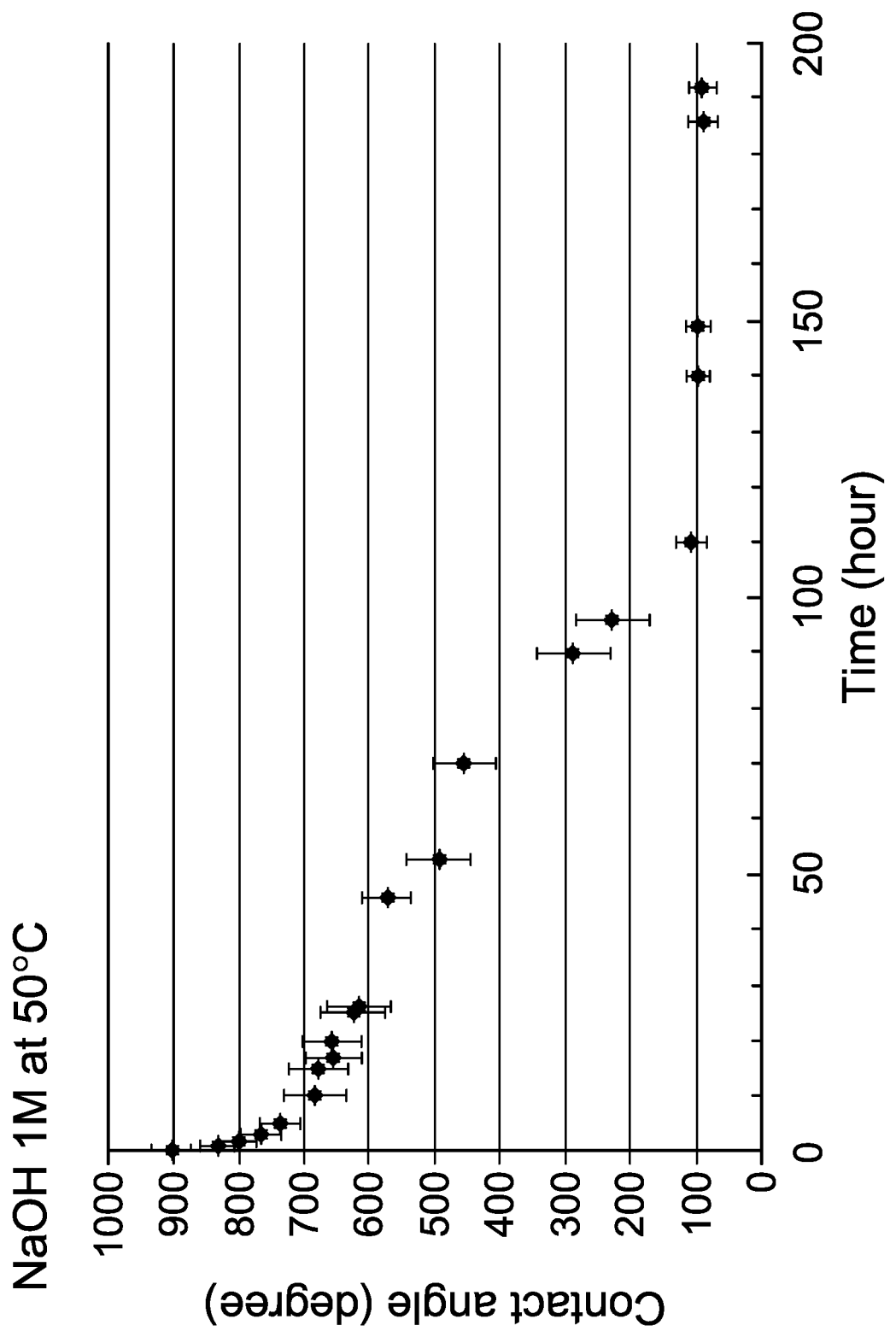
FIG. 4 illustrates contact angle measurements of a representative in-situ crosslinked polymer of the invention (PTCBIBE-2.0) after hydrolysis.

The surface of PTCBIBE-2.0 (2 wt % of crosslinker relative to monomer) crosslinked bulk polymer was simply hydrolyzed under soaking with 1M NaOH aqueous solution at 50° C. Contact angle goniometer was used to monitor the degree of the surface hydrolysis of PTCBIBE-2.0 bulk polymer. When the isobornyl ester was hydrolyzed, the surface slowly turned from hydrophobic to super hydrophilic indicating successful formation of the CB analog with tertiary amine. The static contact angle decreased with soaking time and became lower than 10 degree after about 110 hours indicating full surface hydrolysis, as shown in FIG. 4.

Figure 5:
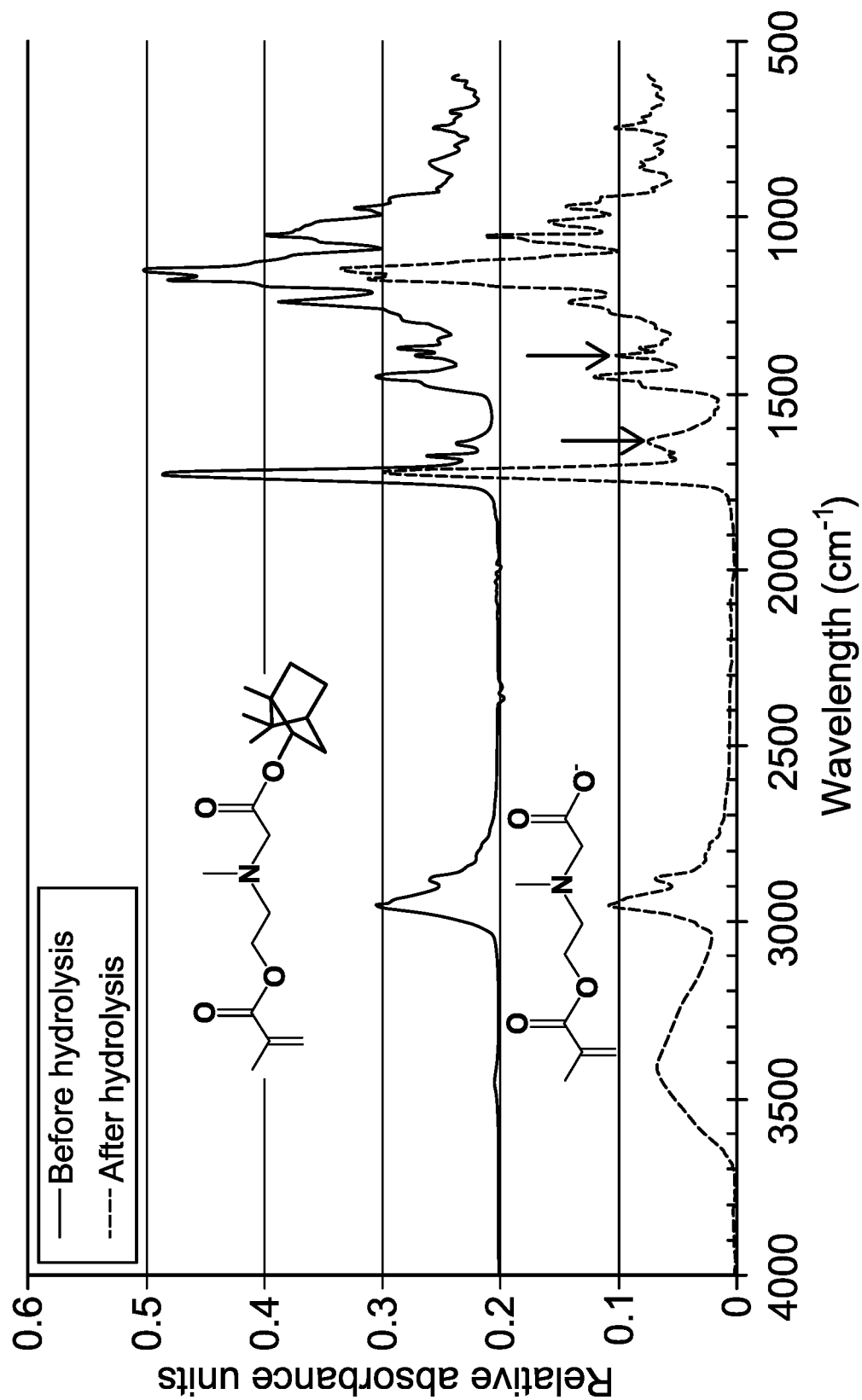
FIG. 5 illustrates the IR spectra of the PTCBIBE-2.0) before and after hydrolysis.

The infrared spectra (ATR-FTIR) of non-hydrolyzed and hydrolyzed PTCBIBE-2.0 are shown in FIG. 5. Two new peaks can be identified at 1639 and 1390 cm$^1$ were assigned to the presence of COO groups, indicating the hydrolysis of ester and the formation of PCB analog groups. Furthermore, an enhanced broad shoulder appears at 3393 cm$^{-1}$, which represents water signal resulting from an increase in hydration caused by the formation of hydrophilic zwitterionic polymer.

Figure 6:
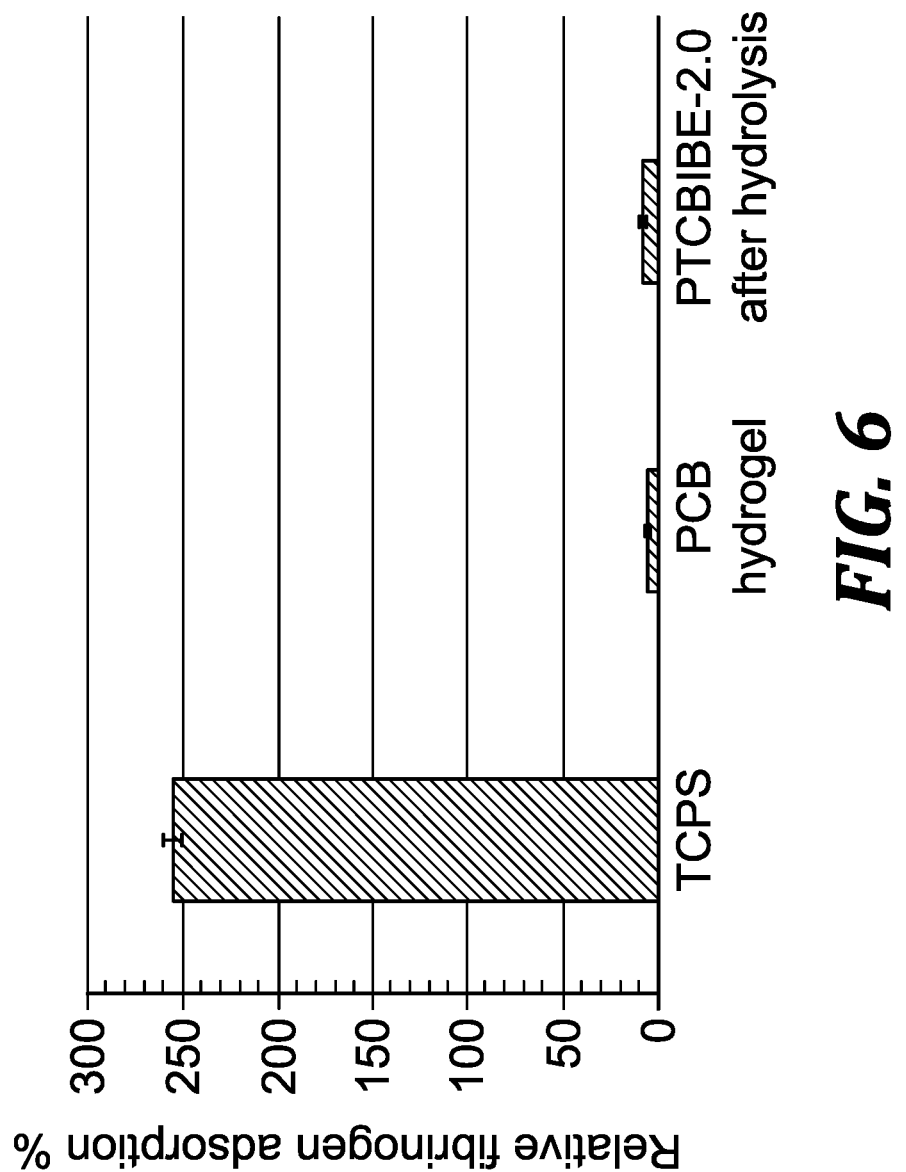
FIG. 6 illustrates ELISA test data for PTCBIBE-2.0 after hydrolysis.

The tertiary PCB analog (where the quaternary amine of PCB is replaced by tertiary amine) achieved strongly zwitterionic state under physiological conditions (such as pH 7.4). The polymer brush made from the tertiary PCB analogue resulted in less than 5±2.1 ng/cm$^2$ protein adsorption for serum or plasma via surface plasmon resonance (SPR) measurements. The pka of tertiary amine and carboxylic group is 8.7 and 2.6 respectively. At pH 7.4 (PBS solution), the tertiary amine tended to be protonated while the carboxylic deprotonated. In addition, the tertiary amine and carboxylic group are close enough to affect each other's protonation and deprotonation, called synergistic effect, resulting in forming anti-fouling zwitterionic structure. Here, fibrinogen adsorption via enzyme-linked immunosorbent assay (ELISA) was used to test the anti-fouling ability on the hydrolyzed surface of PTCBIBE-2.0 crosslinked bulk polymer. Tissue culture polystyrene (TCPS) was used as positive control. Typical PCB non-fouling hydrogel (made from polymerization of monomer 2-carboxy-N, N-dimethyl-N-(2'-(methacryloyloxy)ethyl) ethanaminium inner salt and crosslinker N,N'-methylenebis(acrylamide)) was used as negative control. The results in FIG. 6 showed that PTCBIBE-2.0 bulk polymers with an optimum soaking time of 110 hours showed similar nonfouling behavior to PCB hydrogel with less than 30 ng/cm$^2$ of fibrinogen adsorption.

Figure 7:
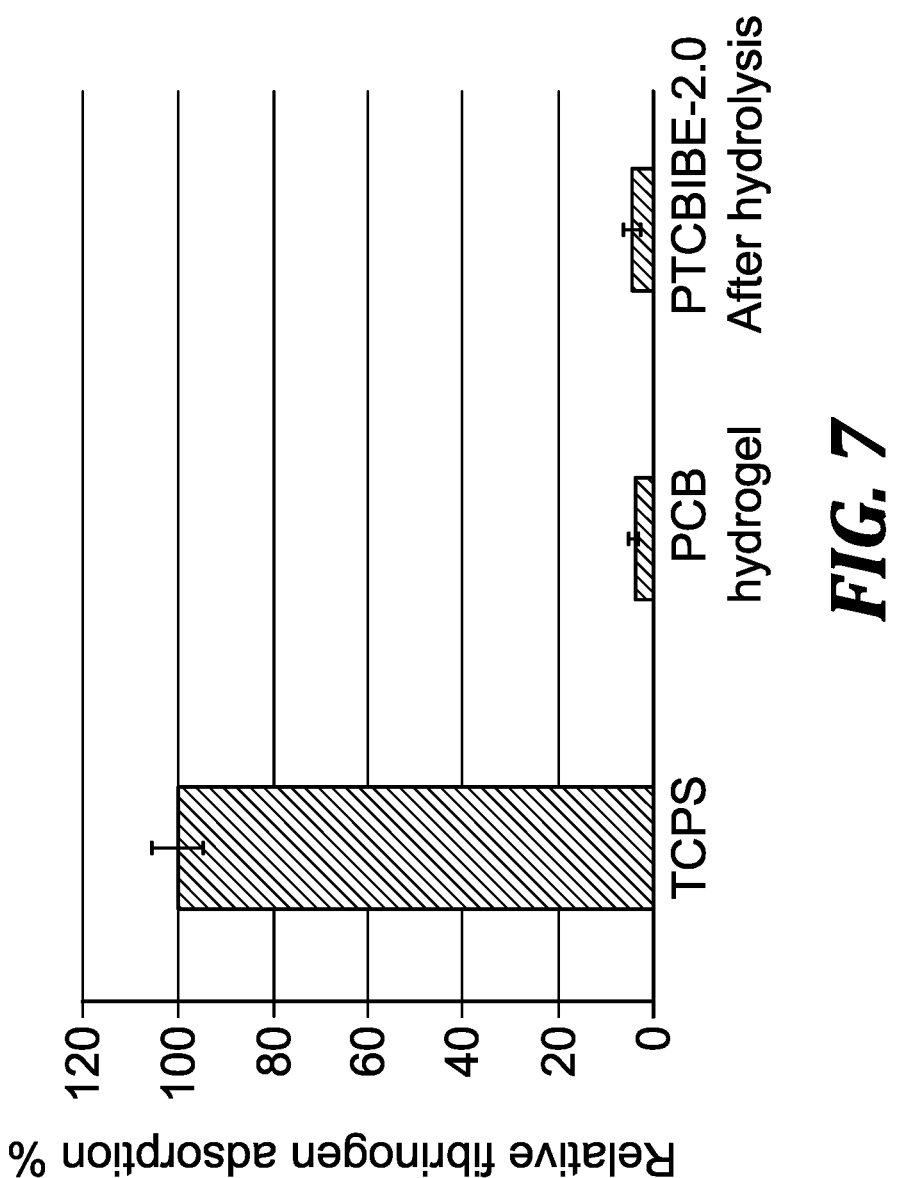
FIG. 7 illustrates BAEC adhesion test data for PTCBIBE-2.0 after hydrolysis.

Low cell adhesion on the material surface plays an important role in designing various types of biomedical devices. FIG. 7 shows the adhesion behaviors of bovine aortic endothelial cell (BAEC) on the PTCBIBE-2.0 (after hydrolysis of 110 h), PCB hydrogel (as a negative control), and TCPS (as a positive control). The quantitative statistics of the attached BAEC was obtained by the MTT assay. After BAEC seeding for 48 h, only few cell adhesion was observed on both the PCB hydrogels and the PTCBIBE-2.0 (after hydrolysis), while BAEC adhered on the surface of TCPS. The surface of PTCBIBE-2.0 suppressed more than 95% BAEC attachment compared to that of TCPS. BAEC adhesion tests showed that both the PCB hydrogels and the PTCBIBE-2.0 (after hydrolysis) have the same excellent cell adhesion-resistance properties due to their superhydrophilicity of zwitterion group, which is also consistent with the results of fibrinogen adsorption tests.

The mechanical properties of PTCBIBE-2.0 bulk polymer after hydrolysis process were examined by tensile tests. As shown in FIG. 8, the mechanical properties after hydrolysis slightly decreased and no significant difference was observed. Due to the stable of isobornyl ester group of PTCBIBE and control of optimized hydrolysis time, only the outer-most polymer layer was hydrolyzed to be super hydrophilic without sacrificing its bulk mechanical properties. The tensile tests successfully verify the dual properties (non-fouling and high strength) of PTCBIBE-2.0.

The preparation of PTCBE crosslinked bulk polymers is described in Example 29.

Methods for measuring polymer mechanical properties (compression and tensile tests) and non-fouling properties (ELISA tests) are described in Examples 30 and 31, respectively.

The invention is not limited to particular embodiments described, as such may, of course, vary. It is also to be understood that the terminology used herein is for the purpose of describing particular embodiments only, and is not intended to be limiting.

As used herein, the singular forms "a," "an," and "the" include plural referents unless the context clearly dictates otherwise. As such, this statement is intended to serve as antecedent basis for use of such exclusive terminology as "solely," "only" and the like in connection with the recitation of claim elements, or use of a "negative" limitation.

As used herein, the term "a" entity or "an" entity refers to one or more of that entity. For example, a polymer refers to one or more polymers. As such, the terms "a", "an", "one or more" and "at least one" can be used interchangeably. Similarly the terms "comprising", "including" and "having" can be used interchangeably. Moreover, as used herein, the terms about and substantially refer to a variation of less than 5% from the object of the term, and preferably less than 2%.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are described. All publications mentioned herein are incorporated herein by reference to disclose and describe the methods and/or materials in connection with which the publications are cited.

Except as otherwise noted, the methods and techniques of the present embodiments are generally performed according to conventional methods well known in the art and as described in various general and more specific references that are cited and discussed throughout the present specification.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed. In addition, all sub-combinations are also specifically embraced by the present invention and are disclosed herein just as if each and every such sub-combination was individually and explicitly disclosed herein.

The following examples are provided for the purpose of illustrating, not limiting, the invention.

EXAMPLES

Example 1

Representative Diamide Zwitterionic Monomer

In this example, the preparation of a representative diamide zwitterionic monomer is described. The synthesis is shown below:

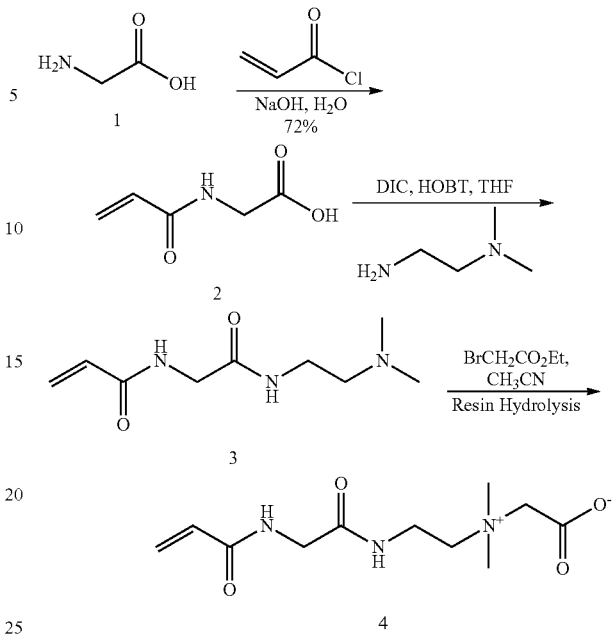

Glycine 1 (1.0 eq) is dissolved in water containing NaOH (1.2 eq). After complete dissolution, acryloyl chloride (1.2 eq) is added dropwise and reaction is stirred for 3 hrs. After completion of the reaction, pH of the solution is adjusted to 2 wherein compound 2 precipitates out in 72% yield.

To a stirred solution of compound 1 (1 eq.) in THF, diisopropyl carbodimide (1.5 eq) and hydroxybenzotriazole (1.5 eq.) are added. The reaction is maintained at 0° C. After 15 min, N,N-dimethyl ethylenediamine (1 eq.) is added. The reaction is stirred overnight. After completion of the reaction, the reaction contents are purified by column chromatography to give compound 3 in 58% yield. $^1$H NMR (300 MHz, DMSO-$d_6$) δ 8.36 (s, 1H), 7.90 (s, 1H), 6.82-6.62 (m, 1H), 6.32 (ddd, J=17.1, 10.1, 1.3 Hz, 1H), 5.62 (dt, J=10.1, 1.7 Hz, 1H), 3.77 (d, J=5.8 Hz, 2H), 3.53-3.38 (t, 2H), 2.45 (t, J=6.7 Hz, 2H), 2.32-2.20 (m, 6H).

To a stirred solution of compound 3 (1 eq.) in acetonitrile, ethyl bromoacetate (3 eq.) is added. The reaction is heated at 60° C. for 24 hours. After completion of the reaction, the reaction contents are purified by column chromatography to give ethyl ester protected compound. Protected ester on hydrolysis with IRN-78 followed by evaporation of solvent gives compound 4 in 54% yield. $^1$H NMR (300 MHz, Methanol-$d_4$) δ 6.45-6.20 (m, 2H), 5.74 (dd, J=9.8, 2.2 Hz, 1H), 4.47 (s, 2H), 4.34 (q, J=7.2 Hz, 2H), 3.95 (d, J=9.9 Hz, 2H), 3.81-3.69 (m, 4H), 3.38 (m, 6H).

Example 2

Representative Cyano-Substituted Zwitterionic Monomers

In this example, the preparation of representative high strength cyano-substituted zwitterionic monomers is described. The synthesis of carboxybetaine monomers CB-CN-1 and CB-CN-2 is shown below.

The synthesis of the monomers is based on the N,N-dimethylaminomethyl-acrylonitrile intermediate shown in figure below.

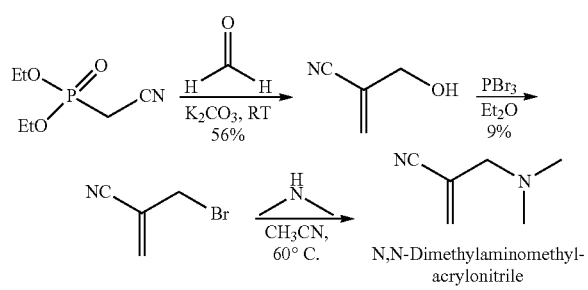

Once the N,N-dimethyl cyano acrylate was obtained, the CB-CN monomers were prepared as shown in below.

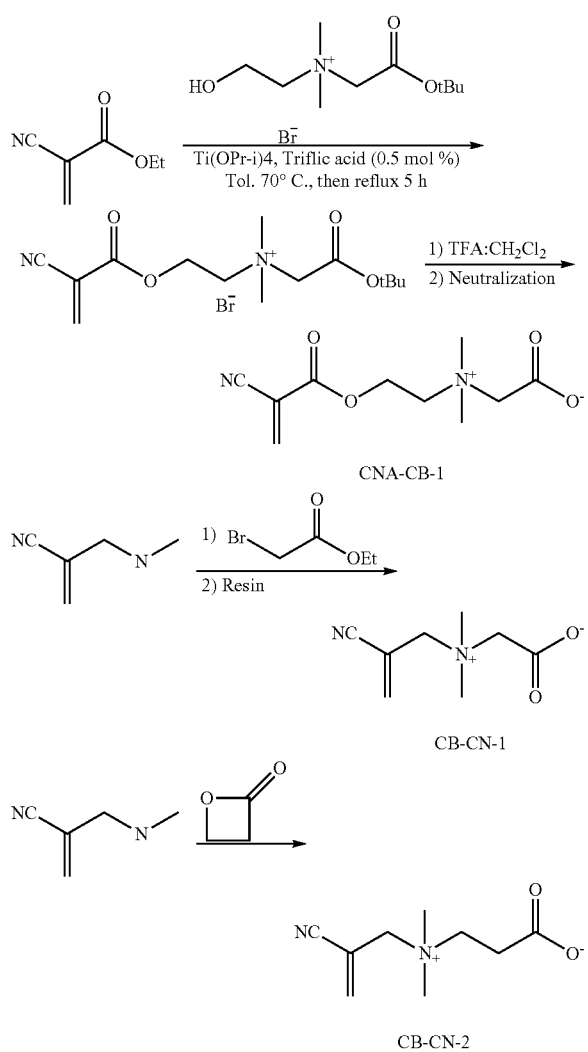

CB-CN-1

CB-CN-2

Example 3

Representative Cyano-Substituted Zwitterionic Monomers

In this example, the preparation of representative cyano-substituted zwitterionic monomers (cyano-substituted carboxybetaine monomers, CN-CB) with cyano groups in the side chain from (cyanomethyl)phosphonate is described.

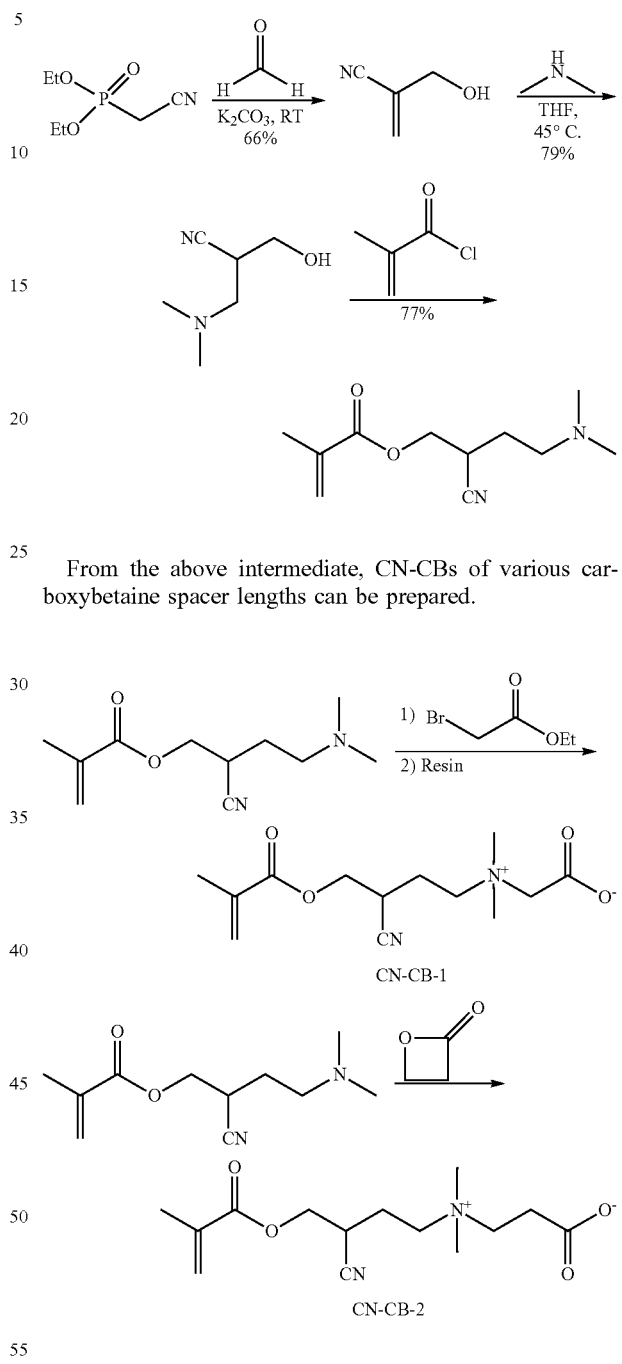

From the above intermediate, CN-CBs of various carboxybetaine spacer lengths can be prepared.

Example 4

Representative Diisocyanate Zwitterionic Monomers

In this example, the preparation of representative diisocyanate zwitterionic monomers (carboxybetaine and sulfobetaine monomers) from zwitterionic diols is described. The syntheses are shown n Schemes 1a and 1b below.

Scheme 1a. Synthesis of CB based di-isocyanate:

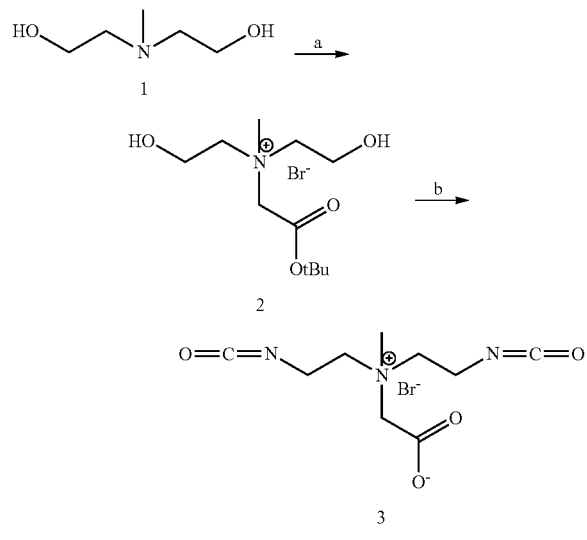

(a) BrCH$_2$CO$_2$tBu, CH$_3$CN
(b) Cyanuric chloride, Bu$_4$NCO, CH$_3$CN

Scheme 1b. Synthesis of CB based di-isocyanate

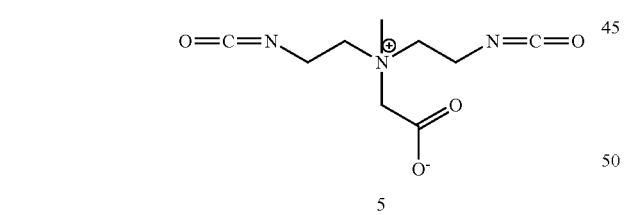

(c) ClCH2COONa, CH$_3$CN
(d) Cyanuric chloride, Bu$_4$NCO, CH$_3$CN

Example 5

Representative Diisocyanate Zwitterionic Monomers

In this example, the preparation of representative diisocyanate zwitterionic monomers (carboxybetaine and sulfobetaine monomers) from diamines is described. The syntheses are shown in Schemes 2a and 2b below.

Alternate Synthesis of Zwitterionic Di-isocyanate Monomer

Scheme 2a.

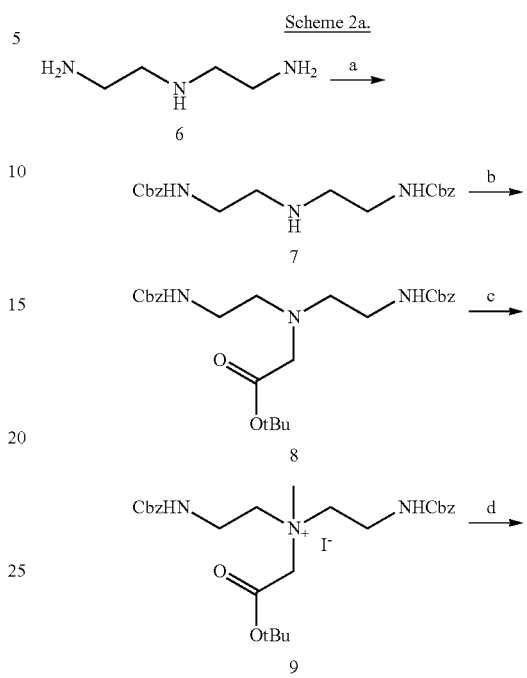

(a) CbzOSu, DCM (b) BrCH$_2$CO$_2$tBu, DIEA, DCM (c) MeI, CH$_3$CN (d) [H$_2$], Pd/C, CH$_3$OH (e) Triphosgene, NaHCO$_3$, DCM Scheme 2b.

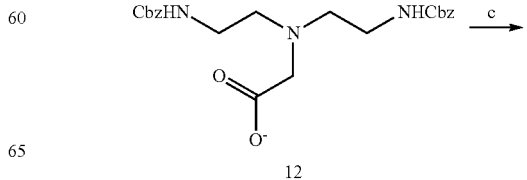

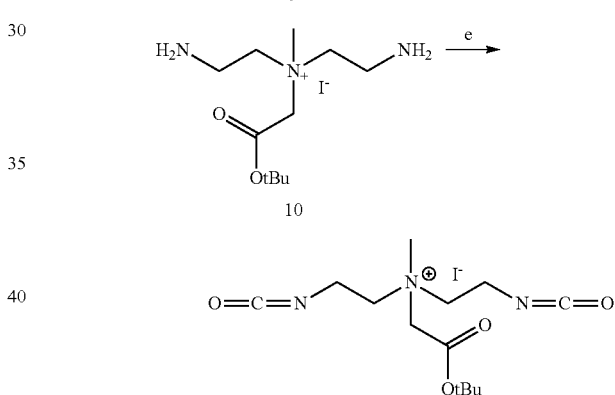

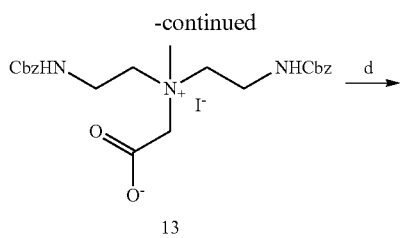

13

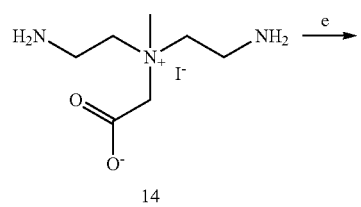

14

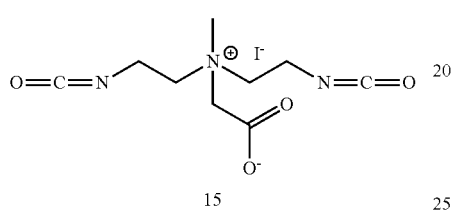

15

(a) CbzOSu, DCM (b) BrCH₂CO₂Na, CH₃CN (c) MeI, CH₃CN (d) [H₂], Pd/C, CH₃OH (e) Triphosgene, NaHCO₃, DCM The sulfobetaine-based diisocyanates are obtained by same synthetic route as for the carboxybetaine diisocyanates.

The syntheses are described below.

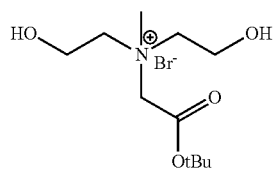

N-Methyl-diethanolamine 1 is dissolved in acetonitrile and tert-butylbromoacetate is added. After completion of the reaction, the reaction mixture is concentrated under vacuum. Crystallization of the residual mixture affords desired compound 2.

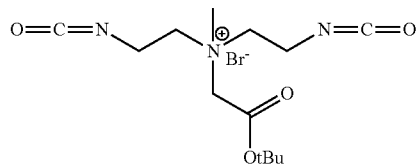 [SMILES: CC(C)(C)OC(=O)C[N+](C)(CCN=C=O)CCN=C=O ; [Br-]]

A solution of compound 2 in dichloromethane is added to a stirred solution of aqueous sodium bicarbonate. The biphasic mixture is cooled in an ice bath and stirred while adding triphosgene in one single lot. After completion of the reaction, the organic layer is collected and aqueous layer is extracted with dichloromethane. The combined organic layers are dried using Na₂SO₄, filtered, concentrated and purified by column chromatography to give di-isocyanate 3.

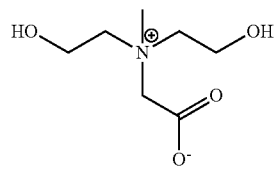

5

N-Methyl-diethanolamine 1 is dissolved in acetonitrile and tert-butylbromoacetate is added to it. After completion of the reaction, the reaction mixture is concentrated under vacuum. Crystallization of the residual mixture affords desired compound 4.

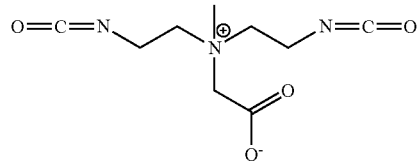 [SMILES: C[N+](CCN=C=O)(CCN=C=O)CC(=O)[O-]]

A solution of compound 4 in dichloromethane is added to a stirred solution of aqueous sodium bicarbonate. The biphasic mixture is cooled in an ice bath and stirred while adding triphosgene in one single lot. After completion of the reaction, the organic layer is collected and aqueous layer is extracted with dichloromethane. The combined organic layers are dried using Na₂SO₄, filtered, concentrated and purified by column chromatography to give di-isocyanate 5.

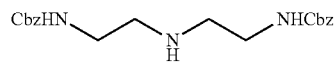

CbzOSu dissolved in dichloromethane is added dropwise to a stirred solution of diethylenetriamine in DCM at 0° C. The reaction mixture is allowed to warm to room temperature and stirred for 15 h. The reaction mixture is then washed with water. The aqueous layer is re-extracted with dichloromethane. The combined organic washes are dried using sodium sulfate and then filtered to give compound 7.

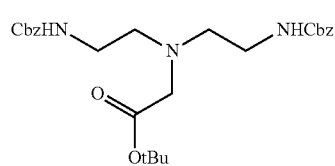 [SMILES: CC(C)(C)OC(=O)CN(CCNC(=O)OCc1ccccc1)CCNC(=O)OCc1ccccc1]

A solution of tert-butyl bromoacetate in dichloromethane is added dropwise to a solution of 7 in dichloromethane and diisopropylethylamine at 0° C. for a period of 30 min. The reaction mixture is allowed to warm to room temperature and stirred overnight. The reaction mixture is then washed with 1M HCl, water, and brine. The organic layer is concentrated to leave a residue which is further purified by column chromatography to give compound 8.

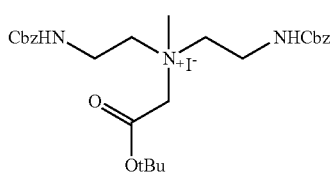 [SMILES: CC(C)(C)OC(=O)C[N+](C)(CCNC(=O)OCc1ccccc1)CCNC(=O)OCc1ccccc1 ; [I-]]

Compound 8 is dissolved in acetonitrile and methyl iodide is added. The reaction contents are heated at 60° C. for 48 h. The reaction contents are stirred until the starting material is completely consumed. The reaction mixture is concentrated to dryness in vacuo and is used in the next step without further purification.

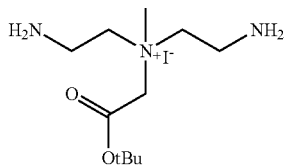 [SMILES: CC(C)(C)OC(=O)C[N+](C)(CCN)CCN ; [I-]]

Compound 9 is taken up in MeOH and 10% Pd/C is added. Hydrogenation is carried overnight at 50 psi. The reaction contents are filtered over diatomaceous earth and concentrated to give compound 10 and is used in the next step without further purification.

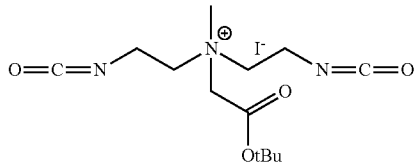 [SMILES: CC(C)(C)OC(=O)C[N+](C)(CCN=C=O)CCN=C=O ; [I-]]

A solution of compound 10 in dichloromethane is added to a stirred solution of aqueous sodium bicarbonate. The biphasic mixture is cooled in an ice bath and stirred while adding triphosgene in one single lot. After completion of the reaction, the organic layer is collected and aqueous layer is extracted with dichloromethane. The combined organic layers are dried using Na$_2$SO$_4$, filtered, concentrated and purified by column chromatography to give di-isocyanate 11.

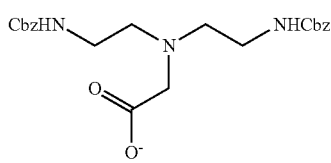 [SMILES: O=C([O-])CN(CCNC(=O)OCc1ccccc1)CCNC(=O)OCc1ccccc1]

To a stirred solution of 7 in acetonitrile is added sodium bromoacetate. The reaction mixture is stirred overnight and the product is purified by crystallization.

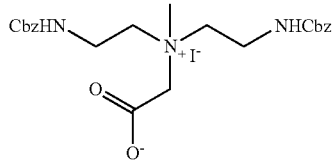

Compound 12 is dissolved in acetonitrile and methyl iodide is added. The reaction contents are heated at 60° C. for 48 h. The reaction contents are stirred until the starting material is completely consumed. The reaction mixture is concentrated to dryness in vacuo and is used in the next step without further purification.

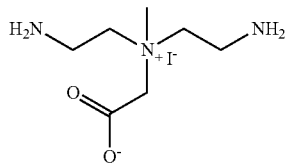

Compound 13 is taken up in MeOH and 10% Pd/C is added. Triethylsilane is added dropwise to the reaction mixture. After completion of the reaction, the reaction contents are filtered over diatomaceous earth and concentrated to give compound 14 and is used in the next step without further purification.

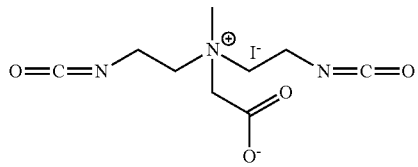 [SMILES: C[N+](CCN=C=O)(CCN=C=O)CC(=O)[O-] ; [I-]]

A solution of compound 14 in dichloromethane is added to a stirred solution of aqueous sodium bicarbonate. The biphasic mixture is cooled in an ice bath and stirred while adding triphosgene in one single lot. After completion of the reaction, the organic layer is collected and aqueous layer is extracted with dichloromethane. The combined organic layers are dried using Na$_2$SO$_4$, filtered, concentrated and purified to give diisocyanate 15.

Example 6

Representative Diisocyanate Zwitterionic Monomers

In this example, the preparation of representative diisocyanate zwitterionic monomers (phosphobetaine and phosphocholine monomers) from diols is described. The syntheses are shown in Schemes 3 and 4 below.

Scheme 3. Synthesis of Phosphocholine based di-isocyanate:
Cyanuric chloride, Bu$_4$NCO, CH$_3$CN

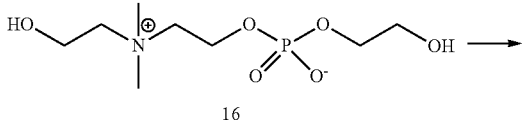

16

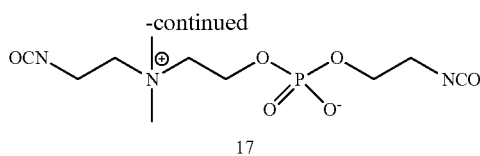

17

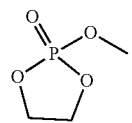

5

Scheme 4. Synthesis of PC and PB diols:

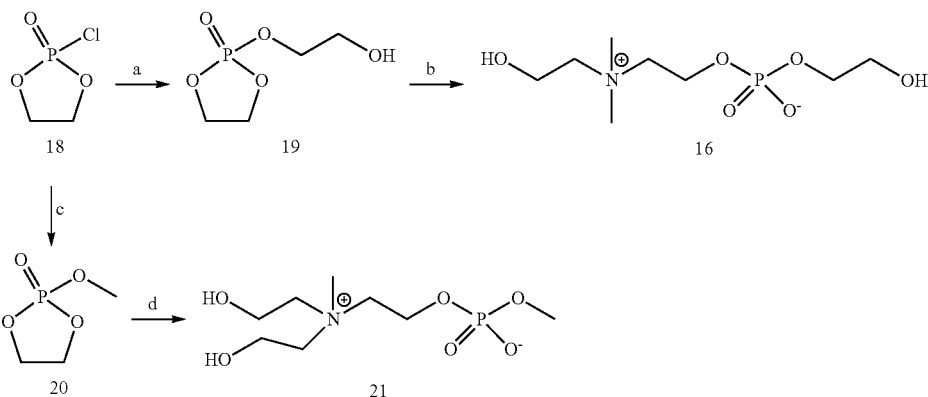

(a) Ethylene glycol, TEA, THF (b) N-Methyldiethanolamine, CH₃CN
(c) MeOH, TEA, THF (d) N-Methyl Diethanolamine, CH₃CN Compounds 16, 19, and 21 can also be synthesized with protected alcohols and the protecting groups cleaved off at the end of the synthesis. Diol 21 can also be converted into the corresponding diisocyanate using the standard procedure as described for making diisocyanate 17 from 16.

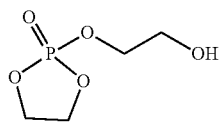

Compound 18 is dissolved in THF and added dropwise to a stirred solution of ethylene glycol and TEA at −20° C. The reaction contents are stirred overnight at this temperature. The precipitates are filtered off and the filtrate is concentrated in vacuo to give compound 16.

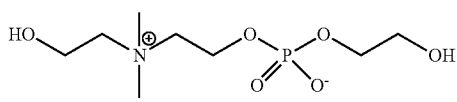 [SMILES: C[N+](C)(CCO)CCOP(=O)([O-])OCCO]

To a stirred solution of compound 18 in acetonitrile is added N-methyl-diethanolamine. The temperature of the reaction is gradually increased to 60° C. After completion of the reaction, the reaction mixture is concentrated in vacuo and the product is purified by crystallization.

To a stirred solution of MeOH, TEA and THF at −20° C. is added compound 18. After completion of the reaction, the precipitated white solid is filtered out and the solution is concentrated in vacuo and the resulting mixture is purified to give compound 20.

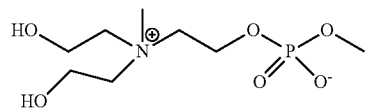 [SMILES: COP(=O)([O-])OCC[N+](C)(CCO)CCO]

To a stirred solution of compound 20 in acetonitrile is added N-methyl-diethanolamine. The temperature of the reaction is gradually increased to 60° C. After completion of the reaction, the reaction mixture is concentrated in vacuo and the product is purified by crystallization.

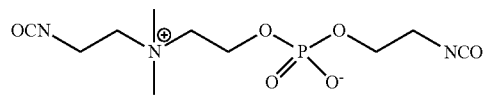

A solution of compound 16 in dichloromethane is added to a stirred solution of aqueous sodium bicarbonate. The biphasic mixture is cooled in an ice bath and stirred while adding triphosgene in one single lot. After completion of the reaction, the organic layer is collected and aqueous layer is extracted with dichloromethane. The combined organic layers are dried using Na₂SO₄, filtered, concentrated and purified by column chromatography to give diisocyanate 17.

Other representative zwitterionic diisocyanate monomers include:

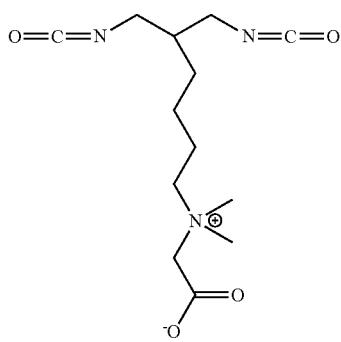
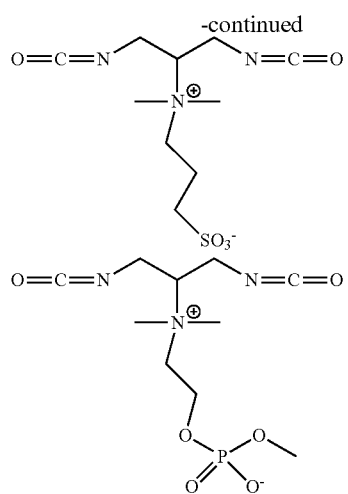
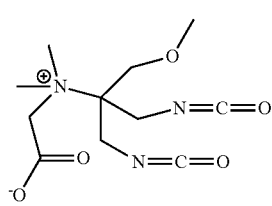
Example 7
Representative Diol Zwitterionic Monomers
In this example, the preparation of representative diol zwitterionic monomers is described. The synthesis is shown in Scheme 5.
Scheme 5.
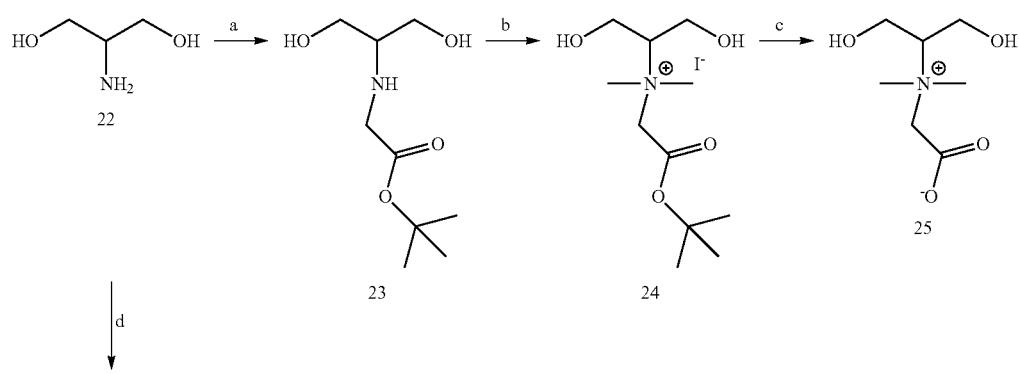
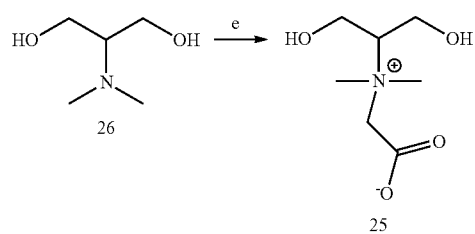
(a) BrCH$_2$CO$_2$tBu, CH$_3$CN, DIEA (b) MeI, CH$_3$CN, heat (c) TFA/DCM followed IRN-78 Neutralization (d) MeI, CH$_3$CN (e) BrCH$_2$CO$_2$Na, CH$_3$CN Representative zwitterionic diols that can be prepared as described above include the following:

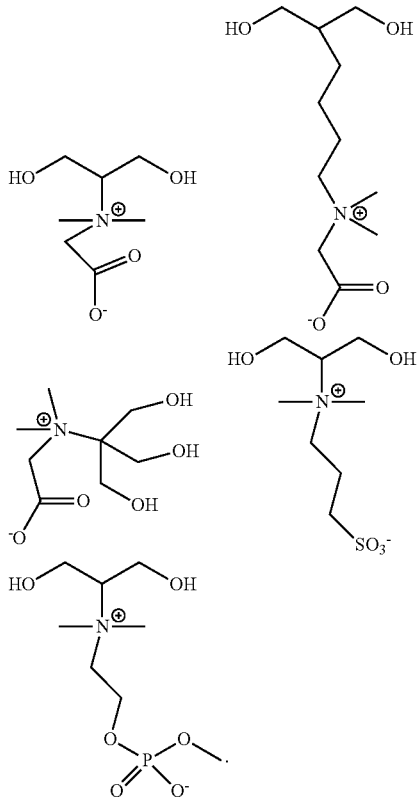

Example 8

Representative Zwitterionic Macromonomers

In this example, the preparation of representative zwitterionic macromonomers (macrodiols and macrodiamines) from zwitterionic precursors is described.

The zwitterionic precursor is prepared as shown below.

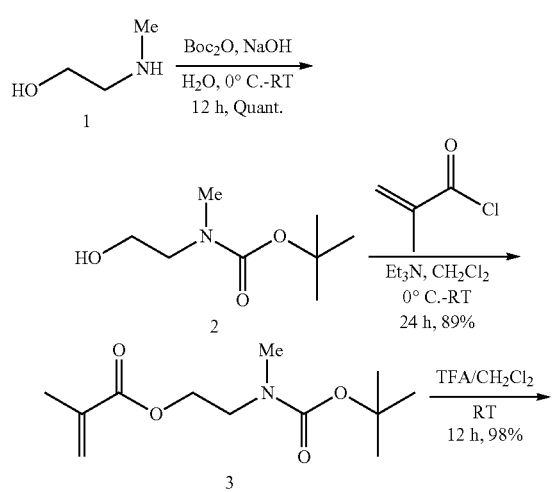

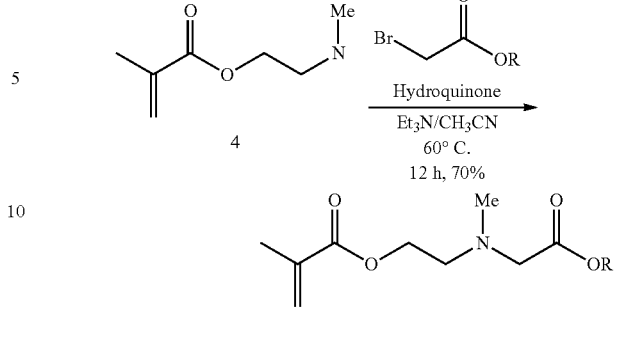

N-tert-Butoxycarbonyl-N-methyl-ethanol amine (2)

N-Methyl-ethanol amine was dissolved in 1 N sodium hydroxide and the solution was cooled to 0° C. Di-tert-butyl dicarbonate was added to the mixture and the reaction was stirred and allowed to warm to room temperature overnight. The product was then extracted with ethyl acetate and the combined organic phase was dried over anhydrous sodium sulfate. After removal of the ethyl acetate under reduced pressure, the pure product was obtained as colorless.

N-tert-Butoxycarbonyl-N-methyl-2-aminoethyl-methacrylate (3)

N-tert-Butoxycarbonyl-N-methyl-ethanolamine and triethylamine were dissolved in anhydrous dichloromethane and the solution was cooled to 0° C. Methacryloyl chloride was added dropwise and the solution was stirred at room temperature. The reaction was quenched at 0° C. by slow addition of ice-water then diluted with dichloromethane. The solvent phases were separated and the organic phase was washed with $H_2O$ and brine. After drying over sodium sulfate, the solvent was removed under reduced pressure and the crude mixture was purified by silica gel chromatography. The pure product was obtained as yellow oil.

N-Methyl-2-aminoethyl-methacrylate (4)

N-tert-Butoxycarbonyl-N-methyl-2-aminoethyl-methacrylate was dissolved in anhydrous dichloromethane. Trifluoroacetic acid was added and the reaction mixture was stirred at room temperature. The solvent was removed under reduced pressure and the crude residue was purified by silica gel chromatography. The pure product was obtained as light yellow oil.

2-((2-Ethoxy-2-oxoethyl)(methyl)amino)ethyl methacrylate (5) (R is ethyl)

N-methyl-aminoethyl-methacrylate and triethylamine were dissolved in anhydrous acetonitrile. Ethylbromoacetate was added dropwise and the mixture was stirred at 60° C. The reaction was cooled to room temperature and the solvent was removed under reduced pressure. The crude residue was dissolved in ethyl acetate and the organic phase was washed with $H_2O$. After drying over sodium sulfate and evaporation of the solvent, the crude mixture was purified by silica gel chromatography. The pure product was obtained as light brown oil.

2-((2-(tert-Butoxy)-2-oxoethyl)(methyl)amino)ethyl methacrylate (6) (R is tert-butyl)

N-methyl-aminoethyl-methacrylate and triethylamine were dissolved in anhydrous acetonitrile. t-Butylbromoacetate was added dropwise and the mixture was stirred at 60° C. The reaction was cooled to room temperature and the solvent was removed under reduced pressure. The crude residue was dissolved in ethyl acetate and the organic phase was washed with $H_2O$. After drying over sodium sulfate and evaporation of the solvent, the crude mixture was purified by silica gel chromatography. The pure product was obtained as light yellow oil.

Synthesis of Zwitterionic Macrodiol or Macrodiamine

Zwitterionic macrodiol or macrodiamine can be synthesis by step polymerization, free radical chain growth polymerization, or living radical polymerization. Examples are as follows:

macrodiol made by reversible addition-fragmentation chain-transfer polymerization (RAFT);

macrodiol made by free radical polymerization with presence of chain transfer agent; and macrodiol or macrodiamine made by atom transfer radical polymerization (ATRP).

Example 9

Representative Zwitterionic Polyurethanes

In this example, the preparation of representative zwitterionic polyurethanes is described. The synthesis is shown in Scheme 6 below.

Scheme 6. Synthesis of Polyurethane:

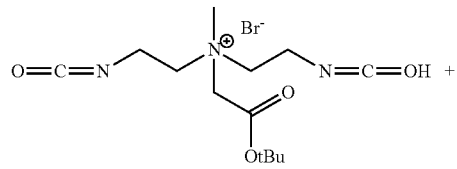

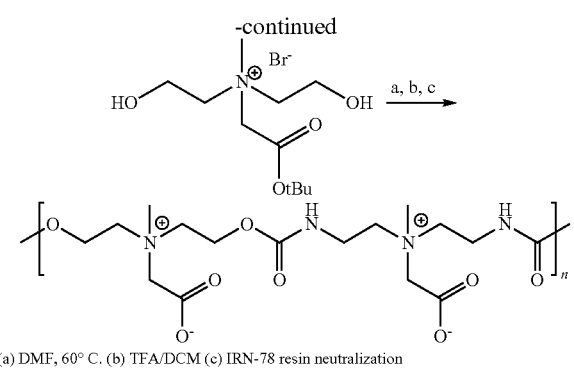

(a) DMF, 60° C. (b) TFA/DCM (c) IRN-78 resin neutralization

To a stirred solution of diisocyanate 3 in dry acetonitrile is added compound 2. The reaction contents are heated at 60° C. in presence of inert nitrogen gas. After polymerization, the deprotection of tert-butyl protecting groups is performed using TFA/DCM followed by neutralization with IRN-78 to give desired polyurethane.

This example shows the synthesis of a zwitterionic polyurethane (PU) with protected carboxybetaine (CB). The method is directly applicable to the synthesis of protected or unprotected CB, SB, PB, and PC.

Example 10

Representative Mixed Charged Monomers

In this example, the preparation of representative mixed charge monomers is described. Polymerizable mixed charged monomers or precursors of mixed charged monomers used for the synthesis of nonfouling zwitterionic polymers via condensation/addition polymerization.

Mixed charged condensation polymers can be prepared by copolymerizing cationic monomer, 2-isocyanato-N-(2-isocyanatoethyl)-N,N-dimethylethanaminium bromide with hydrolysable hydrophobic monomer, ethyl 5-hydroxy-3-(2-hydroxyethyl)pentanoate. Condensation polymerization is used (Scheme 7). The synthesis is a representative mixed charge polyurethane is shown in Scheme 7.

Scheme 7. Synthesis of representative mixed charge polyurethanes.

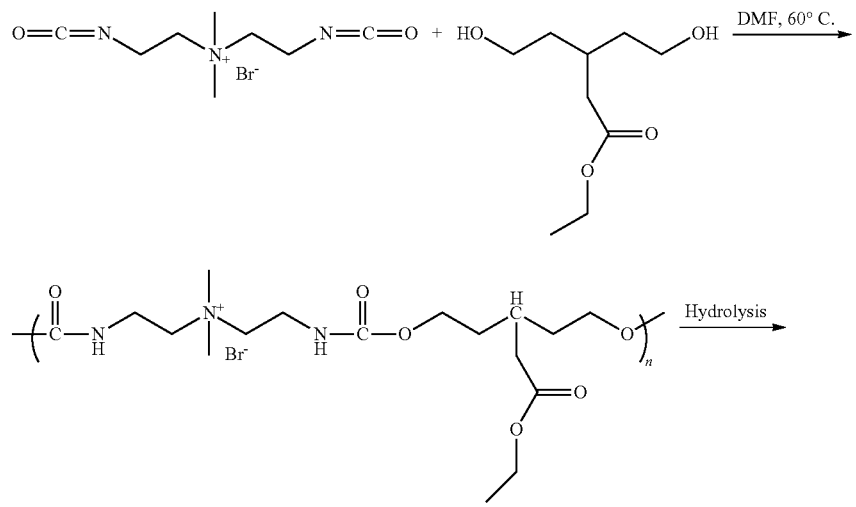

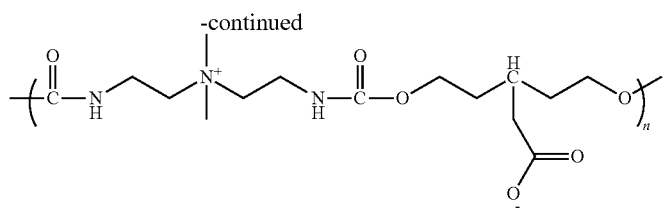

Example 11

Representative Zwitterionic Polymer by Polycondensation Reaction

In this example, the preparation of representative zwitterionic polymer (a linear carboxybetaine) is described. The zwitterionic polymer is prepared by a polycondensation reaction between a latent zwitterionic diamine and a latent zwitterionic diester.

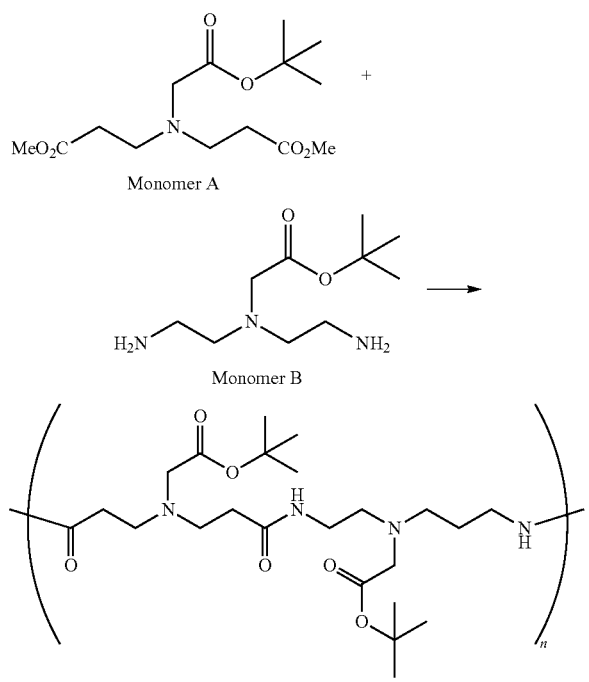

A mixture of solution of diamine and diester is heated to 140-190° C. Upon completion (4-8 hours), the crude product is treated with TFA to provide the zwitterionic linear polymer.

Monomers A and B can be synthesized as described below:

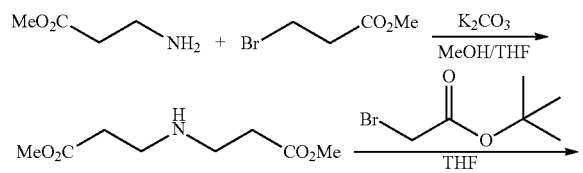

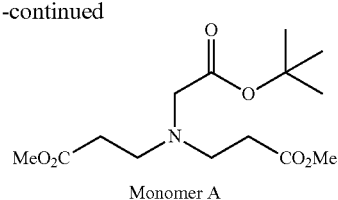

Monomer A: To the solution of amine 1 (10 mmol) in THF/MeOH (1:1, 200 mL) was added K$_2$CO$_3$ (20 mmol) at room temp. Bromo compound (10 mmol) was then added to the suspension and the mixture was stirred for 2 h. H$_2$O was added and the mixture was extracted with EtOAc, washed with brine and dried with Na$_2$SO$_4$. Removing the solvent under vacuum afforded crude secondary amine, which was used for next step without purification. To this solution of crude secondary amine (10 mmol) in THF was added tert-Butyl bromoacetate (11 mmol). The mixture was stirred for 4 h and the solvent was removed under vacuum. The residual was purified with flash column (MeOH:CH$_2$Cl$_2$ 1:10) to give monomer A (70% for 2 steps).

$^1$H NMR (400 MHz, CDCl$_3$) δ 1.44 (s, 9H), 2.44 (t, J=7.9 Hz, 4H), 2.96 ((t, J=7.9 Hz, 4H), 3.28 (s, 2H), 3.65 (s, 6H).

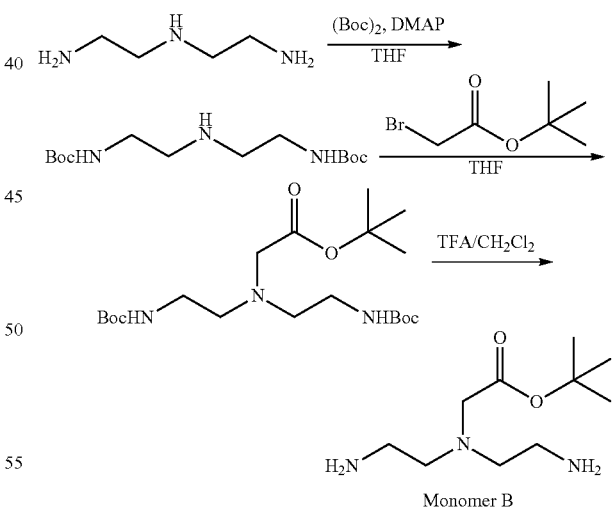

Monomer B: To the solution of diethylenetriamine (10 mmol) in THF (100 mL) was added Boc anhydride (20 mmol) and DMAP (1 mmol) at room temp. The mixture was stirred for 4 h and poured in to H$_2$O (50 mL). The aqueous layer was extracted with EtOAc (3×) and the combined organic was washed with brine, dried with Na$_2$SO$_4$. The solvent was removed under vacuum to afford the crude secondary amine, which was used for next step without purification. To the solution of crude secondary amine (10 mmol) in THF was added tert-Butyl bromoacetate (11 mmol). The mixture was stirred for 4 h and the solvent was removed under vacuum. The residual was purified with flash column (MeOH:CH$_2$Cl$_2$ 1:10) to give completely protected precursor. Boc protecting groups are then deprotected using TFA/CH$_2$Cl$_2$ at room temp for 2 hours. The mixture was neutralized with aqueous NaOH and extracted with CH$_2$Cl$_2$, washed with brine, and dried with Na$_2$SO$_4$. The solvent was removed under vacuum to afford the desired crude monomer, which was purified with flash column (MeOH:CH$_2$Cl$_2$ 1:5) to give monomer B (62% for 2 steps).

$^1$H NMR (400 MHz, CDCl$_3$) δ 1.44 (s, 9H), 2.51 (t, J=6.2 Hz, 4H), 2.96 (m, 4H), 3.28 (s, 2H).

Example 12

Representative Degradable Zwitterionic Polymer by Polycondensation Reaction

In this example, the preparation of representative degradable zwitterionic polymer (a linear carboxybetaine that includes ester bonds in the polymer backbone) is described. The zwitterionic polymer is prepared by a polycondensation reaction between a latent zwitterionic diol amine and a latent zwitterionic diester.

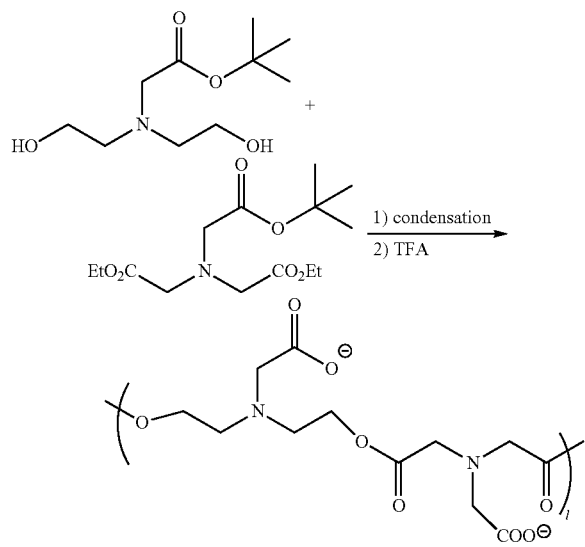

Monomers A and B can be synthesized as described below:

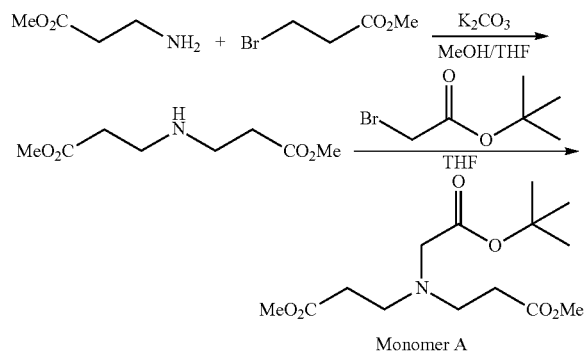

Monomer A

Monomer A: To the solution of amine 1 (10 mmol) in THF/MeOH (1:1, 200 mL) was added K$_2$CO$_3$ (20 mmol) at room temp. Bromo compound (10 mmol) was then added to the suspension and the mixture was stirred for 2 h. H$_2$O was added and the mixture was extracted with EtOAc, washed with brine and dried with Na$_2$SO$_4$. Removing the solvent under vacuum afforded crude secondary amine, which was used for next step without purification. To this solution of crude secondary amine (10 mmol) in THF was added tert-Butyl bromoacetate (11 mmol). The mixture was stirred for 4 h and the solvent was removed under vacuum. The residual was purified with flash column (MeOH:CH$_2$Cl$_2$ 1:10) to give monomer A (70% for 2 steps).

$^1$H NMR (400 MHz, CDCl$_3$) δ 1.44 (s, 9H), 2.44 (t, J=7.9 Hz, 4H), 2.96 ((t, J=7.9 Hz, 4H), 3.28 (s, 2H), 3.65 (s, 6H).

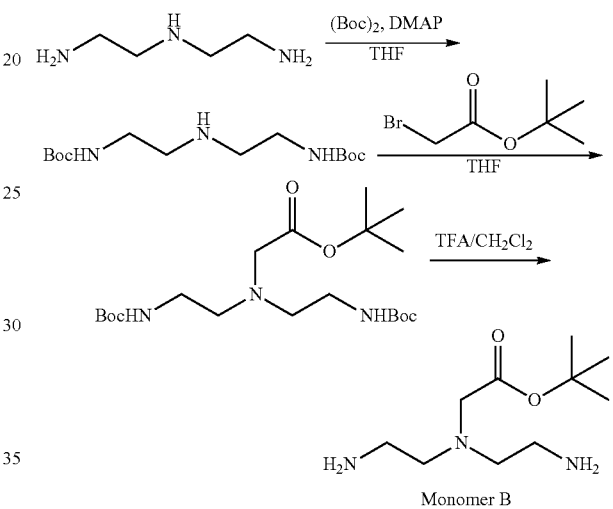

Monomer B

Monomer B: To the solution of diethylenetriamine (10 mmol) in THF (100 mL) was added Boc anhydride (20 mmol) and DMAP (1 mmol) at room temp. The mixture was stirred for 4 h and poured in to H$_2$O (50 mL). The aqueous layer was extracted with EtOAc (3×) and the combined organic was washed with brine, dried with Na$_2$SO$_4$. The solvent was removed under vacuum to afford the crude secondary amine, which was used for next step without purification. To the solution of crude secondary amine (10 mmol) in THF was added tert-Butyl bromoacetate (11 mmol). The mixture was stirred for 4 h and the solvent was removed under vacuum. The residual was purified with flash column (MeOH:CH$_2$Cl$_2$ 1:10) to give completely protected precursor. Boc protecting groups are then deprotected using TFA/CH$_2$Cl$_2$ at room temp for 2 hours. The mixture was neutralized with aqueous NaOH and extracted with CH$_2$Cl$_2$, washed with brine, and dried with Na$_2$SO$_4$. The solvent was removed under vacuum to afford the desired crude monomer, which was purified with flash column (MeOH:CH$_2$Cl$_2$ 1:5) to give monomer B (62% for 2 steps).

$^1$H NMR (400 MHz, CDCl$_3$) δ 1.44 (s, 9H), 2.51 (t, J=6.2 Hz, 4H), 2.96 (m, 4H), 3.28 (s, 2H).

Monomer A was synthesized as described in Example 11.

The mixture of solution of diol and diester is heated in presence of a transesterification catalyst to 140-190° C. Upon completion (4-8 hours), the crude product is treated with TFA to provide zwitterionic linear polymer with molecular weight about 26,000 as determined by GPC.

Example 13

Representative Zwitterionic Polymer by Michael Addition: Ester-Containing Backbone In this example, the preparation of representative zwitterionic polymer, a carboxybetaine that includes ester bonds in the polymer backbone, is described. The zwitterionic polymer is prepared by Michael addition between an acrylate and an amine.

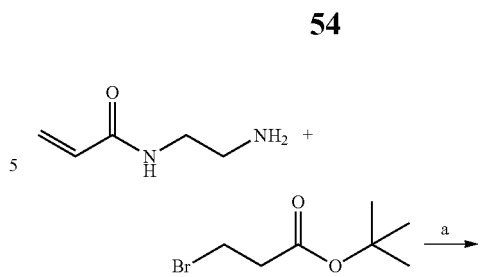

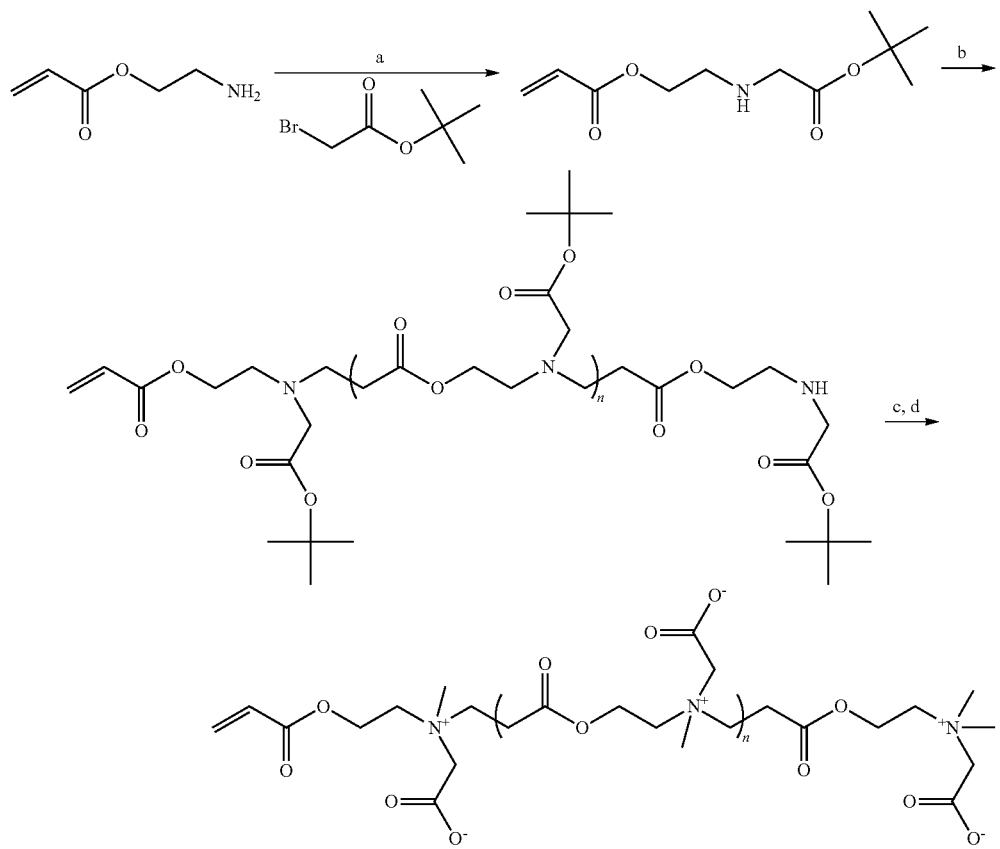

In the above scheme, 2-aminoethyl acrylate is added to THF with triethylamine, then t-butyl bromoacetate added to form the secondary amine carboxybetaine-tert-butyl acrylate ester, to provide the monomer (a), which is the reacted in conditions favoring Michael addition between each amine and acrylate and not free-radical polymerization of acrylates to form poly(ester CB-tBu) (b), followed by treatment with iodomethane to methylate the resulting tertiary amines (c), hydrolysis of the tert-butyl esters with TFA, and neutralization with IRN-78 basic ion exchange resin.

Example 14

Representative Zwitterionic Polymer by Michael Addition: Amide-Containing Backbone In this example, the preparation of representative zwitterionic polymer, a carboxybetaine that includes amide bonds in the polymer backbone, is described. The zwitterionic polymer is prepared by Michael addition between an acrylamide and an amine.

This linear CB polymer is only minimally biodegradable owing to amides in its polymer backbone. The polymer is appropriate for applications in which long-term polymer stability is desirable.

-continued

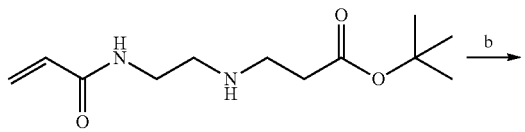

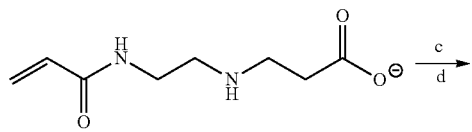

-continued

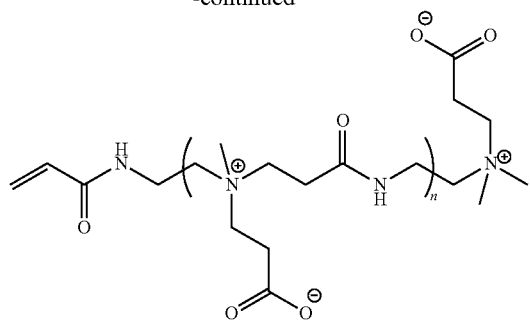

In the above scheme, aminoethyl methacrylamide is added to tert-butyl 3-bromoproionate in THF to form 2° amine CB acrylamide-tBu (a), which is deprotected under acidic conditions using TFA to provide the monomer (b), which is placed in a catalytic solution (e.g., pH=9, adjusted with triethylamine or carbonate) to initiate Michael-type polyaddition and the reaction is allowed to proceed at room temperature for up to one week (c), and iodomethane is added to methylate tertiary amines (d). Polymers are purified by dialysis or size-fractionation.

Example 15

Representative Zwitterionic Polymer by Michael Addition: Thioether- and Ester-Containing Backbone In this example, the preparation of representative zwitterionic polymer, a carboxybetaine that includes thioether and ester bonds in the polymer backbone, is described. The zwitterionic polymer is prepared by alkene-thiol click addition.

A schematic outlining the synthesis of poly(sulfidecarboxybetaine) (PSCB) is shown below. Care must be taken throughout not to oxidize thiol groups so as to avoid disulfide formation. In part I, a tBu-protected acrylate monomer containing a tertiary amine is formed. In part II, a trityl-protected, bromoacetamide thiol component is produced. Finally, these two compounds are reacted in acetonitrile at 70° C. to generate the trityl-protected monomer used to produce PSCB. Next, this monomer is deprotected and polymerized in one pot to minimize the chance of disulfide formation after deprotection. To deprotect the thiol, triethylsilane and TFA are added in a 1:2 volume ratio to the protected monomer dissolved in degassed DCM with a stir bar. The reaction is vented with a needle and stirred rapidly for 15 min until color change indicates the deprotection is complete. The triethylsilane acts as a scavenger to prevent reprotection of the thiol. The solution is once again degassed and polymerization is initiated by adding TEA (or other basic catalyst) or hexylamine/phosphine (or other nucleophilic catalyst). Polymerization reaction is stirred for 48 h and watched for color or viscosity changes. Finally, product is purified through repeated precipitation and dialysis.

I

A

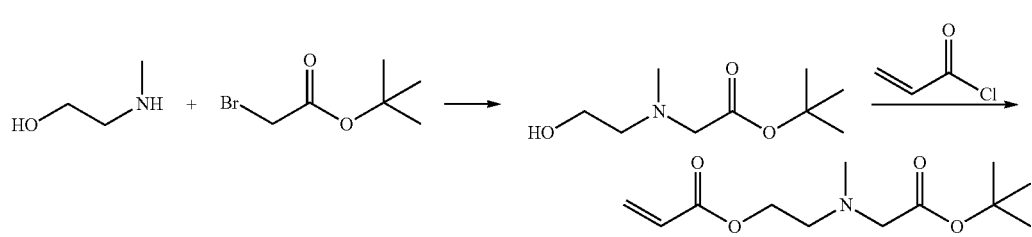

II

B

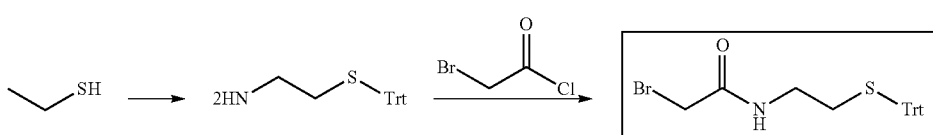

III

C

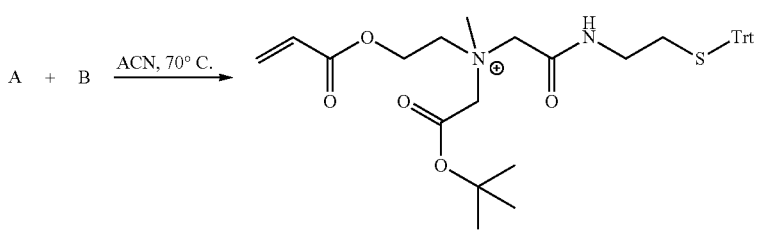

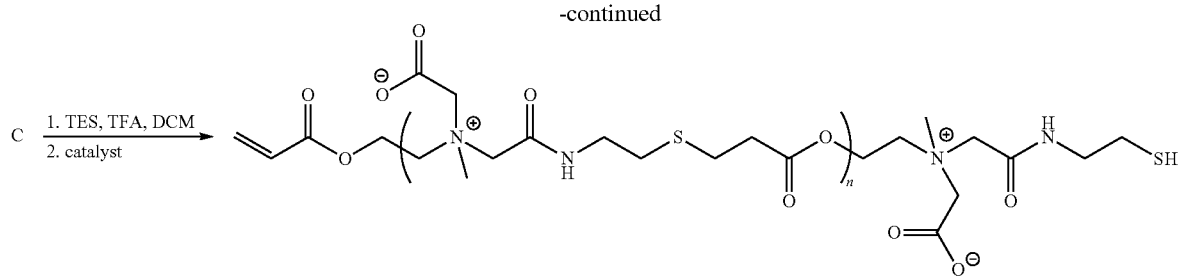

Example 16

Representative Zwitterionic Polymer by Michael Addition: Disulfide- and Amide-Containing Backbone

In this example, the preparation of representative zwitterionic polymer, a linear carboxybetaine that includes disulfide and amide bonds in the polymer backbone, is described. The linear polymers are formed by Michael addition of zwitterionic diamine with a zwitterionic diacrylate.

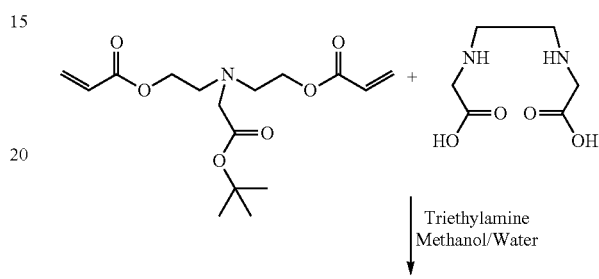

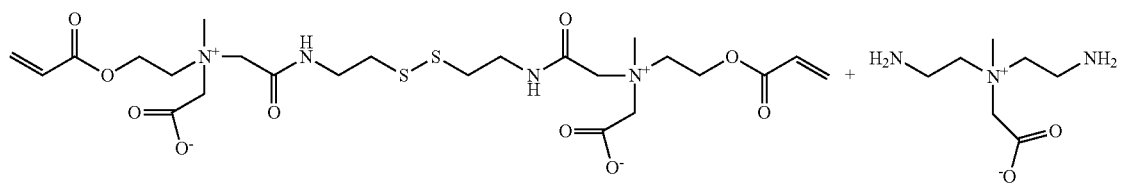

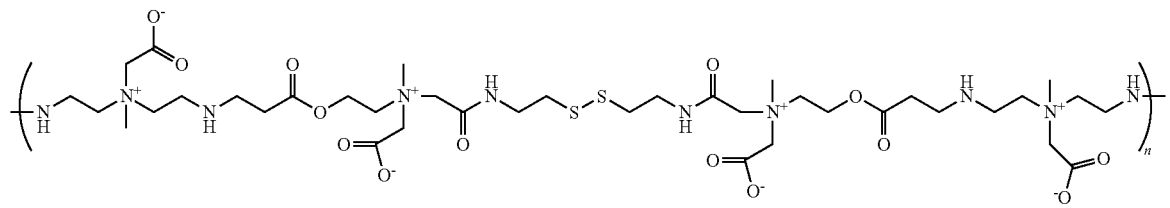

Example 17

Representative Zwitterionic Polymer by Michael Addition: Diacrylate and Secondary Diamine

In this example, the preparation of representative zwitterionic polymer, a linear carboxybetaine that includes ester bonds in the polymer backbone, is described. The linear polymers are formed by Michael addition of latent zwitterionic diamine with a zwitterionic diacrylate.

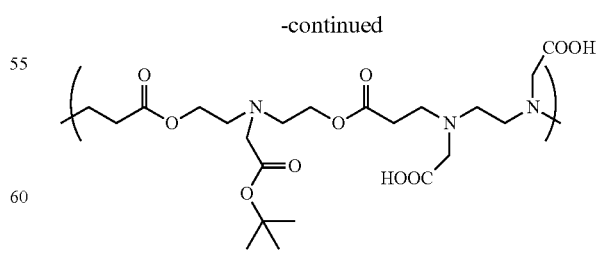

-continued

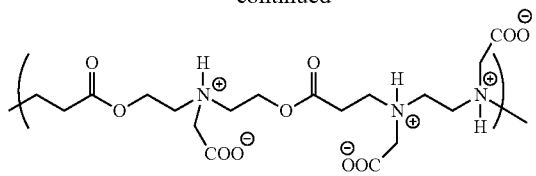

In the above scheme, the zwitterionic diacrylate is treated with ethylenediamine diacetic acid in triethylamine/water mixture for 6 days.

Protected tertiary amine zwitterionic diacrylate (0.25 g, 0.00076 mol) is mixed with ethylenediamine diacetic acid (0.1 g, 0.000568 mol) in methanol (8 mL)/water (1 mL) mixture in presence of trimethylamine (2 mL) for 6 days. The solution turned brown in color. The solvent was removed by rotary evaporation. The polymer is purified by precipitation in THF. The deprotection reaction was performed in dichloromethane using trifluoroacetic acid, followed by neutralization with IRN-78 basic ion exchange resin. The final polymer purified by precipitation in tetrahydrofuran (THF).

Example 18

Representative Zwitterionic Polymer by Michael Addition: Diacrylate and Secondary Diamine In this example, the preparation of representative zwitterionic polymer, a linear carboxybetaine that includes ester bonds in the polymer backbone, is described. The linear polymers are formed by Michael addition of latent zwitterionic secondary diamine with a zwitterionic diacrylate.

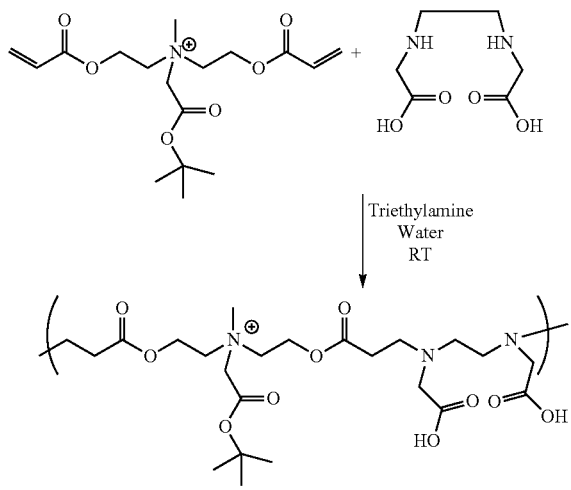

In the above scheme, the zwitterionic diacrylate is treated with ethylenediamine diacetic acid in triethylamine/water mixture for 6 days.

In a typical reaction 0.47 g (0.0015 mol) of the zwitterionic diacrylate is added with 0.205 g (0.011 mol) of ethylenediaminediacetic acid in a round bottom flask. Then 10 g of water was added to the flask followed by the addition of 0.35 g triethyl amine (3× molar excess). The solution becomes clear and turns into brown color. The solution was allowed to stir at room temperature for 6 days. The solution is concentrated using rotary evaporation method. The final polymer is purified by precipitating the polymer in tetrahydrofuran (THF) as non-solvent. Upon MALDI analysis the polymer was found to have molecular weight in the range of 1000-3000 Da.

Example 19

Representative Zwitterionic Polymer by Michael Addition: Diacrylate and Secondary Diamine In this example, the preparation of representative zwitterionic polymer, a linear carboxybetaine that includes ester bonds in the polymer backbone, is described. The linear polymers are formed by Michael addition of latent zwitterionic secondary diamine with a zwitterionic diacrylate.

Typical examples of synthesizing this polymer involve Michael addition reaction between a zwitterionic diacrylate and a bis(secondary amine). If excess of diacrylate is used in this reaction, the final polymer will have acrylate on both ends and useful as a degradable crosslinker.

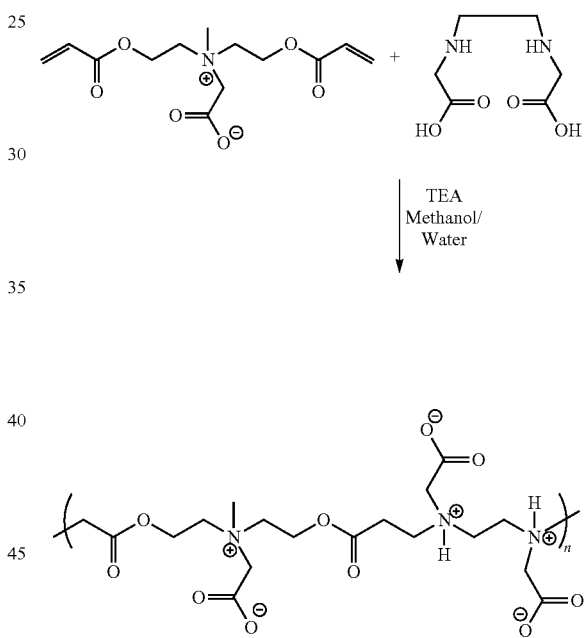

In the above scheme, the zwitterionic diacrylate is treated with ethylenediamine diaceticacid in methanol/water mixture for 6 days in presence of triethyl amine base. Solvents are removed from the polymer using freeze drying method. The final polymer is purified by using tetrahydrofuran (THF) as non-solvent.

Example 20

Representative Zwitterionic Polymer by Michael Addition: Diacrylate and Amino Acid In this example, the preparation of representative linear zwitterionic polymer is described. The linear polymers are formed by Michael addition of an amino acid (e.g., glycine) with a diacrylate.

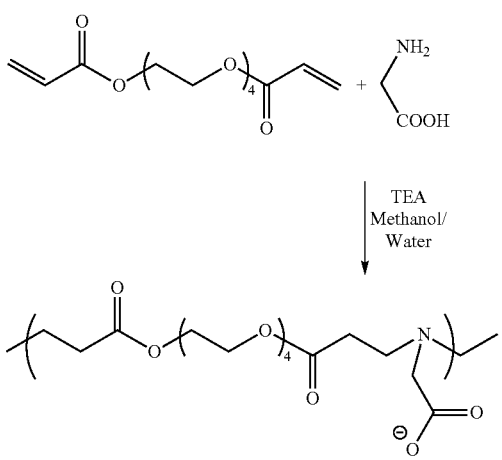

In the above scheme, the diacrylate is treated with glycine (an amino acid) in methanol/water mixture to provide the linear polymer.

In a typical reaction 5 g of glycine (0.066 mol) is treated with 22 g of tetraethyleneglycol dicarylate (0.066 mol) in presence of 20 g (0.199 mol) of trimethylamine in 20 g of water. The reaction was allowed to run at room temperature for 6 days in presence of triethylamine base. Solvents are removed from the polymer using freeze drying method. The final polymer is purified by precipitating in tetrahydrofuran (THF) as non-solvent. The molecular weight of the obtained polymer is around 2500 as measured by MALDI.

Example 21

Representative Zwitterionic Polymer by Michael Addition: Diacrylate and Amino Acid In this example, the preparation of representative zwitterionic polymer, a linear carboxybetaine that includes ester bonds in the polymer backbone, is described. The linear polymers are formed by Michael addition of an amino acid (e.g., glycine) with a zwitterionic diacrylate.

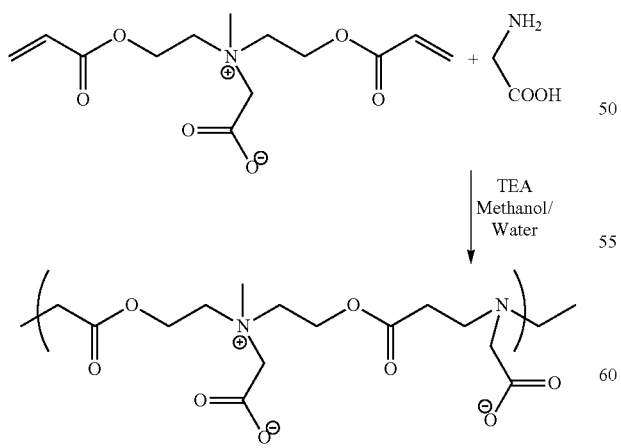

In the above scheme, the zitterionic diacrylate is treated with glycine (an amino acid) in methanol/water mixture for 6 days in presence of triethylamine base. Solvents are removed from the polymer using freeze drying method. The final polymer is purified by using tetrahydrofuran (THF) as non-solvent.

Example 22

Representative Zwitterionic Polymer by Ring Opening Metathesis Polymerization

In this example, the preparation of representative zwitterionic polymers by ring opening metathesis polymerization (ROMP) is described. Synthesis of zwitterionic monomer (3-cyclopentene-1-carboxylic acid) and zwitterionic polymer via ring opening metathesis is shown below.

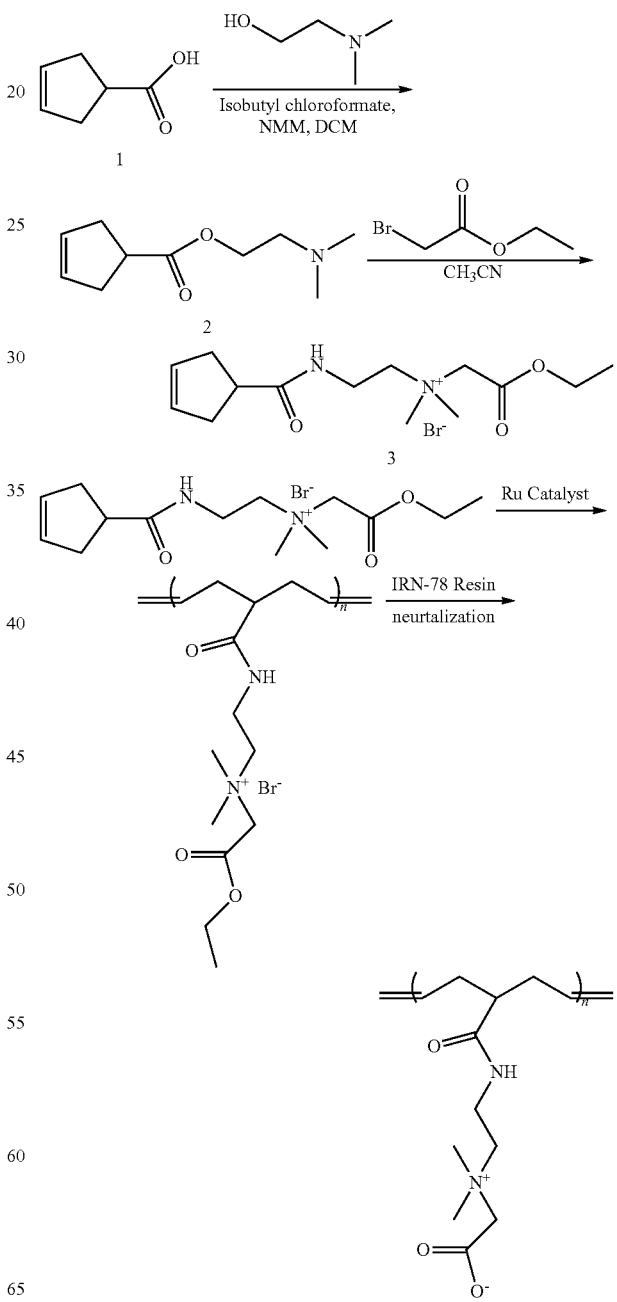

Referring to the above schemes, 3-cyclopente-1-carboxylic acid 1 is coupled with N,N-dimethylethanolamine using isobutylchloroformate to give compound 2. Reaction of compound 2 with ethyl bromoacetate gives ethyl protected zwitterionic monomer 3.

Synthesis of ROMP monomer: To a stirred solution of cyclopent-3-ene carboxylic acid (1.0 eq.) in 50 ml THF, NMM (1.0 eq.) is added. The solution is cooled to 0° C. After 10 minutes, isobutyl chloroformate (1.1 eq.) is added. After stirring for 15 minutes, N,N'-dimethylethylene diamine (1.1 eq.) and NMM (1.1 eq.) is added. The reaction is allowed to stir for two hours and the reaction contents are purified by flash chromatography to give desired compound 2 in 84% yield. Compound 2 (1.0 eq) is then taken in 10 ml acetonitrile and ethyl bromoacetate (1.1 eq.) is added. The reaction is stirred at 55° C. for two hours to give crude product which is then purified by flash chromatography to give desired compound in 67% yield.

$^1$H NMR (500 MHz, Deuterium Oxide) δ 5.69 (m, 2H), 4.35 (s, 2H), 4.29 (q, 0.1=7.2 Hz, 2H), 3.76 (m, 2H), 3.69 (m, 2H), 3.33 (s, 6H), 3.07 (m, 1H), 2.67-2.60 (m, 2H), 2.46 (m, 2H), 1.28 (t, J=7.1 Hz, 3H).

Synthesis of Zwitterionic Polymer by Ring Opening Metathesis Polymerization

To a stirred solution of ruthenium catalyst in aqueous HCl, zwitterionic ROMP monomer 4 is added and the reaction is carried out at 45° C. Upon completion, the polymerization reaction is terminated using triethylene glycol methyl vinyl ether.

Example 23

Representative Zwitterionic Polymer by Ring Opening Polymerization

In this example, the preparation of representative zwitterionic polymers by ring opening polymerization is described. Synthesis of zwitterionic monomer and ring opening polymerization of the monomer to produce the linear zwitterionic polymer is shown below.

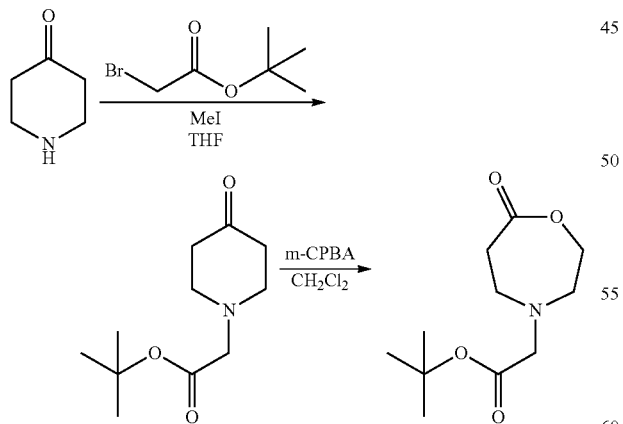

Synthesis of lactone monomer: To the solution of piperidin-4-one (10 mmol) in THF (20 mL) was added tert-Butyl bromoacetate (11 mmol), and the mixture was stirred for 4 h. The mixture was poured to H$_2$O and extracted with EtOAc (3×). The combined organic was washed with brine, dried with Na$_2$SO$_4$. The solvent was removed under vacuum to afford the crude amineketone, which was used for next step without purification. To the suspension of crude amineketone (1 mmol) in CH$_2$Cl$_2$ was added m-CPBA (2 mmol) at 0° C. The mixture was stirred for 8 h at room temp. The aqueous Na$_2$S$_2$O$_3$ was added and the mixture was extracted with CH$_2$Cl$_2$, washed with brine and dried with Na$_2$SO$_4$. The solvent was removed under vacuum, and the residual was purified with flash column (MeOH:CH$_2$Cl$_2$ 1:4) to give desired lactone (40% for 3 steps).

$^1$H NMR (400 MHz, CDCl$_3$) δ 1.47 (s, 9H), 2.52 (t, J=7.9 Hz, 2H), 2.94 t, J=7.9 Hz, 2H), 3.26 (s, 2H), 3.80 (m, 2H), 4.25 (m, 2H).

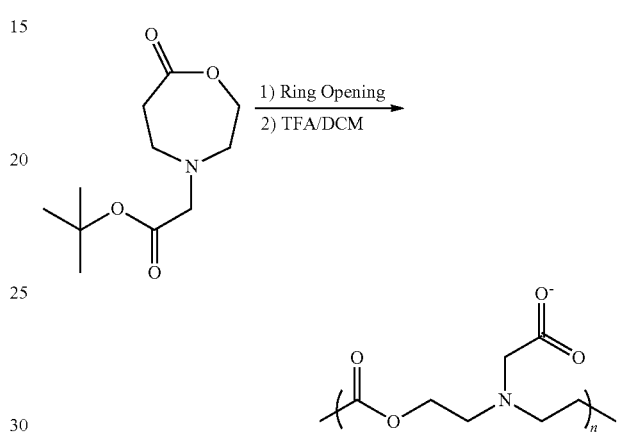

Ring opening of the lactone followed by treatment with TFA/DCM and IRN-78 resin neutralization gives linear zwitterionic polymer.

Example 24

Representative Zwitterionic Polymer by Ring Opening Polymerization

In this example, the preparation of representative zwitterionic polymers by ring opening polymerization is described. Synthesis of a linear branched zwitterionic polymer (polycarboxybetaine) is shown below.

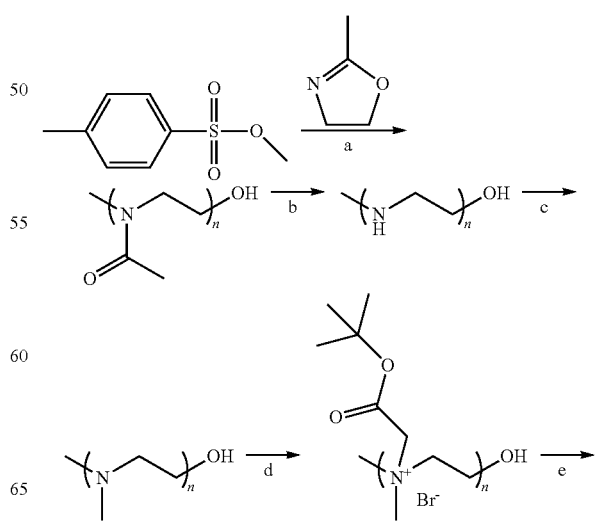

-continued

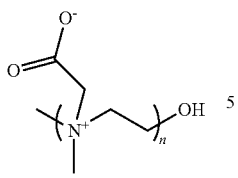

Referring to the above scheme, poly(methylethylenimine) (PMEI) was prepared and then dissolved in anhydrous DMF (0.05:1). Tert-butyl bromoacetate was added in three times molar excess to tertiary amine. The reaction took place at 60° C. overnight. The product was precipitated into ether three times by redissolving into new DMF. The poly(carboxybetaine tert-butyl ester) was dissolved in minimal trifluoroacetic acid (TFA). The deprotection was allowed to react for 3 hours. The polymer product was obtained by precipitation in ether, dissolved in water, and further purified by dialysis for 3 days. The solution was then lyophilized to give a pure white solid.

Example 25

Representative Zwitterionic Polymer: Linear Polycarboxybetaine

In this example, the preparation of representative zwitterionic polymers, a linear polycarboxybetaine, is described and shown below.

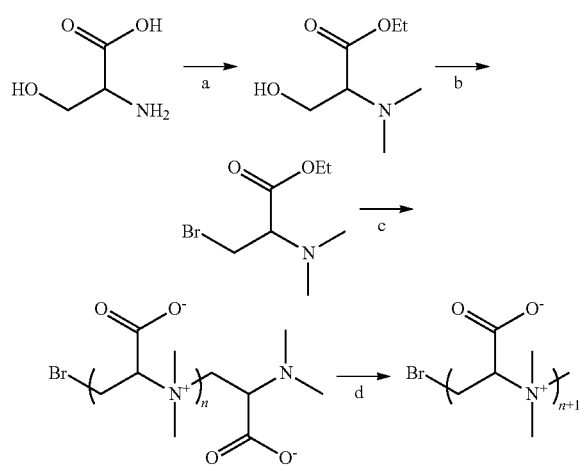

Referring to the above scheme, DL-serine was esterified with ethanol in the presence of an excess of thionyl chloride. Subsequent reductive amination is achieved using a mixture of formaldehyde and sodium triacetoxyborohydride (STAB-H) to afford the N,N-dimethylated serine ester (a). Bromination of the hydroxyl group is done by reacting the monomer with thionyl bromide (b). Polymer is formed by refluxing in a solution of water and methanol, and hydrolysis of the ethyl esters yield the linear carboxybetaine (c). The dimethylamine end of the polymer is capped using a methylation with an excess of iodomethane at 50° C. (d).

Example 26

Representative Zwitterionic Polymer: Double Alternating Charge Linear Polycarboxybetaine In this example, the preparation of representative zwitterionic polymers, a double alternating charge linear polycarboxybetaine, is described and shown below.

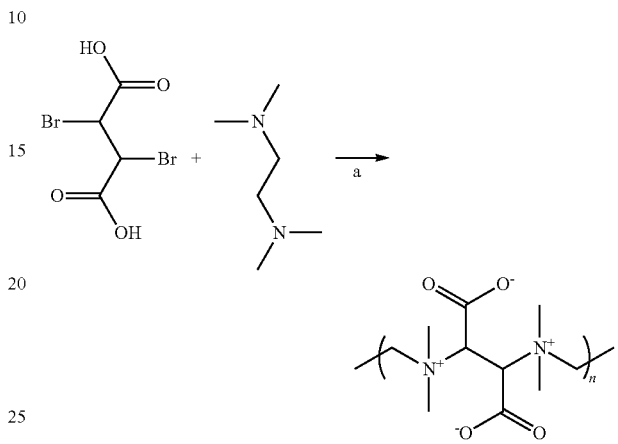

Referring to the above scheme, 1.52 g of 2,3-dibromosuccinic acid (0.0055 mol) and 0.645 g of tetramethyl ethylenediamine (0.0055 mol) were dissolved in a mixture of 10 mL water and 10 mL 2-propanol. The solution was refluxed at 110° C. for 1 day. The polymer was obtained by precipitating in THF and purified by repeated precipitation.

Example 27

Representative Zwitterionic Polymer: Proline-Based Linear Polymer by Polycondensation In this example, the preparation of representative zwitterionic polymers, proline-based linear polymer, by polycondensation is described and shown below.

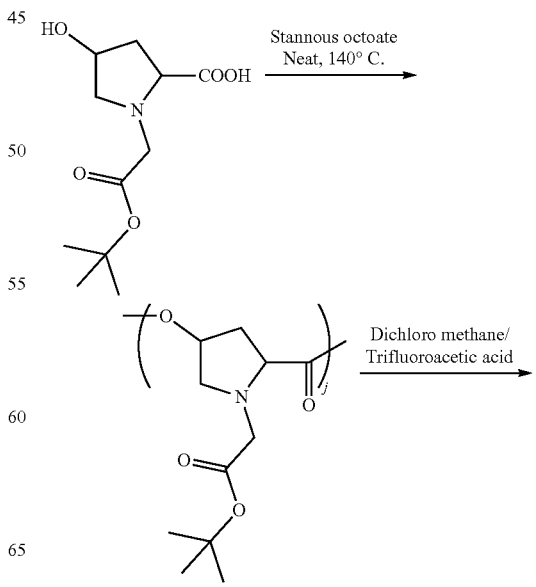

67

-continued

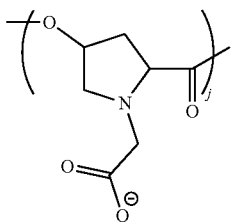

In the above scheme, tert-butyl acetate protected hydroxyl proline is polymerized at 140° C. under vacuum with stannous octoate catalyst. The deprotection of the tertiary butyl group was carried out by trifluoroacetic acid to obtain the proline-based linear zwitterionic polymer.

Tertiary amine protected hydroxyl proline is subjected to polycondensation reaction at 140° C. in presence of stannous octoate catalyst under vacuum. The reaction was carried out for 6 h. The final polymer is a brown sticky highly viscous substance that is soluble in organic solvents such as chloroform and dichloromethane. Proton NMR in deuterated chloroform was used to confirm the presence of tertiary butyl group. The tertiary group was deprotected by treating the polymer with trifluoroacetic acid in dichloromethane at room temperature. The final proline-based zwitterionic polymer was found to have a molecular weight around 2000 when analyzed by MALDI-ToF.

Example 28

Representative Post-Modification of the End Group

In this example, the various post-polymer formation modifications are described. Post-formation modifications include conversion to mono-methacrylate, conversion to a crosslinkable polymer (dimethacrylate), modification for binding to a protein, modification for surface coating.

68

Methacrylate

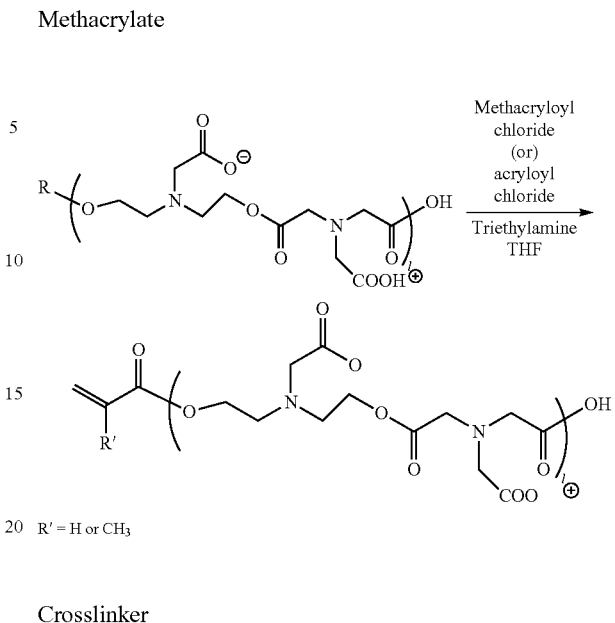

R' = H or CH$_3$

Crosslinker

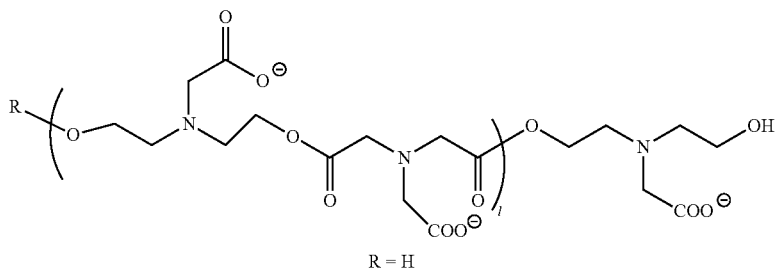

R = H

Methacryloyl chloride (or) acryloyl chloride/ Triethylamine/THF

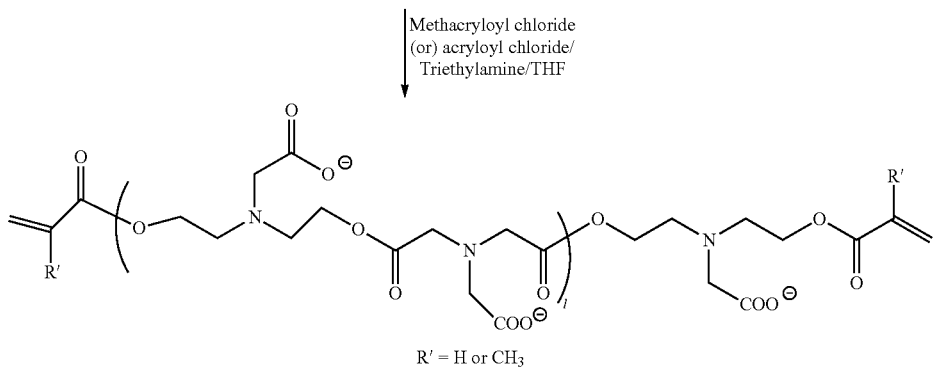

R' = H or CH$_3$

Protein Binding

X=—SH, —NH$_2$.

Surface Coating

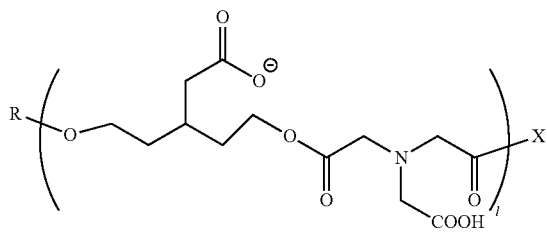

X=—SH, —NH$_2$, silanes, (dihydroxyphenylamine) DOPA, aldehyde, —COOH, epoxy.

Example 29

Preparation of PTCBE Crosslinked Bulk Polymers

A reaction mixture containing TCBE monomer, 0.5, 1.0, 1.5 or 2.0 wt % (relative to the weight of TCBE monomer) of crosslinker EGDMA and 1 wt % (relative to the weight of TCBE monomer) of initiator AIBN was thermo-polymerized using sheet mold and tubular mold. The oxygen in the reaction mixture was removed by bubbling with nitrogen gas for 60 minutes. Note that no solvent is used in this system. The PTCBE bulk polymers with different crosslinker were coded as PTCBE-x, where x stands for the wt % of crosslinker relative to the weight of TCBE monomer. For the sheet mold, the solutions was polymerized between two glass microscope slides separated by 0.5 mm thick polytetrafluoroethylene (PTFE) spacers at 50° C. for three days and followed by 80° C. for another three hours. For tubular mold, the solution was casted into tube with inner diameter 5 mm. The obtained PTCBE bulk polymer samples were soaked thoroughly until equilibrium into 10 mM phosphate-buffered saline (PBS) buffer solutions (pH 7.4) at 37° C. before tests of mechanical properties. For tests of biological properties, equilibrium samples were sterilized under UV 254 nm for 45 minutes.

Example 30

Method for Measuring Mechanical Properties: Compression and Tensile Tests

Compression and tensile tests were performed to record the mechanical behavior of the PTCBE samples. A tensile-compressive tester Instron 5543A mechanical tester (Instron Corp., Norwood, Mass.) with a 10 kN load cell was used to perform the tests. For compression tests, cylinder samples were made from tubular mold with diameter and height of 5 mm and 4 mm, respectively. The cylinder samples were compressed to failure at a rate of 1 mm/min and the compressive modulus was calculated from the initial 10% strain. Average data was acquired by testing five specimens for each PTCBE sample. The fracture compression stress, fracture compression strain and compressive modulus were recorded. For tensile tests, samples made from sheet mold were cut into rectangular pieces with dimensions of 20 mm*2 mm*0.5 mm. Crosshead speed was set at 10 mm/min and average data was acquired by testing five specimens for each PTCBE sample. The fracture tensile stress, fracture tensile strain and automatic Young's modulus were recorded.

Example 31

Method for Measuring Nonfouling Properties: ELISA Tests

To measure fibrinogen (Fg) adsorption, all of the disk samples (5 mm in diameter, cut from samples made of sheet mold) with the same surface area including the positive control tissue culture polystyrene (TCPS) and negative control regular anti-fouling polycarboxybetaine (PCB) hydrogel, was first incubated with 1 ml of PBS solution containing of 1 mg/ml Fg and 1 ug/ml horseradish peroxidase (HRP) conjugated anti-fibrinogen for 1.5 hours. All samples were taken out following by another 5 washes with pure PBS buffer. Finally, all samples were transferred to a new 24-well plate. A standard curve was determined for the concentration range of 1-1000 ng/mL horseradish peroxidase (HRP) conjugated anti-fibrinogen in twofold serial dilutions. Then 1 ml of 1 mg/ml o-phenylenediamine (OPD) 0.1 M citrate phosphate pH 5.0 buffer, containing 0.03% hydrogen peroxide was added to wells of samples and horseradish peroxidase (HRP) conjugated anti-fibrinogen respectively. After incubation of 15 min, the reaction was stopped by adding an equal volume of 2M H$_2$SO$_4$. Absorbance value at 492 nm was recorded by a plate reader. Five specimens of each sample were averaged for comparison.

While illustrative embodiments have been illustrated and described, it will be appreciated that various changes can be made therein without departing from the spirit and scope of the invention.

The invention claimed is:

1. A bulk material comprising a crosslinked polymer having tensile and compressive strengths greater than about 0.5 MPa and a fibrinogen adsorption of less than about 30 ng/cm$^2$ in a fibrinogen binding assay when the material is incubated at 37° C. for 90 minutes with a 1.0 mg/ml fibrinogen solution that is 0.15 M phosphate buffered saline at pH 7.4, the crosslinked polymer having a hydrophobic interior comprising (a) a polymer backbone, (b) a plurality of nitrogen centers, each nitrogen center covalently coupled to a polymer backbone by a first linker, (c) optionally a counter ion associated with each nitrogen center, and (d) a hydrolyzable group covalently coupled to each nitrogen center through a second linker, wherein the hydrolyzable group is hydrolyzable to an anionic center to provide a polymer having the anionic center covalently coupled to the nitrogen center through the second linker, the crosslinked polymer having a hydrophilic exterior comprising (a) a polymer backbone, (b) a plurality of nitrogen centers, each nitrogen center covalently coupled to a polymer backbone by a first linker, and (c) an anionic center covalently coupled to each nitrogen center through a second linker, wherein the anionic center is provided via hydrolysis of the hydrolyzable group, wherein the crosslinked polymer comprises a repeating unit having the formula:

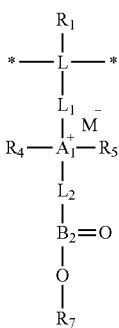

R₁ is selected from the group consisting of hydrogen, fluorine, trifluoromethyl, C1-C20 alkyl, C6-C12 aryl, and CN groups;

R₄ is selected from the group consisting of hydrogen, C1-C20 alkyl, C6-C12 aryl, cyclic alkyl, fluoroalkyl, and void;

R₅ is selected from the group consisting of hydrogen, C1-C20 alkyl, C6-C12 aryl, cyclic alkyl, and fluoroalkyl;

R₇ is C1-C20 alkyl, C6-C12 aryl, cyclic alkyl, or fluoroalkyl,

L is C or Si;

L₁ at each occurrence is selected from —(CH₂)ₓ—, —(CH(CN))ₓ—, —C(=O)NH(CH₂)ₓ—, —C(=O)O(CH₂)ₓ—, —C(=O)OC(=O)O(CH₂)ₓ—, —(CH₂)ₓ—O—(CH₂)ₓ—, or —(CH₂)ₓ—S—S—(CH₂)ₓ—, where x at each occurrence is an integer independently selected from 0 to 20;

L₂ at each occurrence is selected from —(CH₂)ₓ— or —(CH(CN))ₓ—, where x is an integer from 1 to 20;

A₁ is N;

B₂ is C; and

M is selected from Cl, Br, I, SO₄, NO₃, ClO₄, BF₄, PF₆, N(SO₂CF₃)₂, SO₃CF₃, RCOO (R is C1-C20 alkyl), lactate, benzoate, salicylate, or void.

2. The bulk material of claim 1, wherein R₁ is C1-C20 alkyl; R₄ is hydrogen, C1-C20 alkyl, or void; R₅ is hydrogen or C1-C20 alkyl; R₇ is C1-C20 alkyl or cyclic alkyl; L is C; L₁ at each occurrence is —C(=O)NH(CH₂)ₓ— or —C(=O)O(CH₂)ₓ—; and L₂ is —(CH₂)ₓ—.

3. The bulk material of claim 1, wherein R₁ is methyl.

4. The bulk material of claim 1, wherein L is C.

5. The bulk material of claim 1, wherein L₁ is —C(=O)O(CH₂)₂—.

6. The bulk material of claim 1, wherein R₄ is void and R₅ is methyl.

7. The bulk material of claim 1, wherein L₂ is —(CH₂)—.

8. The bulk material of claim 1, wherein R₇ is methyl, ethyl, cyclopentyl, cyclohexyl, or isonorbornyl.

9. A composite, comprising the bulk material of claim 1 and a second polymer.

10. The composite of claim 9, wherein the second polymer is selected from the group consisting of polyesters, polycarbonates, polyurethanes, polyureas, polysulfides, polysulfones, polyimides, polyepoxies, aromatic polyesters, cellulosics, fluoropolymers, polyacrylics, polyamides, polyanhydrides, polyethers, vinyl polymers, phenolics, elastomers, and other addition polymers.

11. The composite of claim 9 further comprising a strength additive.

12. The composite of claim 9 further comprising a strength additive selected from the groups consisting of fiber, clays, nanotubes, and other inorganic objects.

13. The bulk material of claim 1 formed by a method selected from the group consisting of injection molding, blow molding, extrusion molding, calendaring molding, flow casting, compression molding, prevarication molding, and 3D printing.

14. A surface coating for a substrate, comprising the bulk material of claim 1.

15. The surface coating of claim 14, wherein the substrate is a marine product.

16. The surface coating of claim 14, wherein the substrate is a marine product selected from the group consisting of marine vessel hulls, marine structures, bridges, propellers, heat exchangers, periscopes, sensors, fish nets, cables, tubes/pipes, containers, membranes, and oil booms.

17. The surface coating of claim 14, wherein the substrate is a biomedical product.

18. The surface coating of claim 14, wherein the substrate is a biomedical product selected from the group consisting of catheters, ear drainage tubes, feeding tubes, glaucoma drainage tubes, hydrocephalous shunts, keratoprosthesis, nerve guidance tubes, tissue adhesives, x-ray guides, artificial joints, artificial heart valves, artificial blood vessels, pacemakers, left ventricular assist devices (LVAD), artery grafts, vascular grafts, stents, intravascular stents, cardiac valves, joint replacements, blood vessel prostheses, skin repair devices, cochlear replacements, contact lenses, artificial ligaments and tendons, dental implants, and tissue scaffolds for regenerative tissue engineering.

19. The surface coating of claim 14, wherein the substrate is a delivery vehicle selected from the group consisting of a drug delivery vehicle, a gene delivery vehicle, an RNA delivery vehicle, and a protein vehicle.

* * * * *